(12) United States Patent
Ahlfors et al.

(10) Patent No.: US 9,944,674 B2
(45) Date of Patent: Apr. 17, 2018

(54) SELECTIVE CYSTEINE PROTEASE INHIBITORS AND USES THEREOF

(75) Inventors: Jan-Eric Ahlfors, Laval (CA); Khalid Mekouar, Laval (CA)

(73) Assignee: Genesis Technologies Limited, Warrens (BB)

( * ) Notice: Subject to any disclaimer, the term of this patent is extended or adjusted under 35 U.S.C. 154(b) by 0 days.

(21) Appl. No.: 14/111,738

(22) PCT Filed: Apr. 15, 2012

(86) PCT No.: PCT/IB2012/000747
§ 371 (c)(1),
(2), (4) Date: Oct. 14, 2013

(87) PCT Pub. No.: WO2012/140500
PCT Pub. Date: Oct. 18, 2012

(65) Prior Publication Data
US 2014/0038903 A1    Feb. 6, 2014

Related U.S. Application Data

(60) Provisional application No. 61/476,183, filed on Apr. 15, 2011.

(51) Int. Cl.
| | | |
|---|---|---|
| *C07K 5/103* | (2006.01) | |
| *C07K 5/02* | (2006.01) | |
| *C07K 5/083* | (2006.01) | |
| *C07K 5/062* | (2006.01) | |
| *C07K 5/065* | (2006.01) | |
| *C07K 5/072* | (2006.01) | |
| *C07K 5/087* | (2006.01) | |
| *C07K 5/093* | (2006.01) | |
| *C07K 5/097* | (2006.01) | |
| *C07K 14/81* | (2006.01) | |
| *A61K 38/06* | (2006.01) | |

(52) U.S. Cl.
CPC ............ *C07K 5/1008* (2013.01); *C07K 5/02* (2013.01); *C07K 5/06026* (2013.01); *C07K 5/06034* (2013.01); *C07K 5/06078* (2013.01); *C07K 5/06095* (2013.01); *C07K 5/06104* (2013.01); *C07K 5/06113* (2013.01); *C07K 5/081* (2013.01); *C07K 5/0806* (2013.01); *C07K 5/0808* (2013.01); *C07K 5/0812* (2013.01); *C07K 5/0819* (2013.01); *C07K 5/0821* (2013.01); *C07K 14/8139* (2013.01); *A61K 38/06* (2013.01)

(58) Field of Classification Search
CPC ............ C07K 5/1008; C07K 5/06034; C07K 5/06078; C07K 5/06095; C07K 5/06104; C07K 5/06113; C07K 5/0806; C07K 5/0808; C07K 5/081; C07K 5/0812; C07K 5/0819; C07K 5/0821; C07K 5/06026; A61K 38/06
See application file for complete search history.

(56) References Cited

U.S. PATENT DOCUMENTS

| | | |
|---|---|---|
| 3,341,331 A | 9/1967 | Kimura et al. |
| 3,640,716 A | 2/1972 | Nagae et al. |
| 4,269,936 A | 5/1981 | Arai et al. |
| 5,278,148 A | 1/1994 | Branca et al. |
| 5,976,858 A | 11/1999 | Palmer |
| 6,287,840 B1 | 9/2001 | Palmer |
| 7,256,198 B2 | 8/2007 | Dollings |
| 7,589,066 B2 | 9/2009 | Orlowski |
| 8,791,235 B2 | 7/2014 | Ahlfors et al. |
| 9,045,524 B2 | 6/2015 | Ahlfors et al. |
| 9,562,059 B2 | 2/2017 | Ahlfors et al. |
| 2004/0005650 A1 | 1/2004 | Edris |
| 2008/0220416 A1 | 9/2008 | Miele |
| 2008/0227976 A1 | 9/2008 | Mortimore |
| 2011/0077190 A1 | 3/2011 | Ahlfors et al. |
| 2012/0157394 A1 | 6/2012 | Ahlfors |
| 2014/0038903 A1 | 2/2014 | Ahlfors et al. |

FOREIGN PATENT DOCUMENTS

| | | | |
|---|---|---|---|
| CA | 2589460 A1 | 6/2006 | |
| CN | 1513871 | 7/2004 | |
| CN | 101161672 | 4/2008 | |
| JP | S 4818256 | 6/1973 | |
| JP | H 11503417 | 3/1999 | |
| JP | 2002-145848 A | * 5/2002 | ........... C07K 271/22 |
| JP | 2002145848 | 5/2002 | |

(Continued)

OTHER PUBLICATIONS

Bavikar et al, Pd-catalyzed one-pot chemoselective hydrogenation protocol for the preparation of carboxamides directly from azides, Tetrahedron Letters, 2010, 51, pp. 3815-3819.*

(Continued)

*Primary Examiner* — Julie Ha
*Assistant Examiner* — Li N Komatsu
(74) *Attorney, Agent, or Firm* — Knobbe, Martens, Olson & Bear, LLP

(57) ABSTRACT

The present invention relates to compounds of Formula I, II, IA-VA, IVA1-IVA5, IIIA1-IIIA5 and their pharmaceutical uses. Particular aspects of the invention relate to the use of those compounds for the selective inhibition of one or more cysteine proteases. Also described are methods where the compounds of Formula I, II, IA-VA, IVA1-IVA5, IIIA1-IIIA5 are used in the prevention and/or treatment of various diseases and conditions in subjects, including cysteine protease-mediated diseases and/or caspase-mediated diseases such as sepsis, myocardial infarction, cancer, tissue atrophy, ischemia, ischemic stroke, spinal cord injury (SCI), traumatic brain injury (TBI) and neurodegenerative diseases such as multiple sclerosis (MS), amyotrophic lateral sclerosis (ALS), Alzheimer's disease, Parkinson's disease, and Huntington's disease.

26 Claims, No Drawings

(56) References Cited

FOREIGN PATENT DOCUMENTS

| WO | 9523222 | 8/1995 | | |
|---|---|---|---|---|
| WO | 9630395 | 10/1996 | | |
| WO | WO 96/30353 | 10/1996 | | |
| WO | 9743305 | 11/1997 | | |
| WO | 9842342 | 10/1998 | | |
| WO | WO 99/31122 | 6/1999 | | |
| WO | WO 99/48910 | 9/1999 | | |
| WO | WO 99/57135 | 11/1999 | | |
| WO | 0142216 | 6/2001 | | |
| WO | 0190070 | 11/2001 | | |
| WO | 0194351 | 12/2001 | | |
| WO | 0222611 | 3/2002 | | |
| WO | 0242278 | 5/2002 | | |
| WO | WO 03/016335 | 2/2003 | | |
| WO | WO 2005/021516 A1 | * | 3/2005 | ........... C07D 261/04 |
| WO | WO 2006/032457 A1 | 3/2006 | | |
| WO | WO 2006/082434 A1 | 8/2006 | | |
| WO | 2008008264 | 1/2008 | | |
| WO | WO 2009/140765 A1 | 11/2009 | | |
| WO | WO 2010/133000 A1 | 11/2010 | | |
| WO | 2012140500 | 10/2012 | | |

OTHER PUBLICATIONS

Isaacs et al, Structure-based design of novel groups for use in the P1 position of thrombin inhibitor scaffolds. Part 1: Weakly basic azoles, Bioorganic & Medicinal Chemistry Letters, 2006, 16, pp. 338-342.*
Machine translation of JP 2002-145848 A, pp. 1-28, accessed Sep. 24, 2014.*
Kam et al, Design and evaluation of inhibitors for dipeptidyl peptidase I (Cathepsin C), Archives of Biochemistry and Biophysics, 2004, 427, pp. 123-134.*
Bavikar, et al., Pd-catalyzed one-pot chemoselective hydrogenation protocol for the preparation of carboxamides directly from azides, Teltrahedron Letters, 51:3815-9 (2010).
Beaumont, et al., "Design of ester prodrugs to enhance oral absorption of poorly permeable compound: Challenges to the discovery scientist", Curr Drug Metabolism, 4:461-85 (2003).
Berdowska, "Cysteine proteases as disease markers", Clinica Chimica Acta, 342:41-69 (2014).
Definition of Derivative, On-line Medical Dictionary, 3 pages, accessed Jul. 7, 2005.
Definition of Peptidomimetic, retrieved on line from Chemicool.com, 1 page , (2013).
Ettmayer, et al., "Lessons learned from marketed and invesrigational prodrugs", Med. Chem., 47(10):2394-2404 (2004).
Ewing, et al., "Design and structure-activity relationships of potent and selective inhibitors of blood coagulation factor Xa", J Med. Chem., 42:3557-71 (1988).
Gloria, et al., Aspartic vinyl sulfones: Inhibitors of a caspase-3 dependent pathway, Eu J Med. Chem.,46:2141-6 (2011).
Grzonka, et al., "Cystine Proteases", Ind. Enzymes, 181-95 (2007).
Han, "Targeted prodrug design to optimize drug delivery", AAPS Pharmsci., 2 (1):1-11 (2000).
Han, et al., Papain-like protease 2 (PLP2) from severe acute respiratory coronavirus (SARS-CoV): Expression, purification, characterization and inhibition, Bio Chem., 44:10349-59 (2005).
Hanzlik, et al., "Communications to the editor", J Med. Chem., 27:711-2 (1984).
Liu, et al., "Structure-activity relationships for inhibition of papain by peptide Michael acceptors", J Med. Chem., 35:1067-75 (1992).
Merrifield, "Solid phase peptide synthesis. I. The synthesis of a tetrapeptide", J Am Chem Soc., 85:2149-54 (1963).
Müller, "Prodrug approaches, for enhancing the bioavailability of drugs with low solubility", Chem & Biodiv., 6:2071-83 (2009).
Nazif, et al., Global analysis of proteasomal substrate specificity using positional-scanning libraries of covalent inhibitors, PNAS 98:2967-72 (2001).
Newton, et al., "Synthesis and evaluation of vinyl sulfones as caspase-3 inhibitors: A structure-activity study", Eu J med. Chem., 45:3858-63 (2010).
Ng, et al., "Click" synthesis of small-molecule inhibitors targeting caspases, Organic & Biomolecular Chem., 6:844-7 (2008).
Rawlings, et al., "Evolutionary families of peptidases", Biochem. J., 290:205-18 (1993).
Rodriguez, et al., "Systemic injection of a tripeptide inhibits the intracellular activation of CPP32-like proteases in vivo and fully protects mice against fas-medicated fulminant liver destruction and death", J Exp Med., 184:2067-72 (1996).
Santos, et al., "Michael acceptors as cysteine protease inhibitors", Mini Reviews in Med. Chem., 7:1040-50 (2007).
Singh, et al., "recent trends in targeted anticancer prodrug and conjugate design", Curr Med Chem., 15(18)1802-26 (2008).
Testa, "Prodrug research: futile or ferrile", Biochem Pharma., 68:2097-2106 (2004).
Thompson, et al., "Carboxyl-modified amino acids and peptides as protease inhibitors", J Med. Chem., 29:104-11 (1986).
Tong, Liang, Viral proteases, Chem. Rev., 102:4609-26 (2002).
Uttamchandani, et al., "Activity-based fingerprinting and inhibitor discovery of cysteine proteases in a microarray", Chem. Commun., 1518-20 (2007).
Vyas, et al., "Formulation and physiological factors influencing CNS delivery upon intranasal administration", Critical Rev There Drug Carrier Sys., 23:319-47 (2006).
Wagh, et al., "allylic amination of internal alkynes with aromatic and aliphatic amines using polymer-supported triphenylphosphane-palladium complex as a heterogeneous and recyclavle catalyst", Eu J Organic Chem., 26:5071-6 (2010).
Winssinger, "Profiling protein function with small molecule microrrays", PNAS, 99(17):11139-44 (2002).
Yaoita, et al., "attenuation of ischemia/reperfusion injury in rats by a caspase inhibitor", Curr., 97:276-81 (1998).
Adessi et al., Converting a Peptide into a Drug: Strategies to Improve Stability and Bioavailability, Current Medicinal Chemistry, vol. 9, No. 9, May 2002, pp. 963-978(16).
Friedrich-Bochnitschek, et al., Allyl Esters as Carboxy Protecting Groups in the Synthesis of O-Glycopeptide, J. Org. Chem., 1989, 54, 751-756.
Götz, et al., Aza-peptidyl Michael Acceptors. A New Class of Potent and Selective Inhibitors of Asparaginyl Endopeptidases (Legumains) from Evolutionarily Diverse Pathogens, J. Med. Chem. 2008, 51, 2816-2832.
Isaacs, et al., Structure-based design of novel groups for use in the P1 position of thrombin inhibitor scaffolds. Part 1: Weakly basic azoles, Bioorganic & Medicinal Chemistry Letters, 2006,16, 338-342.
O'Donnell, et al., Serine-threonine protein phosphatase inhibitors derived from nodularin: role of the 2-methyl and 2-diene groups in the Adda residue and the effect of macrocyclic conformational restraint, J. Chem. Soc., Perkin Trans. 1, 2001, 1696-1708.
Entry from Seikagaku jitenn (a dictionary of biochemistry) (the $3^{rd}$ edition) Tokyo Kgaku Dojin, 2002, Jul. 1, the $5^{th}$ impression, pp. 290-291, (Japanese), English equivalent of this NPL is considered.
Kam, et al. Design and evaluation of inhibitors for dipeptidyul peptidase I (Cathepsin C), Archives of Biochemistry and Biophysics, 2004, pp. 123-134, vol. 427.
Talanian et al., Substrate Specificities of Caspase Family Proteases. J. Biol. Chem., vol. 272, No. 15, pp. 9677-9682, 1997.
International Search Report from International Application No. PCT/CA2009.000696 dated Jul. 9, 2009 (date of completion of search) and Sep. 1, 2009 (date of mailing of report).
Written Opinion from International Application No. PCT/CA2009.000696 dated Jul. 24, 2009 (date of completion of opinion) and Sep. 1, 2009 (date of mailing of opinion).
Burguillos, et al. Caspase Signalling Controls Microglia Activation and Neurotoxicity, Nature vol. 472, Apr. 21, 2011, pp. 319-325.
Calignon, et al., Caspase Activation Precedes and Leads to Tangles, Nature, vol. 464, Apr. 22, 2010, pp. 1201-1205.
Gdynia, et al., Basal Caspase Activity Promotes Migration and Invasiveness in Glioblastoma Cell, Molecular Cancer Research 2007; 5(12), Dec. 2007, pp. 1232-1240.
Huang, et al., Caspase 3—Meditated Stimulation of Tumor Cell Repopulation During Cancer Radiotherapy, Nature Medicine, vol. 17, No. 7, Jul. 2011, pp. 860-867.

(56) References Cited

OTHER PUBLICATIONS

Hyman, Caspase Activation Without Apoptosis: Insight Into AB Initiation of Neurodegeneration, Nature Neuroscience, vol. 14, No. 1, Jan. 2011, pp. 5-6.
Kakinohana, et al. Delayed Paraplegia After Spinal Cord Ischemic Injury Requires Caspase-3 Activation in Mice, Stroke. Aug. 2011: 42 (8): 2302-2307.
LeBlanc, et al. Caspase-6 as a Novel Early Target in the Treatment of Alzheimer's Disease, European Journal of Neuroscience, vol. 37, pp. 2005-2018, 2013.
Li, et al. Caspase-Dependent Retinal Ganglion Cell Apoptosis in the Rat Model of Acute Diabetes, Chin Med. Journal 2008; 121(24):2566-2571, pp. 2566-2571.
Nikolaev, et al. N-APP Binds DR6 to Cause Axon Pruning and Neuron Death via Distinct Caspases, Nature, Feb. 19, 2009; 457(7232): 984-989.
Plant, et al. Absence of Caspase-3 Protects Against Denervation-Induced Skeletal Muscle Atrophy, Journal of Applied Physiology 107: 224-234, 2009.
Radziszewska, et a. Absence of Caspase-3 Protects Pancreatic B-Cells From C-MYC-Induced Apoptosis Without Leading to Tumor Formation, The Journal of Biological Chemistry vol. 284, No. 16, pp. 10947-10956, Apr. 17, 2009.
Takagi, et al., Caspase Activation in Neuronal and Glial Apoptosis Following Spinal Cord Injury in Mice, Neurol. Med. Chir. (Tokyo) 43, Jan. 2003, pp. 20-30.
Linton, Steven D., "Caspase Inhibitors: A Pharmaceutical Industry Perspective", Current Topics in Medicinal Chemistry, 2005, 1697-1717, 5.

\* cited by examiner

SELECTIVE CYSTEINE PROTEASE INHIBITORS AND USES THEREOF

FIELD OF THE INVENTION

The present invention relates to chemical compounds and their pharmaceutical uses. More particularly, the invention relates to selective inhibitors of cysteine proteases (CPs) including caspases and their uses for the prevention and/or treatment of various diseases and conditions in subjects.

BACKGROUND OF INVENTION

In humans, CPs are responsible for apoptosis, MHC Class II immune responses, prohormone processing and intracellular and extracellular matrix remodeling. As examples of CPs, there are: Actinidain, Bromelain, Calpains, Caspases, Cathepsins, Mir1-CPs, and Papain. CPs have also been recognized as critical enzymes in degenerative and autoimmune states (Zbigniew et al. 2007, Industrial Enzymes, book, 181-195). As an example, tumor cell invasion and metastasis are associated with the proteolytic activities of various types of proteases. Elevated expression of certain Cathepsins and diminished levels of their inhibitors have been reported to be involved in several human cancers, including brain, breast, gastric, glioma, prostate, lung, head and neck cancer and melanoma (Berdowska, Clinica Chimica Acta 342 (2004) 41-69). Beside cancers, Cathepsins have been reported to be involved in inflammatory diseases, such as inflammatory myopathies, rheumatoid arthritis and periodontitis.

Cysteine proteases of the papain family have been reported to play an important role in microbial (viral, bacterial) and parasitic infectious (Tong et al, 2002, Chem. Rev. 102, 4609-4626 and Han et al, 2005, Biochemistry 44, 10349-10359).

Caspases comprise a family of cysteine protease enzymes with a well-known role as key mediators in apoptosis signaling pathways and cell disassembly. Interleukin converting enzyme (ICE), also known as Caspase-1, was the first identified caspase and has a proinflammatory role. There is growing evidence demonstrating the role of caspases in very diverse pathologies. For instance it is known that proapoptotic caspases are involved in the pathogenesis of many cardiovascular disorders. Some proapoptotic caspases such as caspase-8 also possess non-apoptotic function that may contribute to tumor progression. Caspase-1 plays an important role in the response to pathogenic infection as well as in inflammatory and autoimmune disorders. In addition, caspase-1 activity is increased in retinas of diabetic patients and it constitutes a critical regulator of cardiomyocyte programmed cell death in the mammalian heart. Caspases also play a role in neurodegenerative diseases and trauma. For instance, it has been shown that the caspase-3 cascade is highly activated in traumatic spinal cord injury. Finally, the activation of caspase-1 and caspase-3 in Amyotrophic Lateral Sclerosis (ALS) patients and the activation of caspase-7, -8, and -9 in a mouse model at end stage of ALS have been reported. Increased levels of apoptosis and caspase activity (especially caspase-3) are reported to be frequently observed at sites of cellular damage in both acute (e.g. sepsis, myocardial infarction (MI), ischemic Stroke, spinal cord injury (SCI), traumatic brain injury (TBI)) and neurodegenerative disease (e.g. Alzheimer's, Parkinson's and Huntington's diseases, and multiple sclerosis (MS)). Caspase-6 is implicated in many neurodegenerative diseases including Alzheimer and Huntington's diseases. In Alzheimer's caspase-6 has been shown to cut amyloid precursor protein (APP) and Tau leading to a toxic fragment. In Huntington's disease, caspase-6 may be responsible for the type of Huntington fragments that lead to nerve cell death and symptoms.

Since caspases are involved in a number of diseases, several compounds and methods have been developed to inactivate them. For example, the broad irreversible caspase inhibitor benzyloxycarbonyl-Val-Ala-Asp-fluoromethylketone (z-VAD-fmk) was protective and efficiently blocked death receptor-mediated liver injury in animal models (Rodriguez et al. (1996), J Exp Med. 1996 Nov. 1; 184(5):2067-72). Myocardial infarction and the resulting death of myocytes was ameliorated by z-VAD-fmk and related peptide inhibitors in animal models (Yaoita et al., 91998) *Circulation* 97: 276-281). There has been a lot of effort into identifying inhibitors of peptidase. For instance, Hanzlik and Thompson (J. Med. Chem. (1984), 27(6), 711-712) describe vinylogous amino acid esters for inactivating thiol proteases. Thompson et al. (J. Med. Chem. (1986), 29(1), 104-111) describe carboxyl-modified amino acids and peptides as protease inhibitors. Liu and Hanzlik have prepared a series of peptidyl Michael acceptors with different electron withdrawing groups with different recognition and binding groups as inactivators against papain, a member of the cysteine proteinase family.

However, most of these prior art compounds are reversible inhibitors with diminished efficacy over time and safety problems. The diminished efficacy over time and safety problems are due to these compounds being reversible inhibitors of cysteine proteases that also have a "pro-" form of the cysteine protease; for example, a reversible caspase inhibitor causes more of the pro-caspase in the cell to turn into caspase (due to chemical equilibrium and similar effects) with the end effect being that when the reversible inhibitors release their caspase and leave the cell (or are metabolized), the cell ends up with more caspase than it had to begin with—thus the net effect of the reversible caspase inhibitors over time is the opposite of the desired effect of lowering the caspase levels, causing potentially significant side-effects and safety problems. In addition, some of these inhibitors sometimes bind irreversibly, but when they do, they release a toxic leaving group. Thus, the end result often seen with these types of inhibitors is that, even though they help to ameliorate the disease in the early stages of administration, they ultimately lose most of these effects over time with potentially serious negative side-effects.

The compounds of this invention are directed to a unique new group of compounds with irreversible cysteine protease inhibitory activity, some of which have no leaving groups. Compounds of formula I, II, and IA possess in their structure a Michael acceptor (vinyl groups conjugated to electron withdrawing groups) which confers an irreversible inhibition against cysteine proteases. The molecules can range from 1 to 5 natural or non-natural amino acids and the electrophilic "war head" moieties (e.g, vinyl sulfone, vinyl ester) are attached most notably to aspartic acid although other natural or non-natural amino acids are also possible (see Z, n description).

Wannamaker et al. (WO 01/90063) discloses an ICE inhibitor prodrug for treating IL-1 mediated diseases. However, the prodrug lacks the electrophilic moieties of the compounds of the present invention.

Palmer et al. (U.S. Pat. Nos. 5,976,858 and 6,287,840) described irreversible cysteine protease inhibitors containing vinyl groups conjugated to electron withdrawing groups. Palmer has shown compounds capable to inhibit cathepsins (B, I, S); cruzain and glutathione. However, Palmer showed that his compounds had no activity against cysteine proteases when aspartic acid is used at P1 position (e.g, Asp vinyl sulfone) except in one single case where the activity was below the threshold value for being considered to have any significance by the authors (and was thus discarded for any further development by the authors). This is the opposite of what is observed with the compounds of the present invention.

Similarly, Ng et al. (Org. Biomol. Chem, 2008, 6, 844-847) developed a library of compounds including some vinylsulfone inhibitors to target caspase-3 and -7. However none of the vinylsulfone inhibitors showed potency against caspase-3 and only one molecule showed modest inhibitory activity against caspase-7 according to the authors.

Maria M. M. Santos et al. (European Journal of Med Chem: 46 (2011) 2141 and 45 (2010) 3858) have developed some non-selective aspartic acid vinyl sulfone derivatives with marginal potency. Due to the marginal potency in enzymatic assays, the authors believed that the potency observed was due to an indirect effect on caspase-3 inhibition.

Similarly, Nazif T et al. (EP 1863513, U.S. Pat. No. 7,589,066, PNAS: 2001, 98 (6), 2967-2972) described global analysis of proteasomal substrate specificity using positional-scanning libraries of covalent inhibitors. Nazif has shown compounds capable to inhibit selectively immunoproteasomes as compared to a constitutive proteasome (10-fold or greater). However, in addition to being selective immunoproteasome inhibitors, Nazif's compounds are apoptosis inducers. The compounds of the present invention are not selective immunoproteasome inhibitors and apoptosis inducers, and in many cases the compounds of the present invention are apoptosis inhibitors.

Given their role in several diseases and conditions, there is a need for compounds capable of selectively targeting either a specific caspase or a group of caspases or a cysteine protease. There is also a need for effective pharmaceutical compositions and methods of treatment for caspase-mediated diseases and cysteine protease-mediated diseases.

The present invention addresses these needs for novel compounds, therapies, new treatment methods, and pharmaceutical compositions.

Additional features of the invention will be apparent from review of the disclosure, tables and description of the invention below.

BRIEF SUMMARY OF THE INVENTION

The present invention relates to compounds according to any of Formula I, II, IA-VA, IVA1-IVA5, IIIA1-IIIA5 as defined herein, compositions thereof and methods for the prevention and/or treatment of cysteine protease-mediated diseases, such as caspase-mediated diseases in subjects. Particular aspects of the invention relates to use of compounds according to any of Formula I, II, IA-VA, IVA1-IVA5, IIIA1-IIIA5 as defined herein.

Compounds of formula I, II, IA-VA, IVA1-IVA5, IIIA1-IIIA5 target the Cysteine protease family. Caspases belong to the family of cysteine protease enzymes. In humans, caspases have been classified in two general groups according to their effects: proapoptotic (caspase-2, 3, 6, 7, 8, 9, 10) and proinflammatory (caspase-1, 4, 5, 11, 12) caspases. The proapoptotic caspases have been divided into initiators (caspase-2, 8, 9, 10) also known as group II, and executioners (caspase-3, 6, 7) of the apoptotic process or group III.

In some embodiments, compounds of Formula IVA inhibit one or more caspases of the proinflammatory caspase group (caspase-1, 4, 5, 11, 12) and include the following compounds

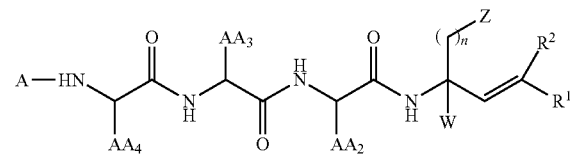

IVA wherein

AA$_2$ is the amino acid side chain of Pro, Val, Ala, Thr, Ile, or His;

AA$_3$ is the amino acid side chain of t-Leu, Glu, Gln, Asp, Ala, Gly, Thr, Val, Trp; or AA$_3$ is phenylglycine or indanylglycine; Trp(N-Me).

AA$_4$ is the amino acid side chain of Tyr, Trp, Phe, Val, or Asp;

and wherein A, R$^1$, R$^2$, Z, n, w are as defined hereinabove and hereinbelow.

In some embodiments, compounds of Formula IIIA inhibit one or more caspases of the proinflammatory caspases group (caspase-1, 4, 5, 11, 12) and include the following compounds

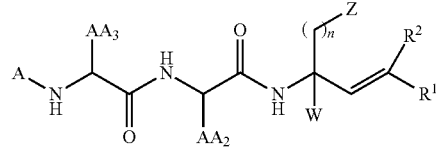

IIIA wherein

AA$_2$ is the amino acid side chain of Pro, 2-carbonyl Azetidine, Val, Ala, Thr, or His;

AA$_3$ is the amino acid side chain of t-Leu, CyclohexaneGlycine, CyclopropylGlycine, Glu, Gln, Asp, Ala, Gly, Thr, Val, Trp; or AA$_3$ is phenylglycine or indanylglycine;

and wherein A, R$^1$, R$^2$, Z, w, n are as defined hereinbelow.

In some embodiments, compounds of Formula IVA inhibit one or more caspases of the executioner caspases group (Caspase-3, 6, 7) and include the following compounds

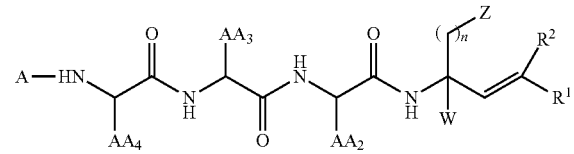

IVA wherein

AA$_2$ is the amino acid side chain of Val, 2-Azetidine; Leu, Phe, Ile, Pro, Met, Ala, Thr, His, Ser (O-phosphate), Thr (O-phosphate) (wherein the oxygen of the phosphate is free or protected).

AA$_3$ is the amino acid side chain of t-Leu, Trp, Tyr, Ala, Asp, Glu, Arg, modified Arg, Gln, Phe, Ser, Thr, Val, Tyr, Gly, Leu; or AA$_3$ is the amino acid side chain of 3-(1-naphtyl)-alanine, phenylglycine, indanylglycine, Ala-(2'-quinolyl), 2-pyridylAla or 4-methyl phenylalanine; N-Methyl Trp.

AA$_4$ is the amino acid side chain of Asp, Val, Thr, Leu.

and wherein A, R$^1$, R$^2$, Z, w and n are as defined hereinabove and hereinbelow.

In some embodiments, compounds of Formula IVA inhibit one or more caspases of the initiator caspase group consisting of Caspase 8, 9, and 10, and include the following compounds

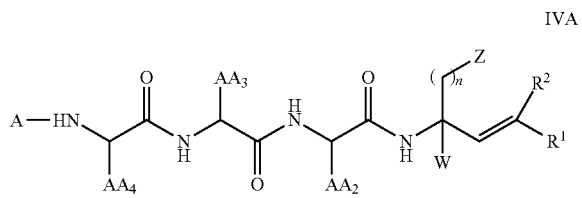

IVA wherein

AA$_2$ is the amino acid side chain of Pro, Tyr, Phe Thr, His, Val, Trp, Ile, 2-Azetidine, or Ala AA$_3$ is the amino acid side chain of t-Leu, Glu or AA$_3$ is Ala-(2'-quinolyl); Phenyl Glycine or Cyclopropyl Glycine.

AA$_4$ is the amino acid side chain of Trp, Ile, Leu, Glu, Asp, Ala, Pro, Val or 4-methyl phenylalanine;

and wherein A, R$^1$, R$^2$ and R$^4$, w, z and n are as defined hereinabove and hereinbelow.

In some embodiments, compounds of Formula IIIA inhibit one or more caspases of the initiator caspase group consisting of Caspase 8, 9, and 10, and include the following compounds

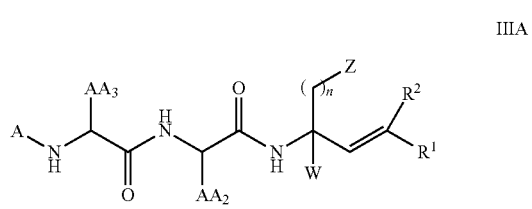

IIIA wherein

AA$_2$ is the amino acid side chain of Pro.

AA$_3$ is the amino acid side chain of t-Leu, and wherein A, R$^1$, R$^2$, Z, w, n are as defined hereinabove and hereinbelow.

In some embodiments, compounds of Formula VA inhibit caspase 2 and include the following compounds

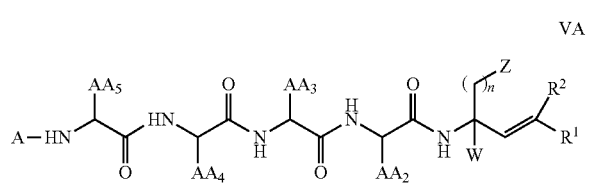

VA wherein

AA$_2$ is the amino acid side chain of Ala, Ser, Lys or Val;
AA$_3$ is the amino acid side chain of Val, Glu, Thr, or Gln;
AA$_4$ is the amino acid side chain of Asp, or Leu;
AA$_5$ is the amino acid side chain of Val or Leu;
and wherein A, R$^1$, R$^2$ and R$^4$, w, z and n are as defined hereinabove and hereinbelow.

One aspect of the invention concerns a method for preventing and/or treating a caspase-mediated disease in a subject in need thereof, comprising administering to said subject an effective amount of a compound represented by any of Formula I, II, IA-VA, IVA1-IVA5, IIIA1-IIIA5 as defined herein.

One aspect of the invention concerns the use of a compound represented by any of Formula I, II, IA-VA, IVA1-IVA5, IIIA1-IIIA5 defined herein for preventing and/or treating of a Cysteine Protease mediated disease in a subject in need thereof.

Another related aspect of the invention concerns the use of a compound represented by any of Formula I, II, IA-VA, IVA1-IVA5, IIIA1-IIIA5 as defined herein for the manufacture of a medication for preventing and/or treating of caspase-mediated diseases in a subject in need thereof.

An additional aspect of the invention concerns a compound a compound represented by any of Formula I, II, IA-VA, IVA1-IVA5, IIIA1-IIIA5 as defined herein for use in preventing and/or treating a caspase-mediated diseases in a subject in need thereof.

One aspect of the invention concerns a method of treating excessive apoptosis affected by cysteine protease and or caspase activity in a cell or a tissue, the method comprising: contacting the cell or tissue with an effective amount of one or more compounds represented by any of Formula I, II, IA-VA, IVA1-IVA5, IIIA1-IIIA5 as defined herein, so as to treat the excessive apoptosis.

One particular aspect of the invention concerns the use of a compound represented by any of Formula I, II, IA-VA, IVA1-IVA5, IIIA1-IIIA5 as defined herein for use in apoptosis-mediated diseases.

Specific examples of compounds are provided in Table 1.

The invention also concerns methods and strategies of targeting caspases. In one embodiment the approach consists of designing a suicide substrate leading to a permanent inhibition of the caspase. Preferably, the approach consists of designing a substrate that is recognizable enough for caspases, especially one or more specific caspase(s), to fit into it, to be potentially cleaved at a specific position in a way that makes the caspase enzyme irreversibly linked to the substrate thereby leading to a permanent inhibition of the caspase. In some embodiments, the suicide substrates of this invention are vinyl electron withdrawing group (EWG).

Further aspects of the invention will be apparent to a person skilled in the art from the following description, and claims and generalizations therein.

BRIEF DESCRIPTION OF THE TABLES

Table 1 provides examples of compounds of the present invention.

Table 2-4 lists the results of the measured activity of selected compounds on Caspase 1-10 enzymatic inhibition.

As shown in Table 2, compounds #105 and #26 exhibited high inhibitory activity towards the effector (executioner) Caspases: Caspase-3 and -7, but compound #105 also exhibited stronger inhibitory activity towards the pro-inflammatory caspases Caspase-1 and -4. Shorter peptide Vinyl sulfone (compound #6 and compound #14) and Ethyl Vinyl Ester (compound #118) exhibited very strong inhibitory activity towards pro-inflammatory Caspases while compound #14 and compound #118 still inhibits caspase initiator (Caspase-9). Compound #40 exhibited strong inhibitory activity towards pro-inflammatory Caspases: Caspase-1, -4, -5. Shorter peptide Vinyl Ester Compound 116 (versus compound 14 vinyl sulfone) exhibited stronger inhibitory activity towards pro-inflammatory caspases Caspase-1 and -5 with potency also against caspase-8. Compounds 123 (Z-Val-Glu-Ile-Asp-αchlorovinyl methyl vinyl sulfone) and 124 (Z-Val-Glu-Ile-Asp Ethyl Vinyl ester) exhibited inhibition against Caspase-6 (229 nM) and (293 nM) respectively. Compound 126 (Z-Val-Glu-Phe-Asp-Ethyl Vinyl ester) exhibited selective inhibition against both caspase initiators Caspase-8 (79 nM) and caspase-10 (2 nM). Compound 124 (Z-Val-Glu-Ile-Asp Ethyl Vinyl ester) is a pan-caspase inhibitor.

As shown in Table 3 hereinafter, monopeptide suicide substrates such as Asp αchlorovinyl methyl vinyl sulfone, Tosyl salt (Compound 4) showed inhibition against caspase-10 (43%) at 100 μM.

The di-peptide suicide substrates Z-Val-Asp αchlorovinyl methyl vinyl sulfone (Compound 2) showed inhibition against caspase-7 (60%), caspase-3 (39%), caspase-9 (66%), caspase-8 (49%) and caspase-10 (48%) at 100 μM.

Table 4 provides the % inhibition of these compounds at 100 μM.

DETAILED DESCRIPTION OF THE INVENTION

A) General Overview of the Invention

The present inventors have discovered compounds that have beneficial pharmaceutical properties and that these compounds may be effective for use in cysteine protease and or caspase-mediated diseases such as sepsis, myocardial infarction, cancer, inflammation, tissue atrophy, ischemia, ischemic stroke, spinal cord injury (SCI), traumatic brain injury (TBI) and neurodegenerative disease (e.g. multiple sclerosis (MS), ALS, Alzheimer's, Parkinson's, and Huntington's diseases).

B) Compounds of the Invention

Broadly speaking, the invention concerns a compound represented by Formula I

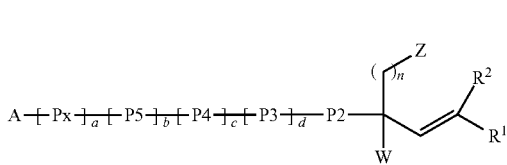

I wherein A, PX, P5, P4, P3, P2, $R^1$, $R^2$, a, b, c, d, z, w, and n are as defined hereinabove and hereinbelow;

or a prodrug, or a pharmaceutically acceptable salt to allow the drug to penetrate the cell membrane or the compound is labeled with a detectable label or an affinity tag thereof.

The line "-" when located between P2, P3, P4, P5 and PX represents a peptide bond or a peptidomimetic bond; The PX, P5, P4, P3, P2 amino acid residues are normally linked via a peptide bond, that is, a peptidic carbamoyl group, i.e. —CONH—. However, peptidomimetic bonds are also contemplated, such as $CH_2$—NH, CO—$CH_2$, azapeptide and retro-inverso bonds.

Residues PX, P5, P4, P3, P2 are natural and non-natural amino acid residues as defined herein.

The $R^1$ and $R^2$ that are bonded to the vinyl group can be either in the cis configuration or the trans configuration, as represented by the wavy lines. In one example, $R^1$ is configured to be trans such that the electron withdrawing capability of the $R^1$ group is stabilized. n is 0-3.

Z is H, $COR_4$; $COR^9$; CN; $OR^9$; $OCOR^9$, $OCO_2R^9$.NO, $NO_2$, $NR^7R^8$, $NCOR^9$, $SCOR^9$, $^+NR^7R^8$ $R^9$.$NHSO_2R^9$, $NHCOR^9$.$SO_2R^9$, $SOR^9$, $SR^9$, halogen.

Z is amino acid side chain, or heterocycles saturated and or unsaturated as indicated below where $x_1$-$x_6$ could be carbone or heteroatoms such N, O, S. As examples of heterocycles are Tetrazole derivatives.

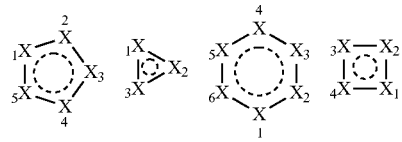

W is H, alkyl, OH; $OR^9$; $NH_2$; NH $R^9$; $NHSOR^9$, halogen, $COR^4$; CN; $OCOR^9$, $OCO_2R^9$.NO, $NO_2$, $NR^7R^8$, $NHSO_2R^9$, $NHCOR^9$.$SO_2R^9$, $SOR^9$, $SR^9$.

Broadly speaking, the invention concerns a compound represented by Formula II

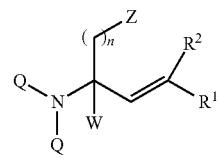

II wherein $R^1$, $R^2$, z, w, Q, and n are as defined hereinabove and hereinbelow;

or a prodrug, or a pharmaceutically acceptable salt to allow the drug to penetrate the cell membrane or the compound is labeled with a detectable label or an affinity tag thereof.

The $R^1$ and $R^2$ that are bonded to the vinyl group can be either in the cis configuration or the trans configuration, as represented by the wavy lines. In one example, $R^1$ is configured to be trans such that the electron withdrawing capability of the $R^1$ group is stabilized. n is 0-3.

Z is H, $COR_4$; $COR_5$, CN; $OR^9$; $OCOR^9$, $OCO_2R^9$.NO, $NO_2$, $NR^7R^8$, $^+NR^7R^8$ $R^9$.$NHSO_2R^9$, $NCOR^9$, $SCOR^9$, $NHCOR^9$.$SO_2R^9$, $SOR^9$, $SR^9$, halogen.

Z is amino acid side chain, or heterocycles saturated and or unsaturated as indicated below where $x_1$-$x_6$ could be carbone or heteroatoms such N, O, S. As examples of heterocycles are Tetrazole derivatives.

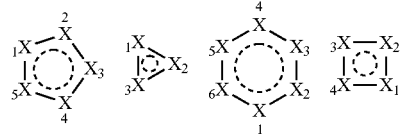

W is H, alkyl, OH; $OR^9$; $NH_2$; NH $R^9$; $NHSOR^9$, halogen, $COR^4$; CN; $OCOR^9$, $OCO_2R^9$.NO, $NO_2$, $NR^7R^8$, $NHSO_2R^9$, $NHCOR^9$.$SO_2R^9$, $SOR^9$, $SR^9$ Q is selected from H, $SO_2R^9$, SOR9, CORc, COCORC, Rc, (Rc are alkyl, substituted alkyl, heteroalkyl, heteroaryl, aryl, alkyl aryl derivatives, cycloalkyl, substituted cycloalkyl, (cycloalkyl)alkyl, saturated and or unsaturated heterocycle, phenyl, substituted phenyl, phenyl alkyl, substituted phenyl alkyl, hetero alkyl, naphtyl, substituted naphtyl, (1 or 2 naphthyl) alkyl, substituted (1 or 2 naphthyl) alkyl, (heterocycle) alkyl, substituted (heterocyclic)alkyl).

Further included within the scope of the invention are compounds of Formula IA:

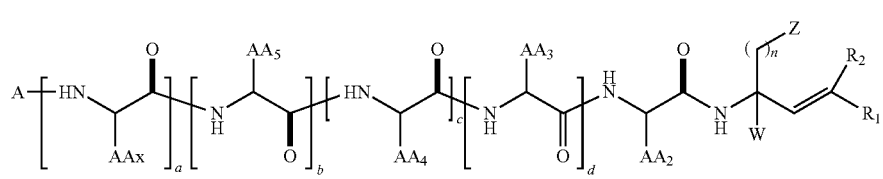

wherein A, $AA_X$, $AA_5$, $AA_4$, $AA_3$, $AA_2$, $R^1$, $R^2$, a, b, c, d, z, w, and n are as defined hereinabove and hereinbelow;

or a prodrug, or a pharmaceutically acceptable salt to allow the drug to penetrate the cell membrane, or the compound is labeled with a detectable label or an affinity tag thereof.

Thus, when a, b, c and d are 0, the present invention includes compounds of Formula IIA:

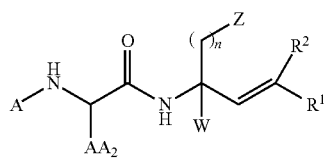

wherein A, $AA_2$, $R^1$, $R^2$, z, n, and w are as defined hereinabove and hereinbelow.

Thus, when a, b and c are 0, the present invention includes compounds of Formula IIIA:

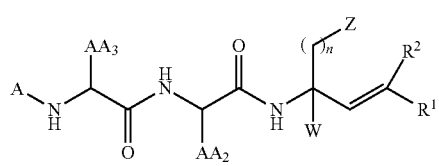

wherein A, $AA_3$, $AA_2$, $R^1$, $R^2$, z, n, and w are as defined hereinabove and hereinbelow.

Thus, when a and b are both 0, the present invention includes compounds of Formula IVA:

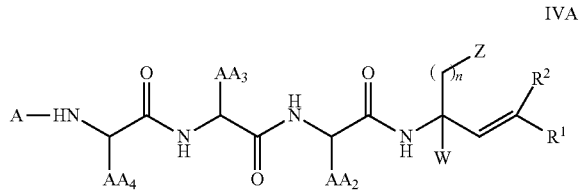

wherein A, $AA_4$, $AA_3$, $AA_2$, $R^1$, $R^2$, z, w and n are as defined hereinabove and hereinbelow.

Furthermore, when a is 0 and b is 1, the present invention includes compounds of Formula VA

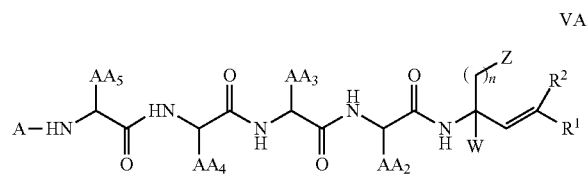

wherein A, $AA_5$, $AA_4$, $AA_3$, $AA_2$, $R^1$, $R^2$, z, w and n are as defined hereinabove and hereinbelow.

One subset of compounds of Formula IVA includes compounds of Formula IVA1:

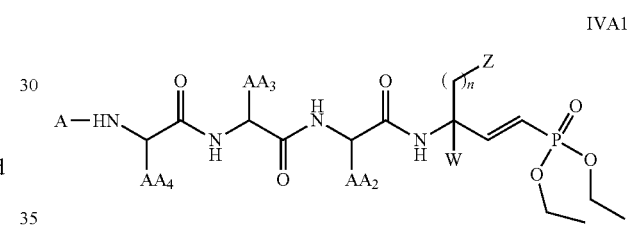

wherein A, $AA_4$, $AA_3$, $AA_2$, $R^1$, $R^2$, z, w and n are as defined hereinabove and hereinbelow.

One subset of compounds of Formula IVA includes compounds of Formula IVA2:

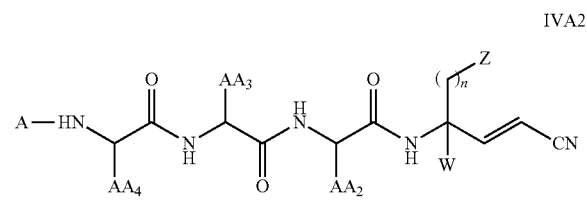

wherein A, $AA_4$, $AA_3$, $AA_2$, $R^1$, $R^2$, z, w and n are define hereinabove and hereinbelow.

One subset of compounds of Formula IVA includes compounds of Formula IVA3:

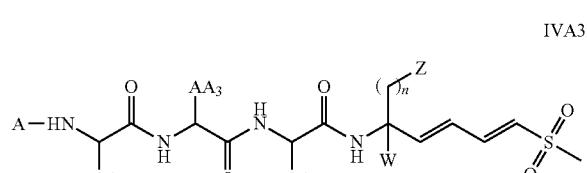

wherein A, $AA_4$, $AA_3$, $AA_2$, $R^1$, $R^2$, z, w and n are as defined hereinabove and hereinbelow.

One subset of compounds of Formula IVA includes compounds of Formula IVA4:

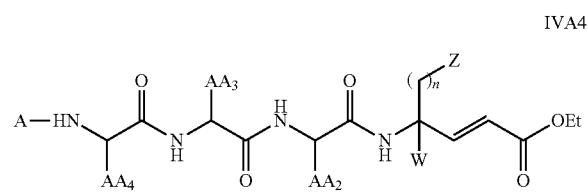

IVA4 wherein A, AA$_4$, AA$_3$, AA$_2$, R$^1$, R$^2$, z, w and n are as define hereinabove an hereinbelow.

One subset of compounds of Formula IVA includes compounds of Formula IVA5:

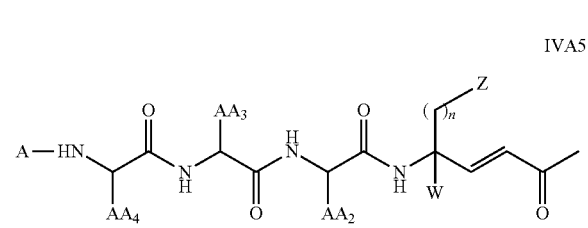

IVA5 wherein A, AA$_4$, AA$_3$, AA$_2$, R$^1$, R$^2$, w and n are as defined hereinabove and hereinbelow, or a prodrug, or a pharmaceutically acceptable salt to allow the drug to penetrate the cell membrane, or the compound is labeled with a detectable label or an affinity tag thereof.

One subset of compounds of Formula IIIA includes compounds of Formula IIIA1:

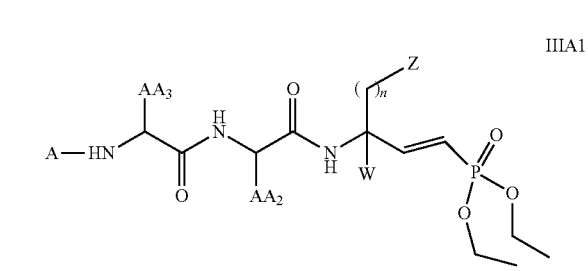

IIIA1 wherein A, AA$_3$, AA$_2$, R$^1$, R$^2$, z, w and n are as defined hereinabove an hereinbelow.

One subset of compounds of Formula IIIA includes compounds of Formula IIIA2:

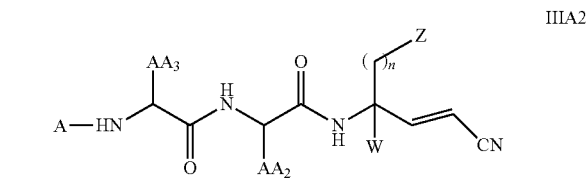

IIIA2 wherein A, AA$_3$, AA$_2$, R$^1$, R$^2$, z, w and n are as defined hereinabove an hereinbelow.

One subset of compounds of Formula IIIA includes compounds of Formula IIIA3:

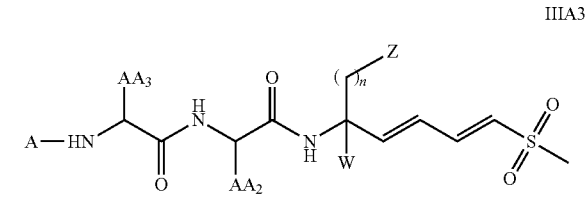

IIIA3 wherein A, AA$_3$, AA$_2$, R$^1$, R$^2$, z, w and n are as defined hereinabove and hereinbelow.

One subset of compounds of Formula IIIA includes compounds of Formula IIIA4:

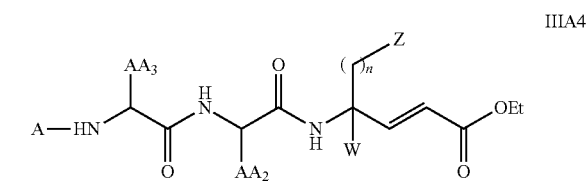

IIIA4 wherein A, AA$_3$, AA$_2$, R$^1$, R$^2$, z, w and n are as defined hereinabove an hereinbelow.

One subset of compounds of Formula IIIA includes compounds of Formula IIIA5:

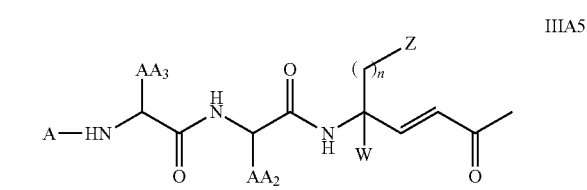

IIIA5 wherein A, AA$_3$, AA$_2$, R$^1$, R$^2$, z, w and n are as defined hereinabove and hereinbelow, or a prodrug, or a pharmaceutically acceptable salt to allow the drug to penetrate the cell membrane, or the compound is labeled with a detectable label or an affinity tag thereof.

A, b, c and d:

In one subset of compounds, a is 0 or 1; and b is 0 or 1 provided that when b is 0, a is 0.

In another example, a is 0 and b is 1.

In one example, a and b are both 0.

In one example, a, b, c are all 0.

In one example, a, b, c, d, are all 0.

Any and each individual definition of a, b, c, d as set out herein may be combined with any and each individual definition of AA$_x$, AA$_2$, AA$_3$ and AA$_4$, A, R$^1$, R$^2$, z, w and n as set out herein.

A:

In one subset, A is
1) H,
2) $C_1$-$C_6$ alkyl,
3) aryl,
4) heteroaryl,
5) heterocyclyl,
6) R$^3$—C(O)—,
7) R$^3$—OC(O)—, 8) $R^3$—$CH_2OC(O)$—,
9) $R^3$—$C(O)O$—, or
10) $R^3$—$S(O)_2$—.

In one example, A is H.
In one example, A is $R^3$—$CH_2OC(O)$—.
In one example, A is $PhCH_2OC(O)$—.
In one example, A is Quinoline-$C(O)$—.
In one example, A is (4-Amino-3-Chloro-benzene)-$C(O)$—.

Any and each individual definition of A as set out herein may be combined with any and each individual definition of $AA_x$, $AA_2$, $AA_3$ and $AA_4$, a, b, $R^1$, $R^2$ and $R^4$ as set out herein.

$R^1$:
In one subset, $R^1$ is an electron withdrawing group (EWG) selected from:
1) aryl,
2) heteroaryl,
3) heterocyclyl,
4) $C_2$-$C_6$ alkene-$R^{20}$,
5) $SO_2R^5$,
6) $SO_3R^5$,
7) $SOR^5$,
8) $SONHR^5$,
9) $SO_2NHR^5$,
10) CN,
11) $CO_2R^5$,
12) $COR^5$,
13) $PO_3R^5$,
14) $PO(OR^5)_2$, or
15) $PO(OR^5)$,
wherein the aryl, the heteroaryl, or the heterocyclyl are optionally substituted with one or more $R^{30}$.

In one example, $R^1$ is in the trans configuration.
In one example, $R^1$ is $SO_2R^5$, wherein $R^5$ is $C_1$-$C_6$ alkyl.
Any and each individual definition of $R^1$ as set out herein may be combined with any and each individual definition of $AA_2$, $AA_3$ and $AA_4$, A, a, b, $R^2$ and $R^4$ as set out herein.

$R^2$:
In one subset, $R^2$ is
1) $R^1$; or
2) H,
3) halogen,
4) haloalkyl,
5) $C_1$-$C_6$ alkyl,
6) $C_2$-$C_6$ alkene,
7) $C_3$-$C_7$ cycloalkyl,
8) $OR^9$,
9) $SR^9$,
10) $N^+(R^4)_3$,
10) $OCOR^6$,
11) $OCO_2R^6$,
12) $NR^7R^8$,
13) $NHSO_2R^6$,
14) $NHCOR^6$,
15) aryl,
16) heteroaryl, or
17) heterocyclyl;
wherein $R^1$, $R^6$, $R^7$, $R^8$ and $R^9$ are as defined hereinabove and hereinbelow.

In one example, $R^2$ is H.
In another example, $R^2$ is halogen.
In yet another example, $R^2$ is Cl.
Any and each individual definition of $R^2$ as set out herein may be combined with any and each individual definition of $AA_x$, $AA_2$, $AA_3$ and $AA_4$, A, a, b, $R^1$ and $R^4$ as set out herein.

$R^3$:
In one subset, $R^3$ is
1) $C_1$-$C_6$ alkyl,
2) aryl-$C_1$-$C_6$ alkyl,
3) heteroaryl, or
4) heterocyclyl.

Any and each individual definition of $R^3$ as set out herein may be combined with any and each individual definition of $AA_x$, $AA_2$, $AA_3$ and $AA_4$, A, a, b, $R^1$, $R^2$ and $R^4$ as set out herein.

$R^4$:
In one subset, $R^4$ is
1) OH,
2) $OC_1$-$C_6$ alkyl,
3) $NR^7R^8$, or
4) $NHSO_2R^9$.
5) Alkyl, heteroalkyl.
In one example, $R^4$ is OH or $OC_1$-$C_6$ alkyl.
In one example, $R^4$ is OH, $OCH_3$, $OCH_2CH_3$, $OCH_2CH_2CH_3$, or $OC(CH_3)_3$.

Any and each individual definition of $R^4$ as set out herein may be combined with any and each individual definition of $AA_x$, $AA_2$, $AA_3$ and $AA_4$, A, a, b, $R^1$ and $R^2$ as set out herein.

$R^5$:
In one subset, $R^5$ is
1) H,
2) $C_1$-$C_6$ alkyl,
3) $C_2$-$C_6$ alkene,
4) $C_3$-$C_7$ cycloalkyl,
5) haloalkyl,
6) aryl,
7) heteroaryl,
8) heterocyclyl,
9) $NHCH_2C(O)OH$, or
10) (D) or (L) natural or non-natural amino acid derivatives optionally protected with an amino acid protecting group.

Examples of amino acid protecting groups are known to those skilled in the art and include, for example, tert-butyl, benzoyl, methyl and the like.

Any and each individual definition of $R^5$ as set out herein may be combined with any and each individual definition of $AA_x$, $AA_2$, $AA_3$ and $AA_4$, A, a, b, $R^1$, $R^2$ and $R^4$ as set out herein.

$R^6$:
In one subset, $R^6$ is
11) any (D) or (L) amino acid residue,
2) $C_1$-$C_6$ alkyl,
3) $C_3$-$C_7$ cycloalkyl,
4) aryl,
5) heteroaryl, or
6) heterocyclyl,
in which the alkyl or the cycloalkyl are optionally substituted with one or more $R^{10}$ substituents; and in which the aryl, heteroaryl or heterocyclyl are optionally substituted with one or more $R^{20}$ substituents.

Any and each individual definition of $R^6$ as set out herein may be combined with any and each individual definition of $AA_x$, $AA_2$, $AA_3$ and $AA_4$, A, a, b, $R^1$, $R^2$ and $R^4$ as set out herein.

$R^7$ and $R^8$:
In one subset, $R^7$ and $R^8$ are independently selected from:
1) H,
2) $C_1$-$C_6$ alkyl,
3) $C_3$-$C_7$ cycloalkyl,
4) haloalkyl, 5) aryl,
6) heteroaryl, or
7) heterocyclyl,
wherein the alkyl and the cycloalkyl are optionally substituted with one or more $R^{10}$ substituents, and the aryl, the heteroaryl and the heterocyclyl are optionally substituted with one or more $R^{20}$ substituents.

Any and each individual definition of $R^7$ and $R^8$ as set out herein may be combined with any and each individual definition of $AA_x$, $AA_2$, $AA_3$ and $AA_4$, A, a, b, $R^1$, $R^2$ and $R^4$ as set out herein.

$R^9$:
In one subset, $R^9$ is
1) H,
2) $C_1$-$C_6$ alkyl,
3) $C_3$-$C_7$ cycloalkyl,
4) aryl,
5) heteroaryl, or
6) heterocyclyl,
in which the alkyl or the cycloalkyl are optionally substituted with one or more $R^{10}$ substituents; and in which the aryl, heteroaryl or heterocyclyl are optionally substituted with one or more $R^{20}$ substituents.

Any and each individual definition of $R^9$ as set out herein may be combined with any and each individual definition of $AA_x$, $AA_2$, $AA_3$ and $AA_4$, A, a, b, $R^1$, $R^2$ and $R^4$ as set out herein.

$R^{10}$:
In one subset, $R^{10}$ is independently selected from:
1) halogen,
2) $C_1$-$C_6$ alkyl,
3) $C_3$-$C_7$ cycloalkyl,
4) haloalkyl,
5) aryl,
6) heteroaryl,
7) heterocyclyl,
8) $OR^9$,
9) $S(O)_m R^9$,
10) $NR^7 R^8$,
11) $COR^9$,
12) $C(O)OR^9$,
13) $OC(O)R^9$,
14) $SC(O)R^9$,
15) $CONR^7 R^8$, or
16) $S(O)_2 NR^7 R^8$,
wherein m is an integer of 0, 1, or 2, wherein $R^7$, $R^8$ and $R^9$ are as defined hereinabove and hereinbelow.

Any and each individual definition of $R^{10}$ as set out herein may be combined with any and each individual definition of $AA_x$, $AA_2$, $AA_3$ and $AA_4$, A, a, b, $R^1$, $R^2$ and $R^4$ as set out herein.

$R^{20}$:
In one subset, $R^{20}$ is independently selected from:
1) halogen,
2) $NO_2$,
3) CN,
4) $C_1$-$C_6$ alkyl,
5) haloalkyl,
6) $C_3$-$C_7$ cycloalkyl,
7) $OR^7$,
8) $NR^7 R^8$,
9) $SR^7$,
10) aryl,
11) heteroaryl,
12) heterocyclyl,
13) $SO_2 R^5$,
14) $SO_3 R^5$,
15) $SOR^5$,
16) $SONHR^5$,
17) $SO_2 NHR^5$,
18) $PO_3 R^5$,
19) $PO(OR^5)_2$,
20) $PO(OR^5)$,
21) $COR^5$,
22) $COR^7$,
23) $CO_2 R^7$,
24) $S(O)_m R^7$,
25) $CONR^7 R^8$, or
26) $S(O)_2 NR^7 R^8$,
wherein the alkyl and the cycloalkyl are optionally substituted with one or more $R^6$ substituents; and wherein the aryl, the heteroaryl, or the heterocyclyl are optionally substituted with one or more $R^{30}$; wherein m is an integer of 0, 1, or 2;
wherein $R^7$, $R^8$ and m are as defined hereinabove and hereinbelow.

Any and each individual definition of $R^{20}$ as set out herein may be combined with any and each individual definition of $AA_x$, $AA_2$, $AA_3$ and $AA_4$, A, a, b, $R^1$, $R^2$ and $R^4$ as set out herein.

$R^{30}$:
In one subset, $R^{30}$ is
1) $NO_2$,
2) $C_2$-$C_6$ alkene-$R^{20}$,
3) $SO_2 R^5$,
4) $SOR^5$,
5) $SONHR^5$,
6) $SO_2 NHR^5$,
7) CN,
8) $CO_2 R^5$,
9) $COR^5$,
10) $PO_3 R^5$,
11) $PO(OR^5)_2$, or
12) $PO(OR^5)$;
wherein $R^5$ and $R^{20}$ are as defined hereinabove and hereinbelow.

Any and each individual definition of $R^{30}$ as set out herein may be combined with any and each individual definition of $AA_x$, $AA_2$, $AA_3$ and $AA_4$, A, a, b, $R^1$, $R^2$ and $R^4$ as set out herein.

Caspase 3 Inhibitors

The present invention includes compounds of Formula IVA:

IVA wherein
$AA_2$ is the amino acid side chain of Val, 2-Azetidine; Leu, Pro, Met, Ala, Thr, His, Ser (O-phosphate), Thr (O-phosphate) (wherein the oxygen of the phosphate is free or protected).

$AA_3$ is the amino acid side chain of t-Leu, Trp, Tyr, Ala, Asp, Glu, Gln, Phe, Ser, Thr, Val, Tyr, Gly, Leu; or $AA_3$ is the amino acid side chain of 3-(1-naphtyl)-alanine, phenylglycine, indanylglycine, Ala-(2'-quinolyl), 2-pyridylAla or 4-methyl phenylalanine; N-Methyl Trp.

AA$_4$ is the amino acid side chain of Asp;

and wherein A, R$^1$, R$^2$, Z, w and n are as defined hereinabove and hereinbelow.

Caspase 8/Caspase 9 Inhibitors

The present invention includes compounds of Formula IVA:

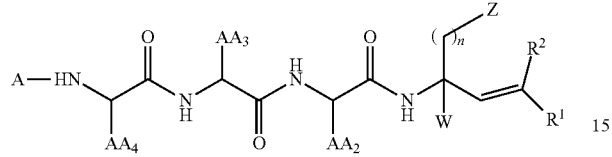

wherein

AA$_2$ is the amino acid side chain of Pro, Phe, Tyr, Thr, His, Val, Trp, Ile, 2-Azetidine, or Ala AA$_3$ is the amino acid side chain of t-Leu, Glu or AA$_3$ is Ala-(2'-quinolyl);

AA$_4$ is the amino acid side chain of Trp, Ile, Leu, Glu, Asp, Ala, Pro, Val or 4-methyl phenylalanine;

and wherein A, R$^1$, R$^2$ and R$^4$, w, z and n are as defined hereinabove and hereinbelow.

The present invention includes compounds of Formula IIIA (caspase 8/9 inhibitors)

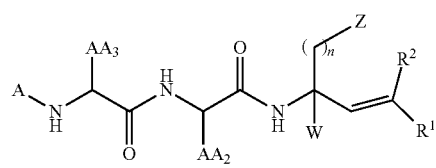

wherein

AA$_2$ is the amino acid side chain of Pro.

AA$_3$ is the amino acid side chain of t-Leu, and wherein A, R$^1$, R$^2$, Z, w, n are as defined hereinabove and hereinbelow.

Caspase 10 Inhibitors

The present invention includes compounds of Formula IVA:

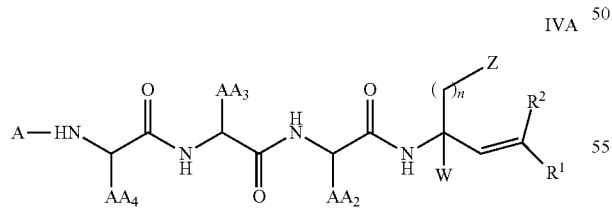

wherein

AA$_2$ is the amino acid side chain of Pro, Phe, Val, Ile, 2-Azetidine.

AA$_3$ is the amino acid side chain of t-Leu, Glu or AA$_3$ is phenyl Glycine or Cyclopropyl Glycine.

AA$_4$ is the amino acid side chain of Asp, Val and wherein A, R$^1$, R$^2$ and R$^4$, w, z and n are as defined hereinabove and hereinbelow.

The present invention includes compounds of Formula IIIA (caspase 10 inhibitors)

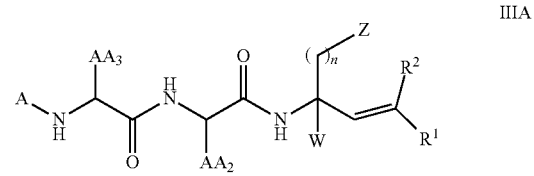

wherein

AA$_2$ is the amino acid side chain of Pro.

AA$_3$ is the amino acid side chain of t-Leu, and wherein A, R$^1$, R$^2$, Z, w, n are as defined hereinabove and hereinbelow.

Caspase 2 Inhibitors

The present invention includes compounds of Formula VA

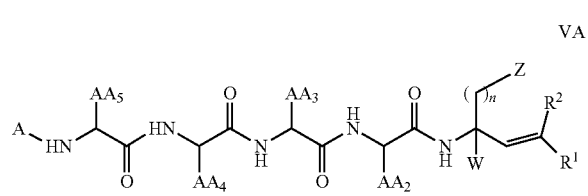

wherein

AA$_2$ is the amino acid side chain of Ala, Ser, Lys or Val;

AA$_3$ is the amino acid side chain of Val, Glu, Thr, or Gln;

AA$_4$ is the amino acid side chain of Asp, or Leu;

AA$_5$ is the amino acid side chain of Val or Leu;

and wherein A, R$^1$, R$^2$ and R$^4$, w, z and n are as defined hereinabove and hereinbelow.

Caspase 6 Inhibitors

The present invention includes compounds of Formula IVA (caspase 6 inhibitors)

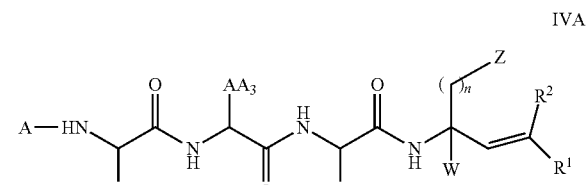

wherein

AA$_2$ is the amino acid side chain of Pro, Val, Ile, tLeu, Phg, Ala, Thr, or His.

AA$_3$ is the amino acid side chain of Glu, Gln, Asp, Arg, modified Arg.

AA$_4$ is the amino acid side chain of Asp, tLeu, Val, Thr, Ile.

and wherein A, R$^1$, R$^2$, Z, n, w are as defined hereinabove and hereinbelow.

The present invention includes compounds of Formula IIIA (caspase 6 inhibitors)

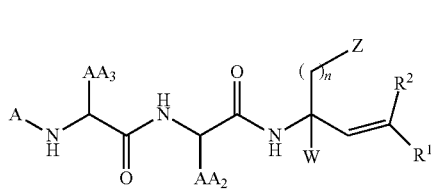

wherein

AA$_2$ is the amino acid side chain of Pro, 2-carbonyl Azetidine, Val, Ala, Thr, Pro, Ile, tLeu, Phg, or His.

AA$_3$ is the amino acid side chain of Glu, Gln, Asp, Arg, modified Arg;

and wherein A, R$^1$, R$^2$, Z, w, n are as defined hereinabove and hereinbelow.

Caspase 1/4/5 Inhibitors

The present invention includes compounds of Formula IVA (caspase 1 inhibitors)

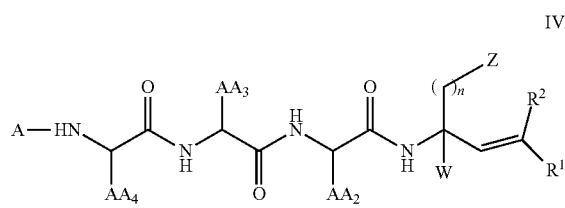

wherein

AA$_2$ is the amino acid side chain of Pro, Val, Ala, Thr, Ile, or His;

AA$_3$ is the amino acid side chain of t-Leu, Glu, Gln, Asp, Ala, Gly, Thr, Val, Trp; or AA$_3$ is phenylglycine or indanylglycine; Trp(N-Me).

AA$_4$ is the amino acid side chain of Tyr, Trp, Phe, Val, or Asp;

and wherein A, R$^1$, R$^2$, Z, n, w are as defined hereinabove and hereinbelow.

The present invention includes compounds of Formula IIIA (caspase 1/4/5 inhibitors)

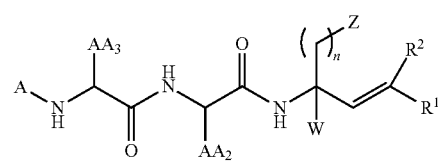

wherein

AA$_2$ is the amino acid side chain of Pro, 2-carbonyl Azetidine, Val, Ala, Thr, or His;

AA$_3$ is the amino acid side chain of t-Leu, CyclohexaneGlycine, CyclopropylGlycine, Glu, Gln, Asp, Ala, Gly, Thr, Val, Trp; or AA$_3$ is phenylglycine or indanylglycine;

and wherein A, R$^1$, R$^2$, Z, w, n are as defined hereinabove and hereinbelow.

One subset of compounds of Formula IIIA includes compounds of Formula IIIA 2a:

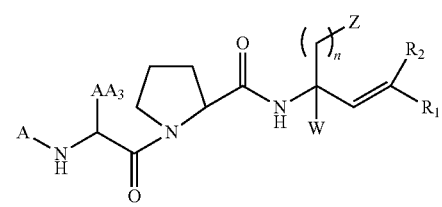

wherein

AA$_3$ is the amino acid side chain of t-Leu, CyclohexaneGlycine, CyclopropylGlycine, Glu, Gln, Asp, Ala, Gly, Thr, Val, Trp; or AA$_3$ is phenylglycine, Ala-(2'-quinolyl); or indanylglycine;

and wherein A, R$^1$, R$^2$, Z, w, n are as defined hereinabove and hereinbelow.

Compounds and intermediate compounds synthesized include those in Table 1:

TABLE 1

| CPD NO./CPD NAME/STRUCTURE |
| --- |
| 1. Cbz-Val-Asp(O-tBu) αchlorovinyl methyl vinyl sulfone |

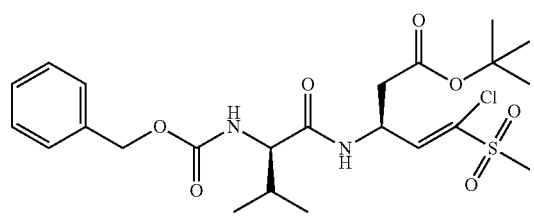

TABLE 1-continued
CPD NO./CPD NAME/STRUCTURE
2. Z-Val-Asp αchlorovinyl methyl vinyl sulfone
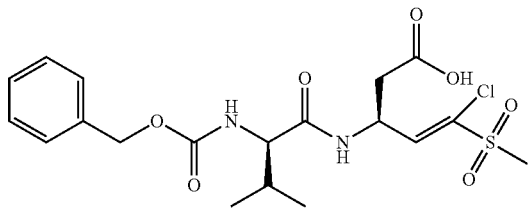
3. Z-Val-Asp methyl vinyl sulfone
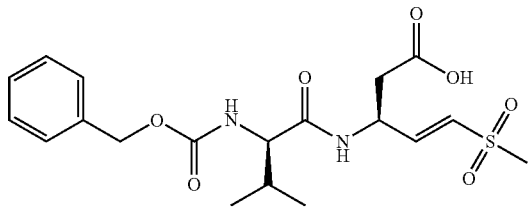
4. Asp αchlorovinyl methyl vinyl sulfone, Tosyl salt
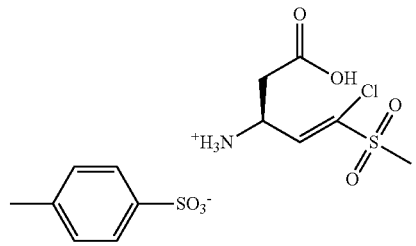
5. 2-Quinoline carbonyl-t-Leu-Pro-Asp(O-tBu)methyl vinyl sulfone
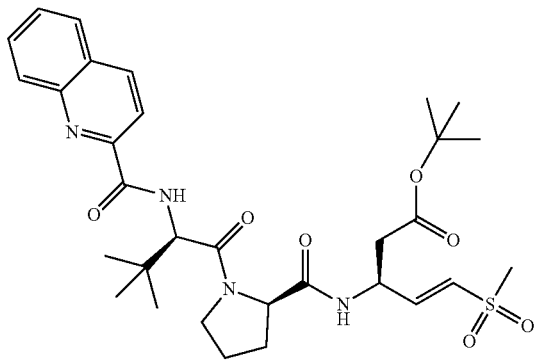

TABLE 1-continued
CPD NO./CPD NAME/STRUCTURE
6. 2-Quinoline carbonyl-t-Leu-Pro-Asp methyl vinyl sulfone
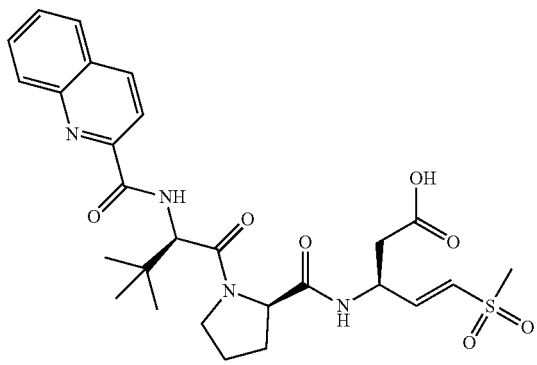
7. (1,5-Naphthyridine-2-carbonyl)-t-Leu-Pro-Asp(O-tBu)methyl vinyl sulfone
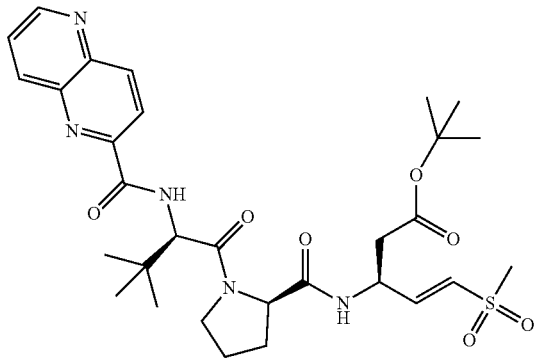
8. (1,5-Naphthyridine-2-carbonyl)-t-Leu-Pro-Asp methyl vinyl sulfone
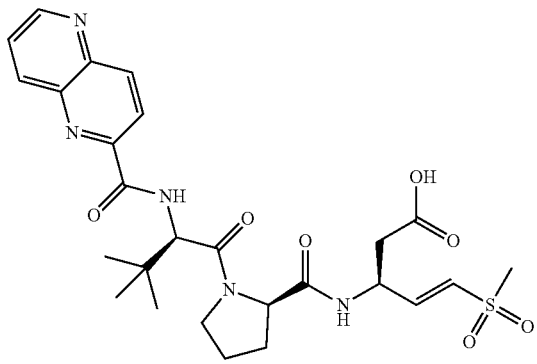

TABLE 1-continued
CPD NO./CPD NAME/STRUCTURE
9. Quinoline-6-carbonyl-t-Leu-Pro-Asp(O-tBu)methyl vinyl sulfone
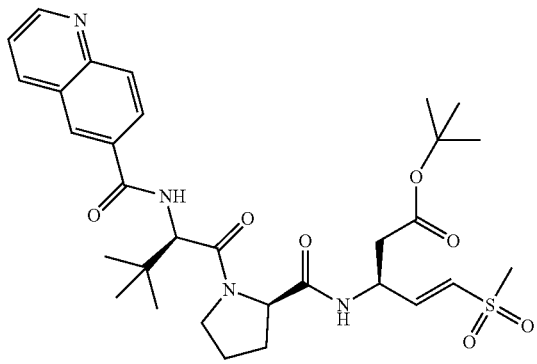
10. Quinoline-6-carbonyl-t-Leu-Pro-Asp methyl vinyl sulfone
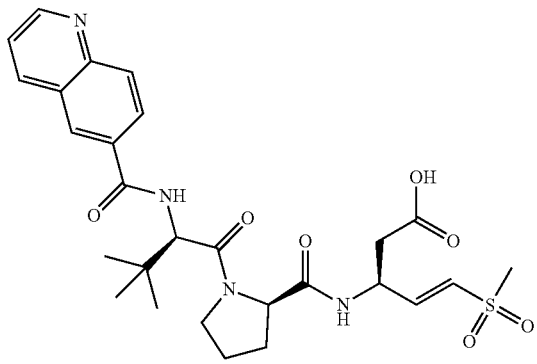
11. t-Leu-Allyl azetidine-2-carboxylate TFA salt
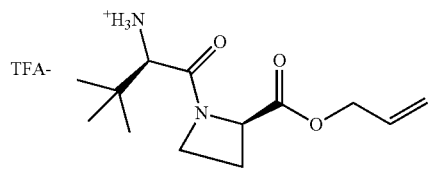

TABLE 1-continued
CPD NO./CPD NAME/STRUCTURE
12. 2-Quinoline carbonyl-t-Leu-Allyl Azetidine-2-carboxylate
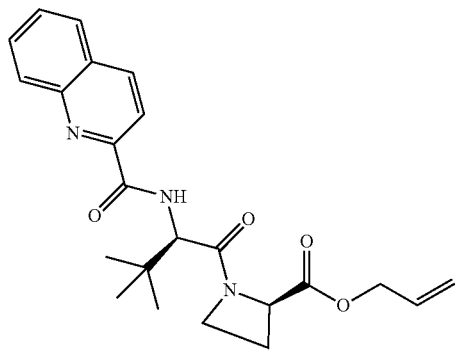
13. (4-((tert-butoxycarbonyl)amino)-3-chlorobenzene carbonyl)-t-Leu-Pro-Asp methyl vinyl sulfone
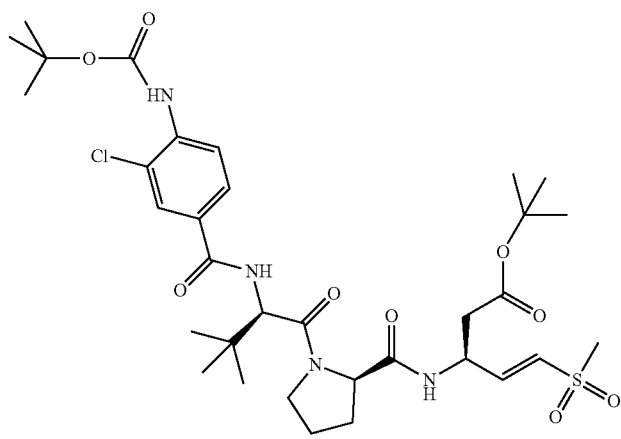
14. 4-amino-3-chlorobenzene carbonyl-t-Leu-Pro-Asp methyl vinyl sulfone
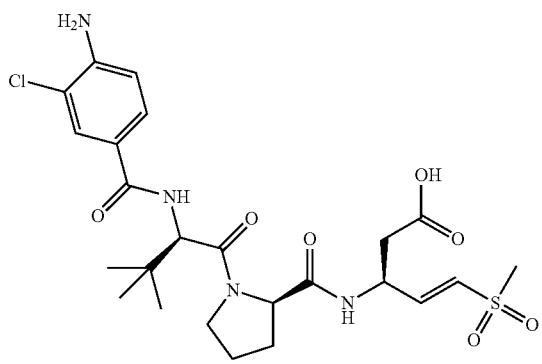

TABLE 1-continued
| CPD NO./CPD NAME/STRUCTURE |
|---|
15. 2-Quinoline carbonyl-Val-Asp(O-tBu)methyl vinyl sulfone
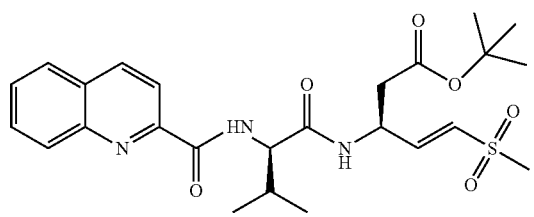
16. 2-Quinoline carbonyl-Val-Asp methyl vinyl sulfone
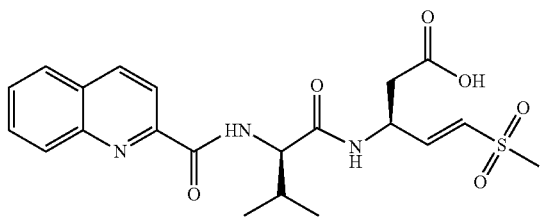
17. 2-Quinoline carbonyl-Glu(O-tBu)-Asp(O-tBu)methyl vinyl sulfone
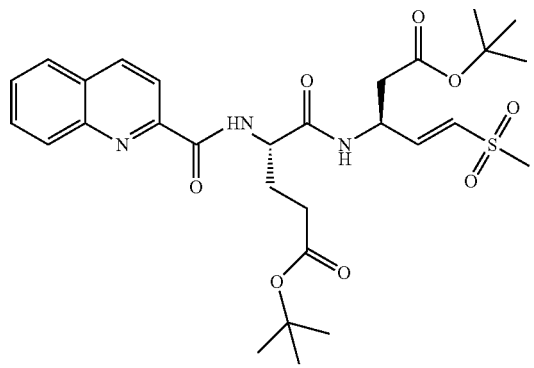
18. 2-Quinoline carbonyl-Glu-Asp methyl vinyl sulfone
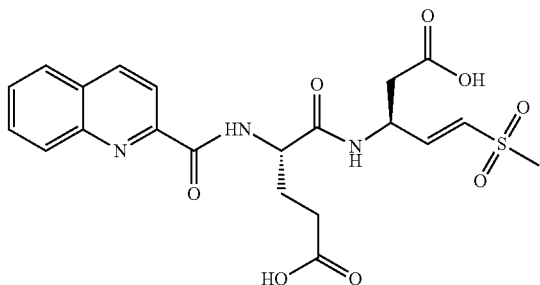

| CPD NO./CPD NAME/STRUCTURE |
|---|
| 19. 2-Quinoline carbonyl-t-Leu-(Azetidine-2-carbonyl)- Asp(O-tBu)methyl vinyl sulfone 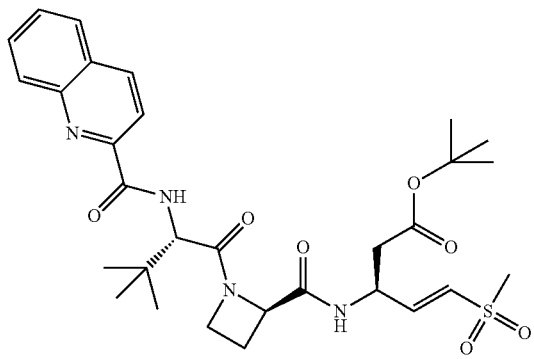 |
| 20. 2-Quinoline carbonyl-t-Leu-(Azetidine-2-carbonyl)- Asp methyl vinyl sulfone. 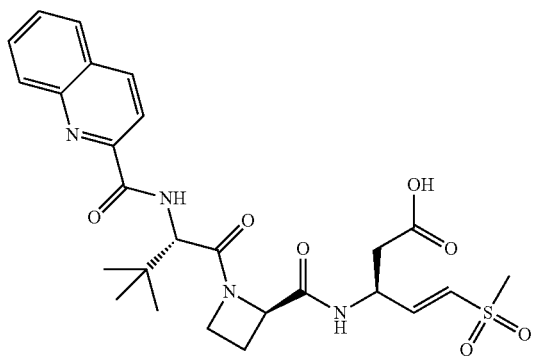 |
| 21. Boc-Glu(O-tBu)-Asp (O-tBu)- methyl vinyl sulfone. 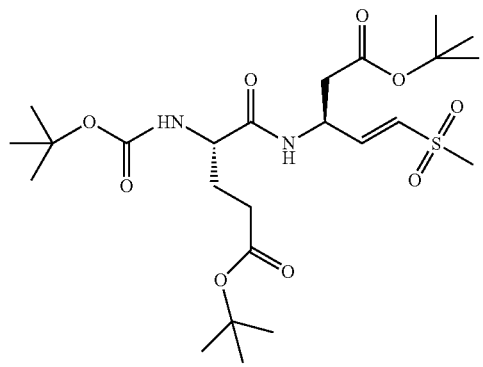 |

TABLE 1-continued
CPD NO./CPD NAME/STRUCTURE
22. Glu-Asp methylsulfone.
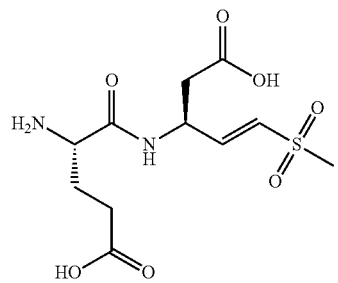
23. (2-Pyrrolidinone-5-carbonyl)- Asp(O-tBu)methyl vinyl sulfone
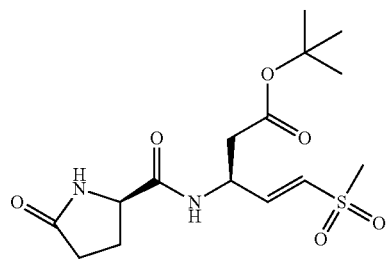
24. (2-Pyrrolidinone-5-carbonyl)- Asp methyl vinyl sulfone.
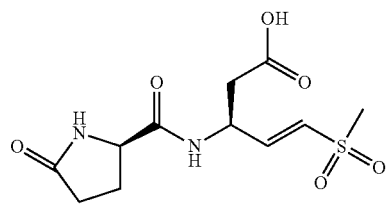
25. Z-Asp(O-tBu)-t-Leu-Pro-Asp(O-tBu)-methyl vinyl sulfone
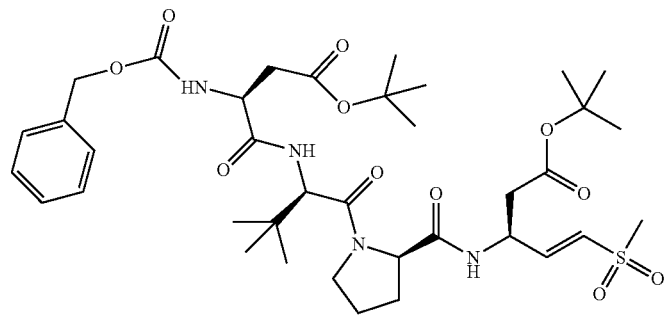

TABLE 1-continued
CPD NO./CPD NAME/STRUCTURE
26. Z-Asp-t-Leu-Pro-Asp-methyl vinyl sulfone.
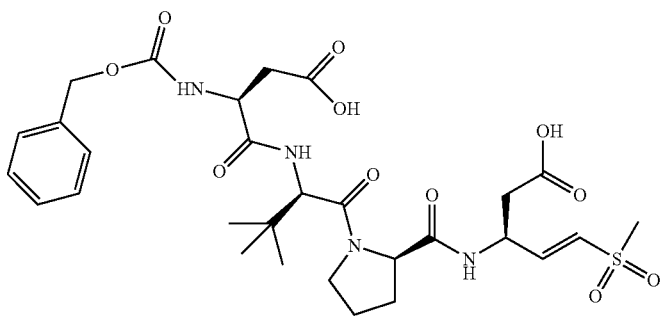
27. Z-Asp(O-tBu)-Cyclopropylglycine-Pro-
Asp(O-tBu)-methyl vinyl sulfone
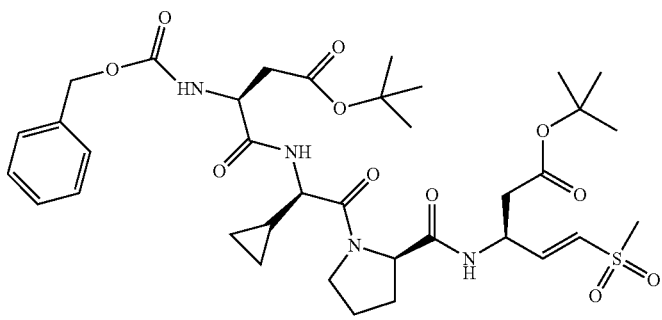
28. Z-Asp-Cyclopropylglycine-Pro-Asp-methyl
vinyl sulfone.
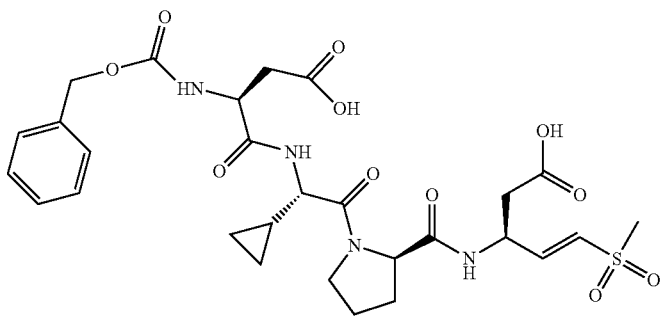

TABLE 1-continued
CPD NO./CPD NAME/STRUCTURE
29. Z-Asp(O-tBu)-Phenylglycine-Pro-Asp(O-tBu)-methyl vinyl sulfone
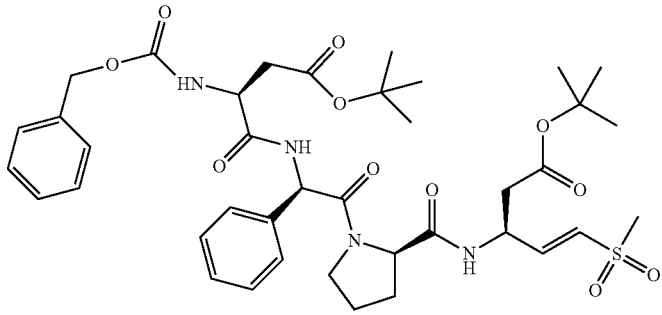
30. Z-Asp-Phenylglycine-Pro-Asp-methyl vinyl sulfone
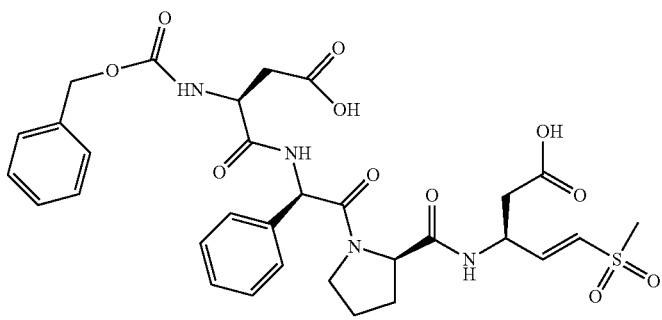
31. Z-Asp(O-tBu)-t-Leu-(Azetidine-2-carbonyl)-Asp(O-tBu)-methyl vinyl sulfone.
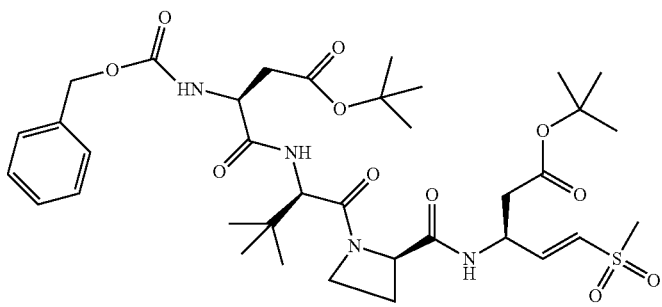

TABLE 1-continued
CPD NO./CPD NAME/STRUCTURE
32. Z-Asp-t-Leu-(Azetidine-2-carbonyl)-Asp-methyl vinyl sulfone.
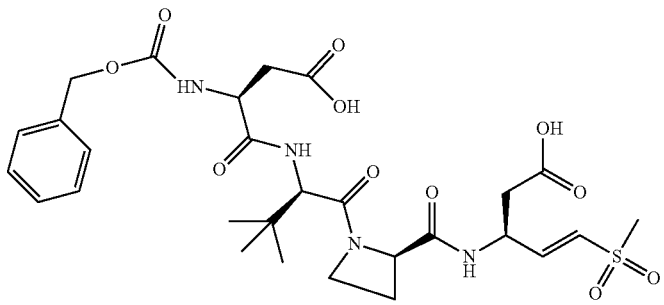
33. z-Asp(O-tBu)-t-Leu-(Azetidine-2-carboxylic acid)
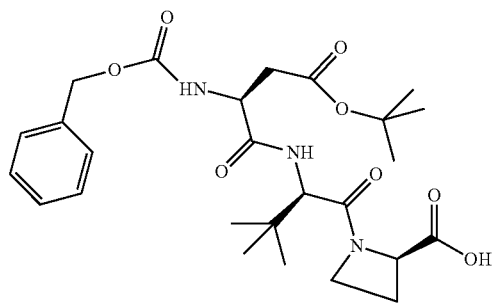
34. 2-Quinoline carbonyl-t-Leu-(Azetidine-2-carboxylic acid)
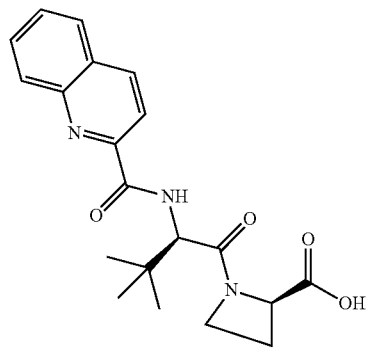

TABLE 1-continued
CPD NO./CPD NAME/STRUCTURE
35. Z-Asp(O-tBu)-Trp(N-Me)-Val-Asp(O-tBu)-methyl vinyl sulfone
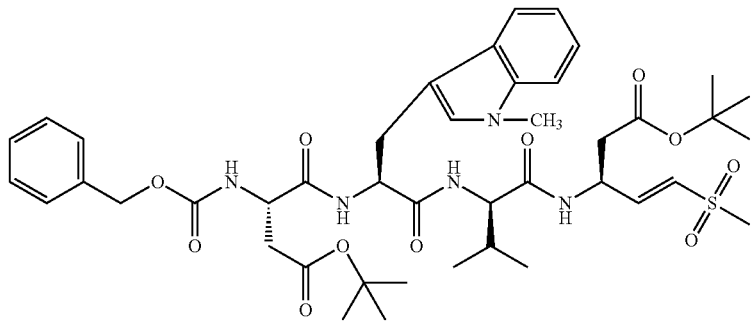
36. Z-Asp-Trp(N-Me)-Val-Asp-methyl vinyl sulfone
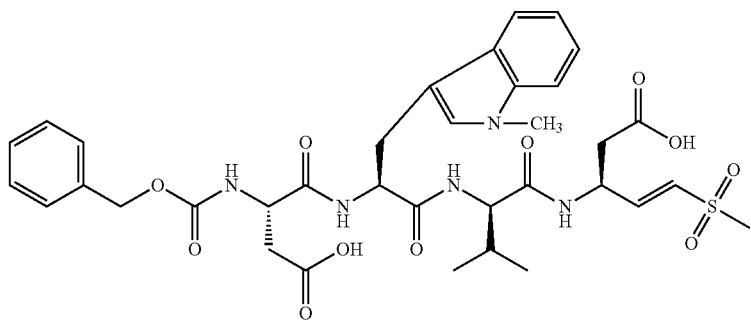
37. Z-Val-Glu(O-tBu)-Ile-Asp(O-tBu)-methyl vinyl sulfone
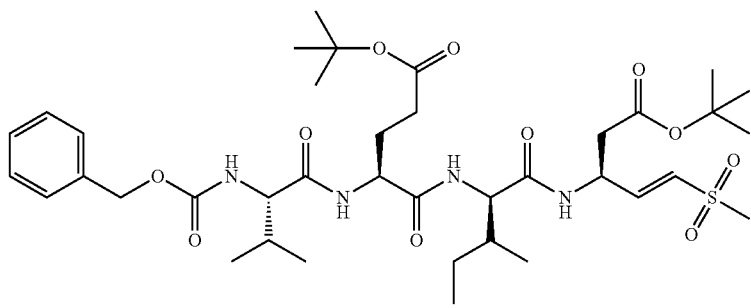

TABLE 1-continued
CPD NO./CPD NAME/STRUCTURE
38. Z-Val-Glu-Ile-Asp-methyl vinyl sulfone
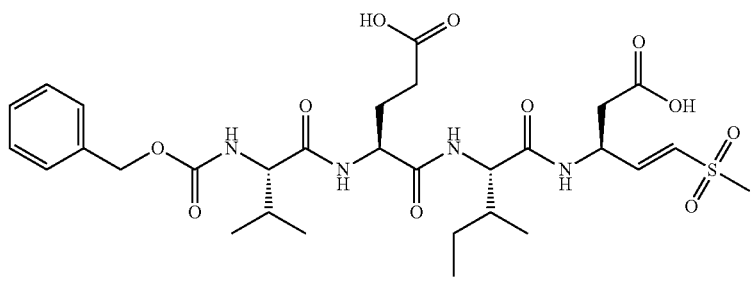
39. Z-Trp-Glu(O-tBu)-Val-Asp(O-tBu)-methyl vinyl sulfone
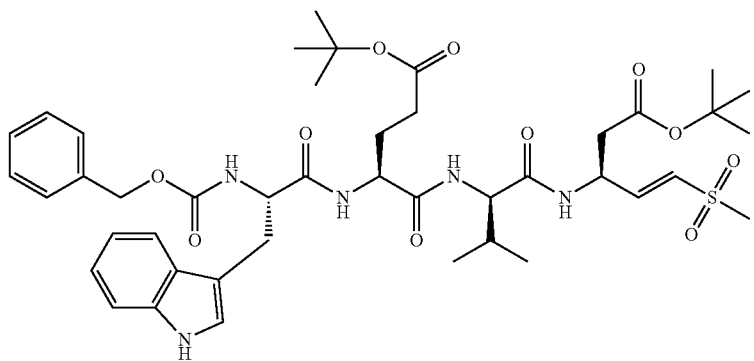
40. Z-Trp-Glu-Val-Asp-methyl vinyl sulfone
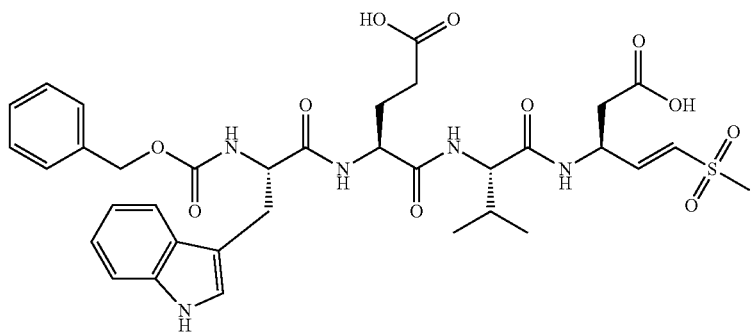

TABLE 1-continued
CPD NO./CPD NAME/STRUCTURE
41. Boc-Tyr-Val-Ala-Asp(β-tert-butyl)methyl vinyl sulfone
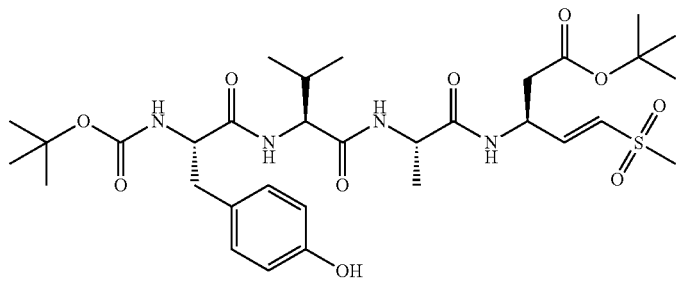
42. Tyr-Val-Ala-Asp methyl vinyl sulfone
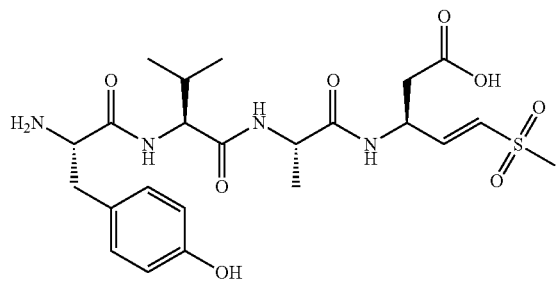
43. Boc-Asp(β-tert-butyl)ethyl vinyl ester
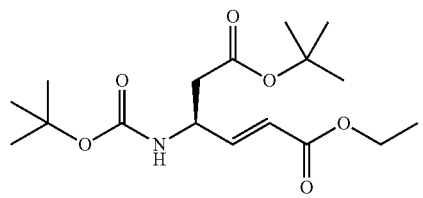
44. Asp ethyl vinyl ester tosyl salt.
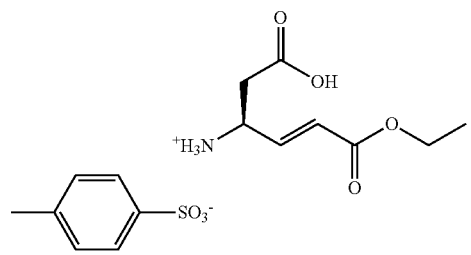

TABLE 1-continued
CPD NO./CPD NAME/STRUCTURE
45. t-Leu-Pto-OAllyl TFA salt
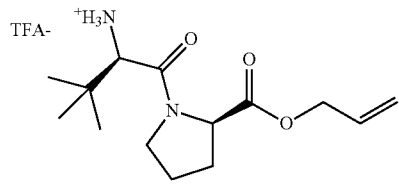
46. 2-Quinoline carbonyl-t-Leu-Pro-OAllyl
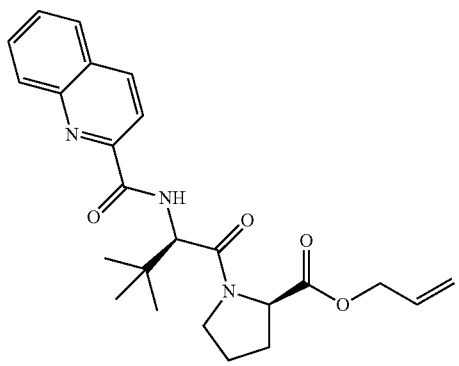
47. 2-Quinoline carbonyl-t-Leu-Pro-OH
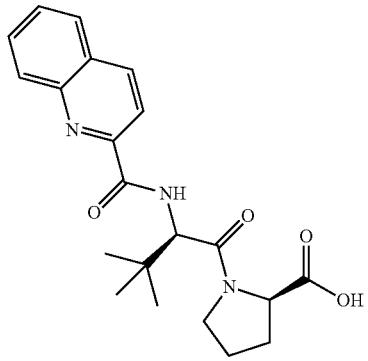
48. 1,5-Naphthyridine-(2-carbonyl)-t-Leu-Pro-OAllyl
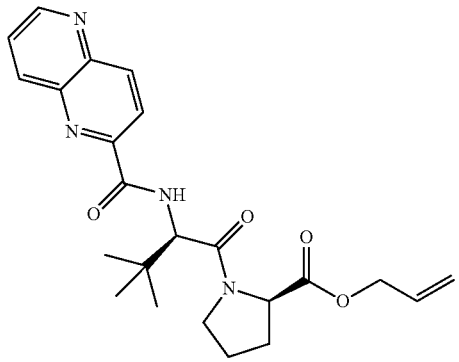

TABLE 1-continued
CPD NO./CPD NAME/STRUCTURE
49. (1,5-Naphthyridine-2-carbonyl)-t-Leu-Pro-OH
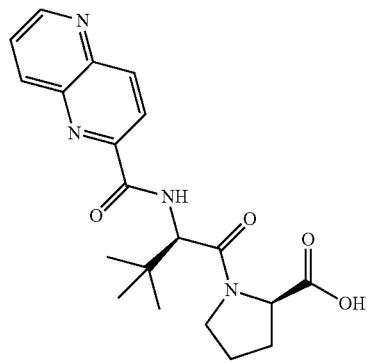
50. Quinoline-6-carbonyl-t-Leu-Pro-OAllyl
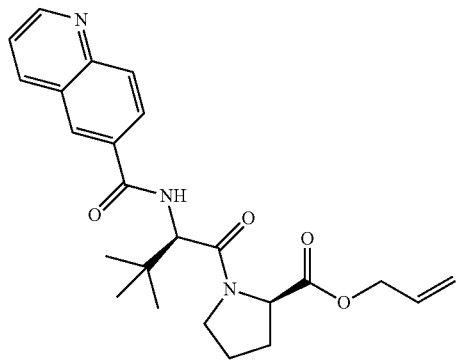
51. Quinoline-6-carbonyl-t-Leu-Pro-OH
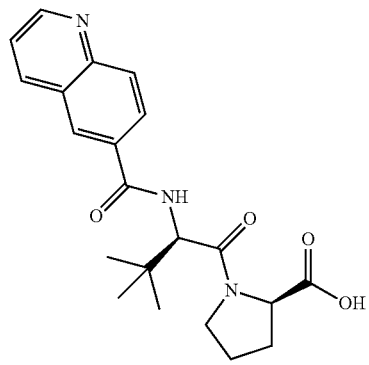

TABLE 1-continued
CPD NO./CPD NAME/STRUCTURE
52. 4-((tert-butoxycarbonyl)amino)-4-amino-3-chlorobenzene carbonyl-t-Leu-Pro-OAllyl
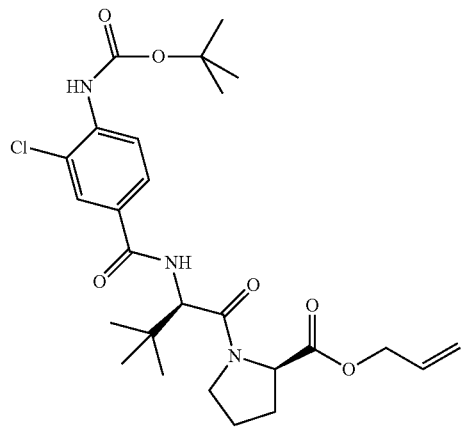
53. 4-((tert-butoxycarbonyl)amino)-4-amino-3-chlorobenzene carbonyl-t-Leu-Pro-OH
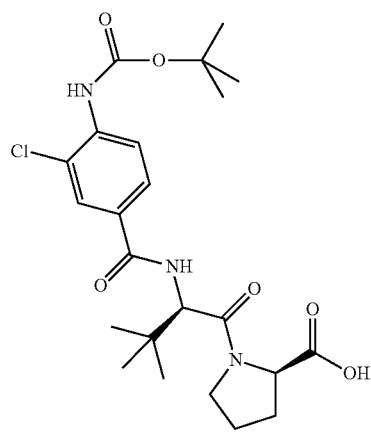
54. 4-((tert-butoxycarbonyl)amino)-3-chlorobenzoic acid
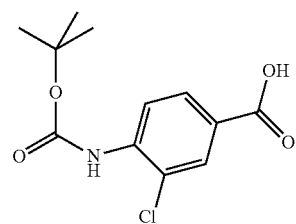

TABLE 1-continued
CPD NO./CPD NAME/STRUCTURE
55. z-Asp(O-tBu)-t-Leu- Pro-OAllyl
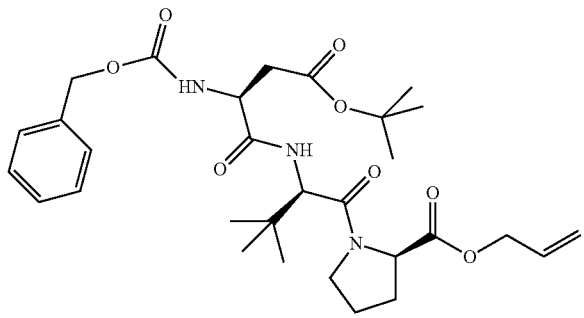
56. z-Asp(O-tBu)-t-Leu-Pro-OH
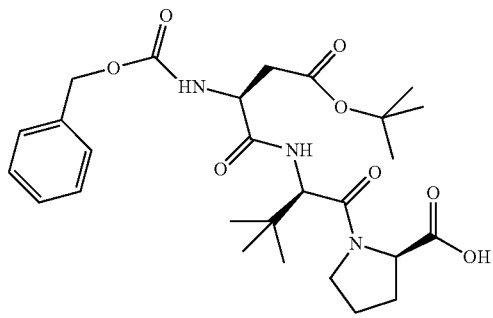
57. Z-Asp-t-Leu-Pro-Asp αchlorovinyl Ethyl Vinyl Ester
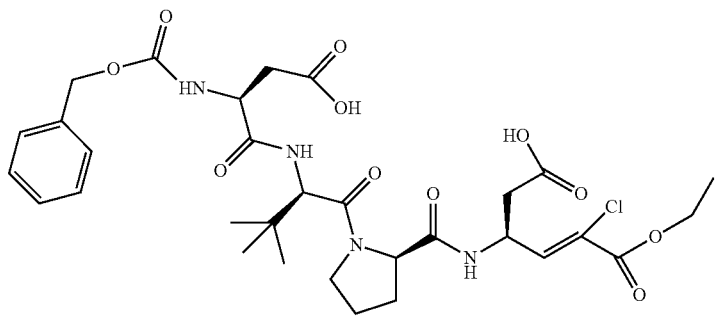

TABLE 1-continued
CPD NO./CPD NAME/STRUCTURE
58. Z-Val-Glu(O-t-Bu)-His (N-Boc)-OAllyl
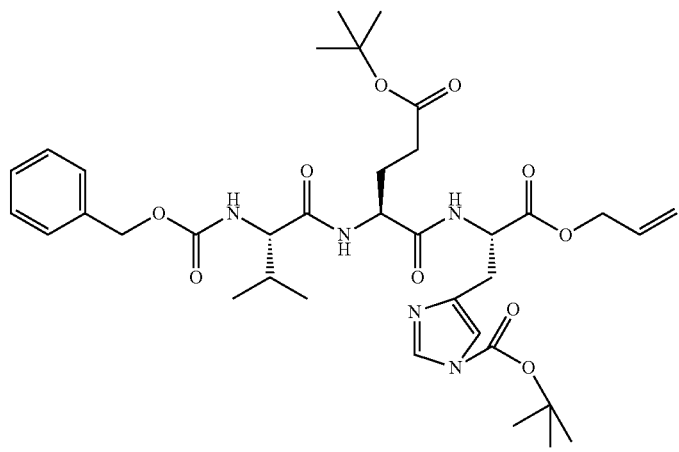
59. Phenylglycine-Pro-OAllyl TFA salt
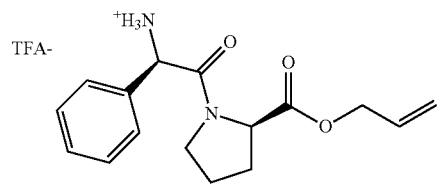
60. z-Asp(O-tBu)-Phg-Pro-OAllyl
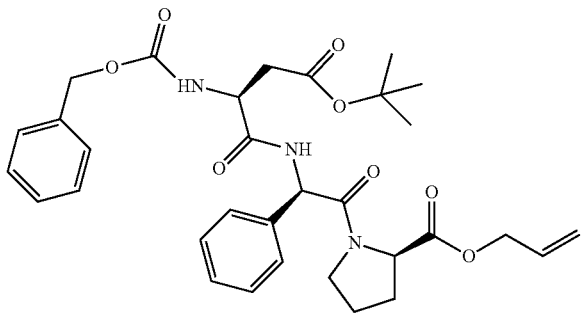
61. z-Asp(O-tBu)-Phg-Pro-OH
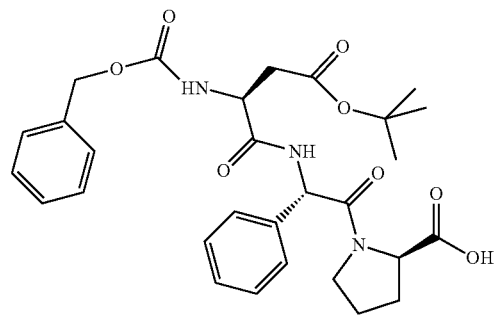

TABLE 1-continued
CPD NO./CPD NAME/STRUCTURE
62. Cyclopropylglycine-Pro-OAllyl TFA salt
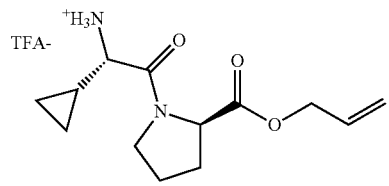
63. z-Asp(O-tBu)-Cyclopropylglycine-Pro-OAllyl
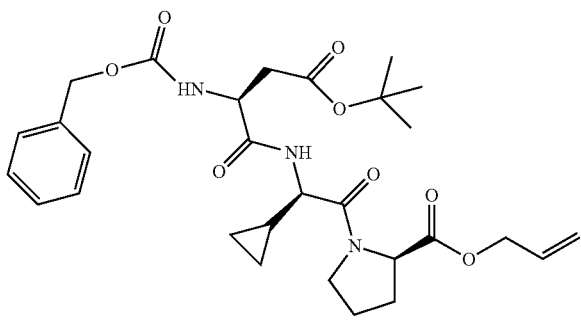
64. z-Asp(O-tBu)-Cyclopropylglycine-Pro-OH
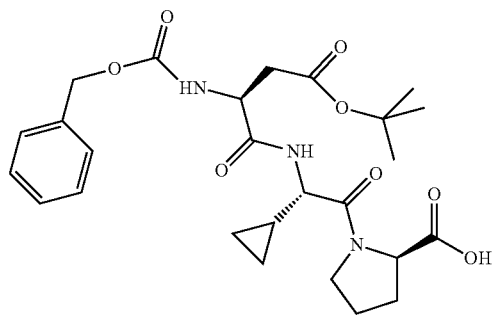
65. 2-Quinoline carbonyl-Val-OAllyl
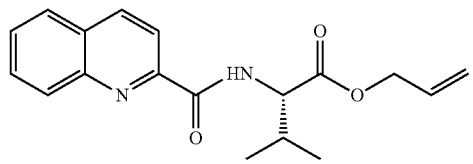
66. 2-quinoline carbonyl-Val-OH
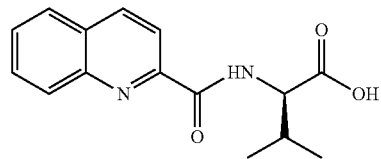

TABLE 1-continued
CPD NO./CPD NAME/STRUCTURE
67. Quinoline-2-carbonyl-Glu(Ot-Bu)-OAllyl
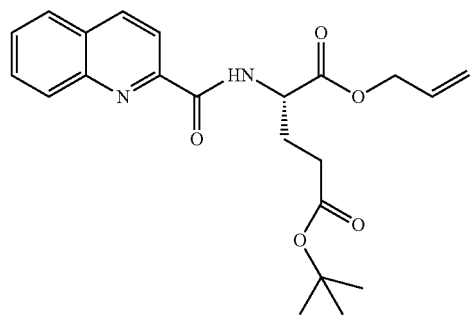
68. Quinoline-2-carbonyl-Glu(Ot-Bu)-OH
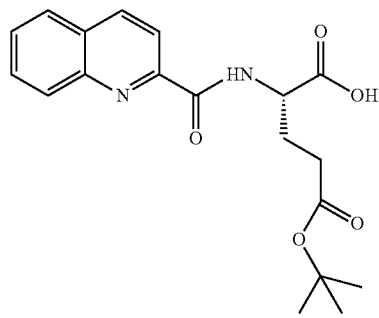
69. Boc-Glu(O-tBu)-Val-OAllyl
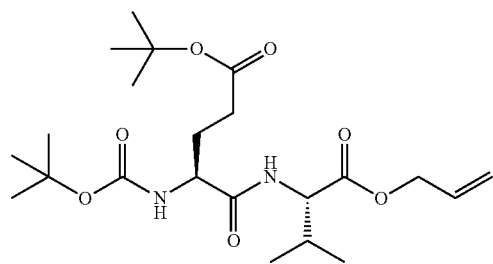
70. Glu(O-tBu)-Val-OAllyl TFA salt
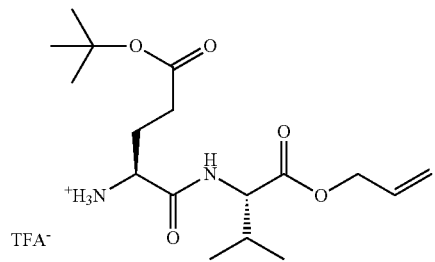

TABLE 1-continued
CPD NO./CPD NAME/STRUCTURE
71. Z-Trp-Glu-(OtBu)-Val-OAllyl
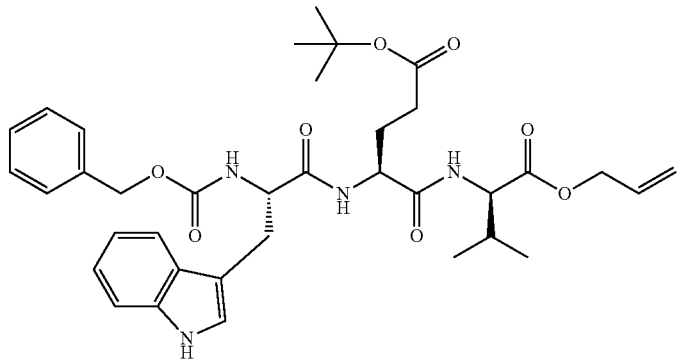
72. Z-Trp-Glu-(OtBu)-Val-OH
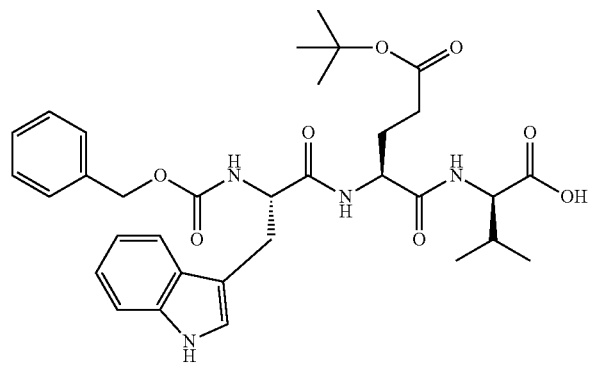
73. Z-Asp(O-tBu)-Trp(N-Me)-Val-OH
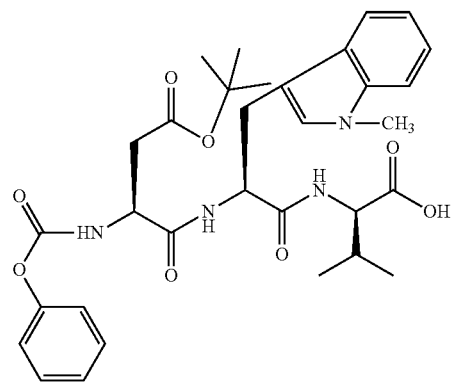

TABLE 1-continued
CPD NO./CPD NAME/STRUCTURE
74. Z-Asp-Trp(N-Me)-Val-OAllyl
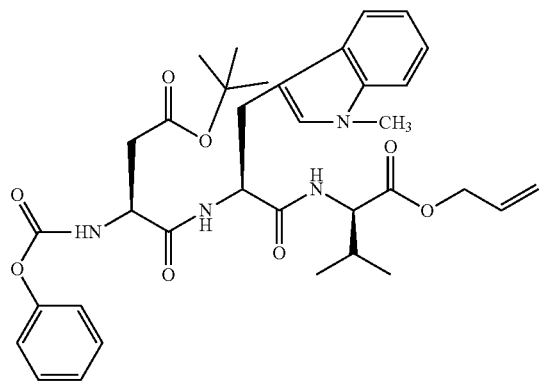
75. Boc-Glu(O-tBu)-Ile-OAllyl
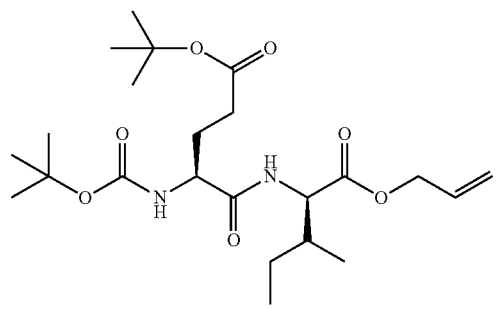
76. Glu(O-tBu)-Ile-OAllyl TFA salt
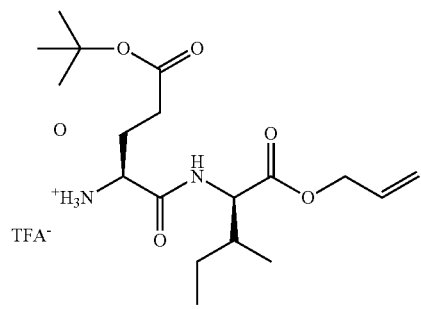
77. Z-Val-Glu-(OtBu)-Ile-OAllyl
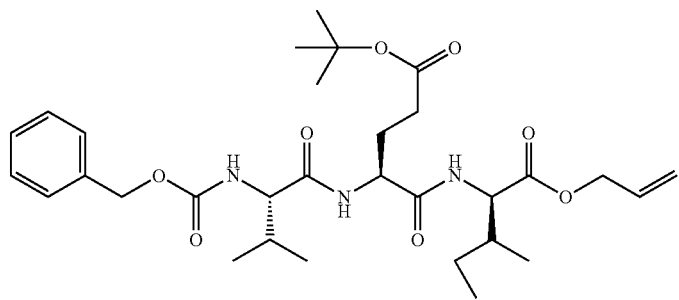

TABLE 1-continued
CPD NO./CPD NAME/STRUCTURE
78. Z-Val-Glu-(OtBu)-Ile-OH
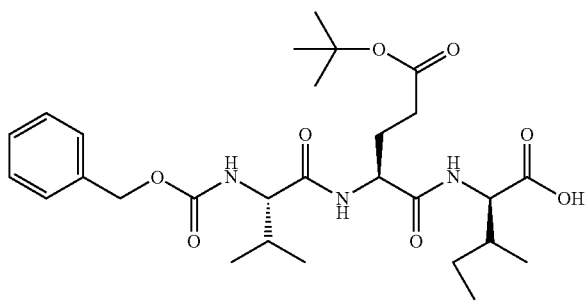
79. Boc-Tyr-Val-Ala-OH
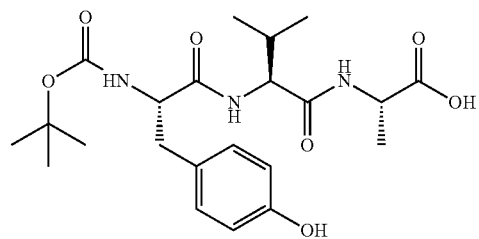
80. Val-Ala-OAllyl TFA salt
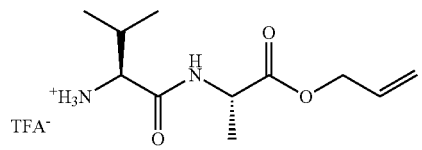
81. Boc-Tyr-Val-Ala-OAllyl
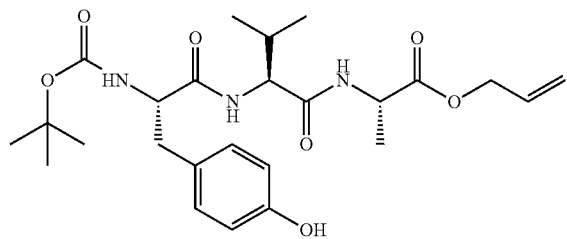
82. Boc-Glu(β-tert-butyl) methyl vinyl sulfone
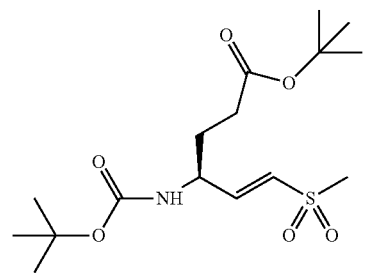

TABLE 1-continued
CPD NO./CPD NAME/STRUCTURE
83 Glu(β-tert-butyl)methyl vinyl sulfone tosyl salt
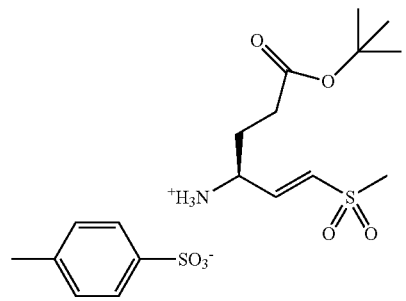
84. Z-Asp-Phg-Val-Glu methyl vinyl sulfone
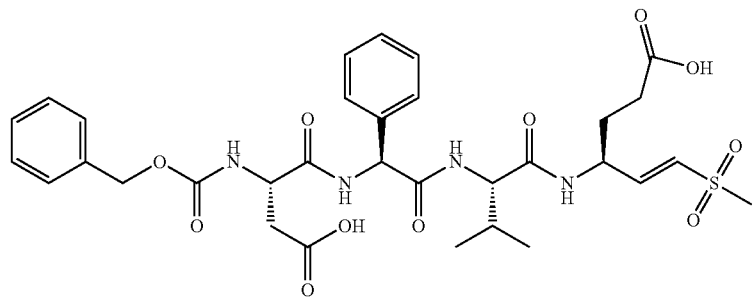
85. Z-Asp(β-tert-Butyl)-Phg-Val-Glu(β-tert-Butyl)methyl vinyl sulfone
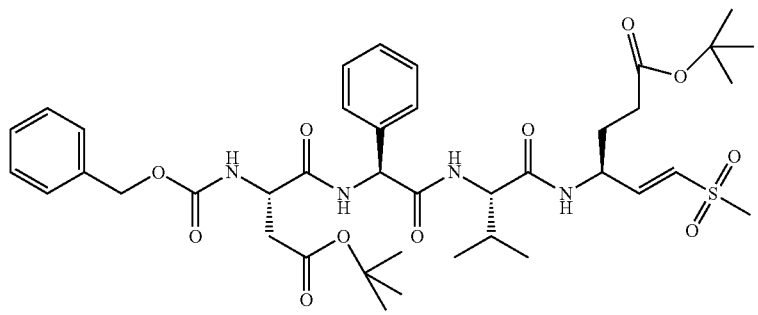
86. Z-Asp-Phg-Val-(β-Cyano-Ala) methyl vinyl sulfone
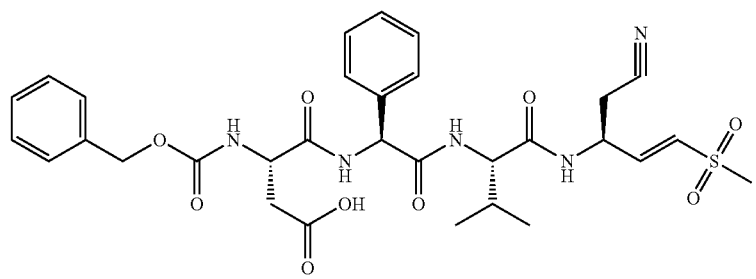

TABLE 1-continued
CPD NO./CPD NAME/STRUCTURE
87. Z-Asp-Phg-Val-(β-Cyano-Ala) αchlorovinyl methyl vinyl sulfone
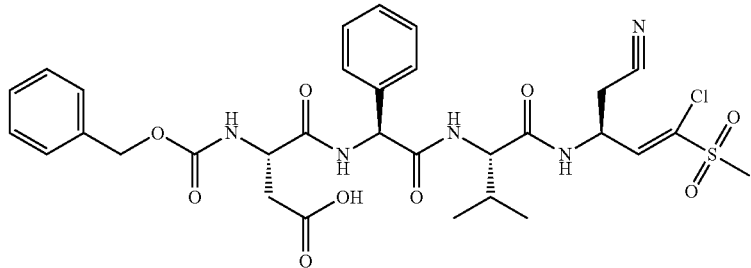
88. Z-Asp-Phg-Val-(β-1H tetrazole-Ala) methyl vinyl sulfone
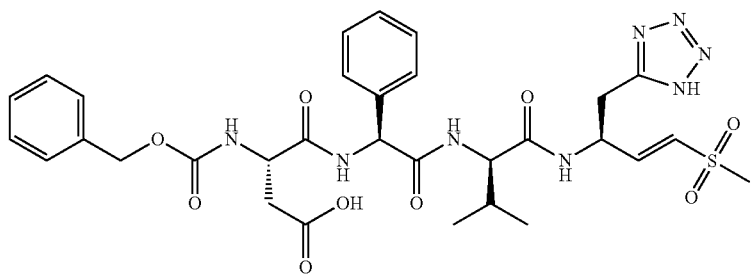
89. Z-Asp-Phg-Val-(β-1H tetrazole-Ala) αchlorovinyl methyl vinyl sulfone
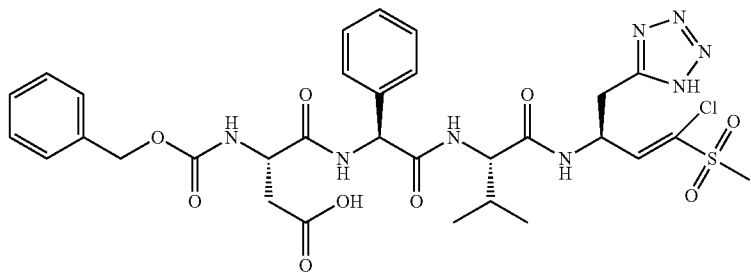

TABLE 1-continued
CPD NO./CPD NAME/STRUCTURE
90. (4-amino-3-chlorobenzene carbonyl)-t-Leu-
Pro-β-Cyano-Ala methyl vinyl sulfone
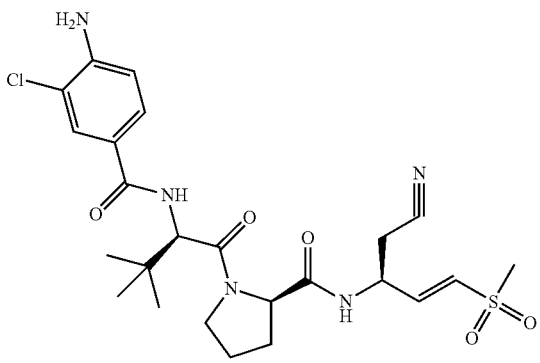
91. 4-amino-3-chlorobenzene carbonyl-t-Leu-
Pro-β-Cyano-Ala αchlorovinyl methyl vinyl
sulfone
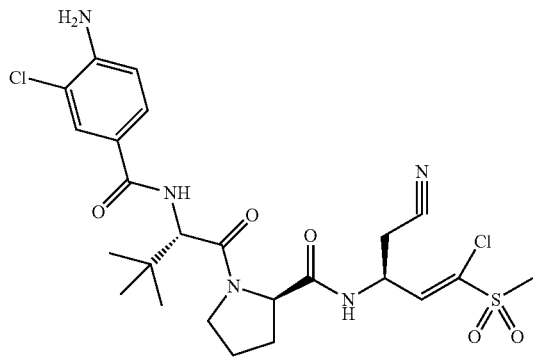
92. (4-amino-3-chlorobenzene carbonyl-t-Leu-
Pro-(β-1H tetrazole-Ala) methyl vinyl sulfone
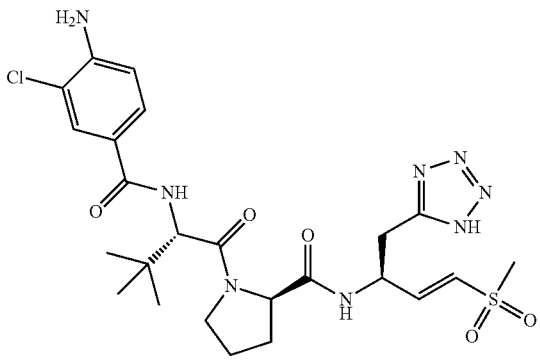

TABLE 1-continued
CPD NO./CPD NAME/STRUCTURE
93. 4-amino-3-chlorobenzene carbonyl)-t-Leu-
Pro-(β-1H tetrazole-Ala) αchlorovinyl methyl
vinyl sulfone
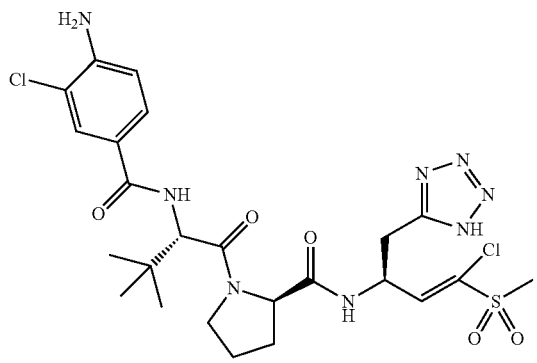
94. 2-Quinoline carbonyl-t-Leu-Pro-β-Cyano-
Ala methyl vinyl sulfone
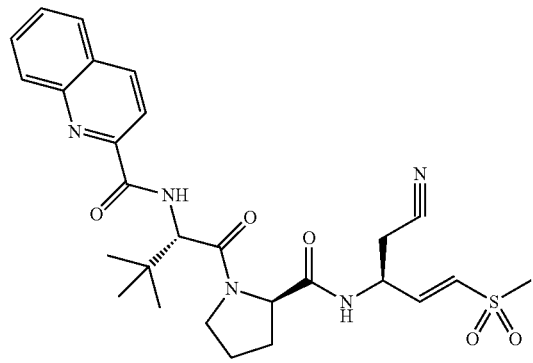
95. 2-Quinoline carbonyl-t-Leu-Pro-(β-Cyano-
Ala) αchlorovinyl methyl vinyl sulfone
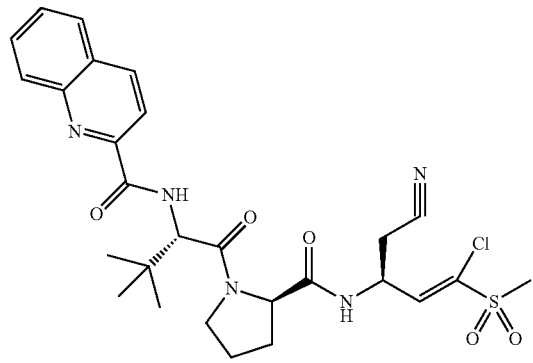

TABLE 1-continued
CPD NO./CPD NAME/STRUCTURE
96. 2-Quinoline carbonyl-t-Leu-Pro-(β-1H tetrazole-Ala) methyl vinyl sulfone
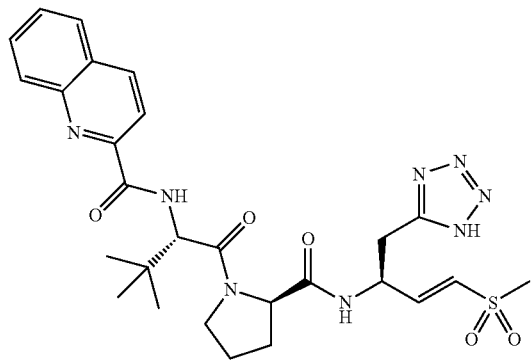
97. 2-Quinoline carbonyl-t-Leu-Pro-(β-1H tetrazole-Ala) αchlorovinyl methyl vinyl sulfone
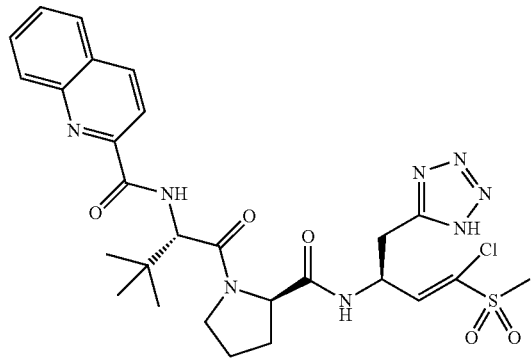
98. Z-Asp-t-Leu-Pro-(β-Cyano-Ala) methyl vinyl sulfone
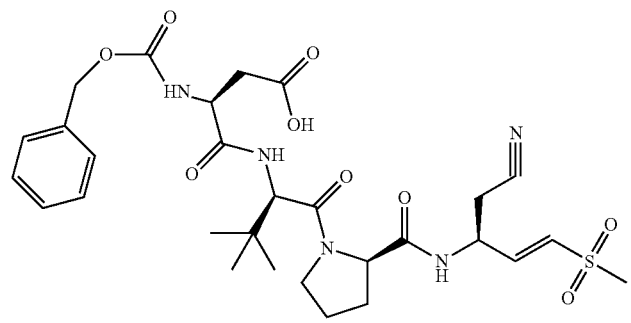

TABLE 1-continued
CPD NO./CPD NAME/STRUCTURE
99. Z-Asp-t-Leu-Pro-(β-Cyano-Ala)
αchlorovinyl methyl vinyl sulfone
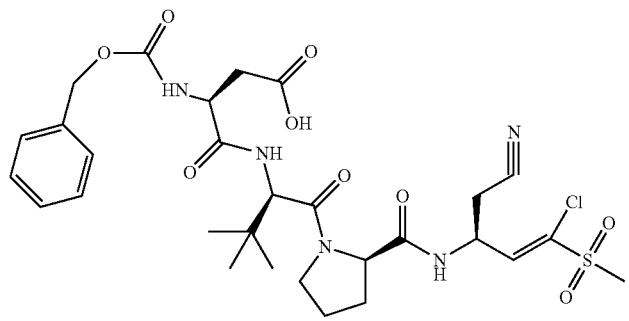
100. Z-Asp-t-Leu-Pro-(β-1H tetrazole-Ala)
methyl vinyl sulfone
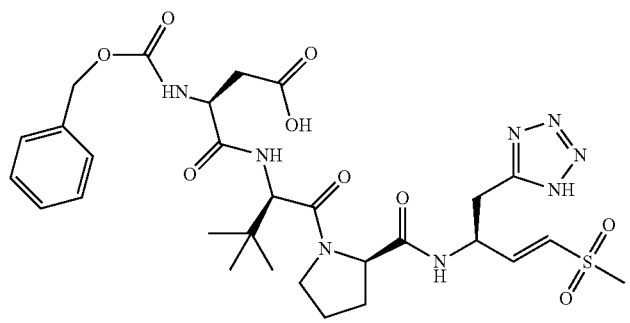
101. Z-Asp-t-Leu-Pro-(β-1Htetrazole-Ala)
αchlorovinyl methyl vinyl sulfone
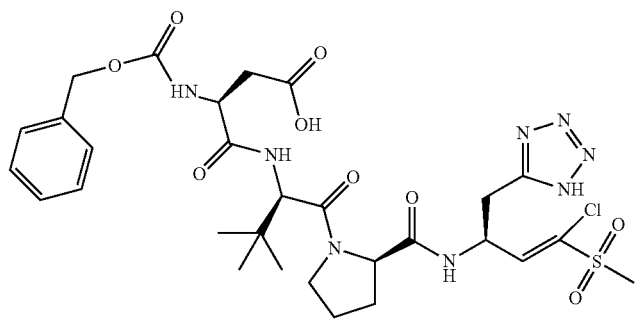

TABLE 1-continued
CPD NO./CPD NAME/STRUCTURE
102. Z-Asp-t-Leu-Pro-Glu methyl vinyl sulfone
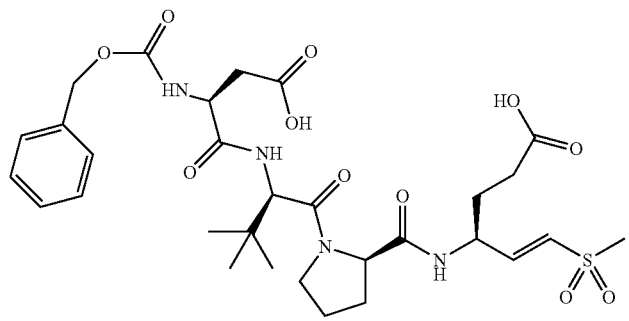
103. z-Asp(O-tBu)-t-Leu-Allyl azetidine-2-carboxylate
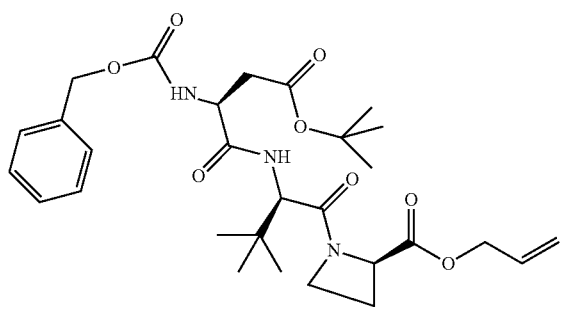
104. Z-Asp(β-tert-Butyl)-Phg-Val-Asp(β-tert-Butyl) Ethyl Vinyl Ester
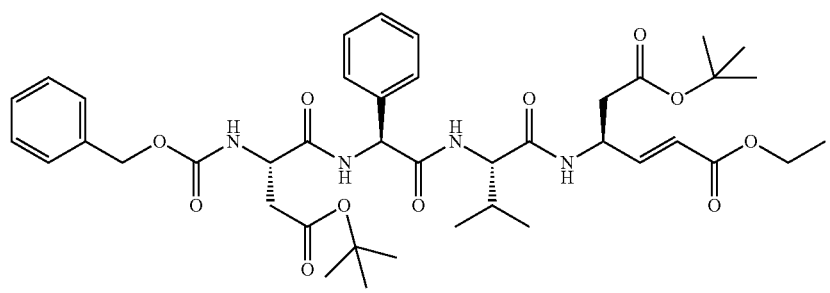
105. Z-Asp-Phg-Val-Asp Ethyl Vinyl Ester
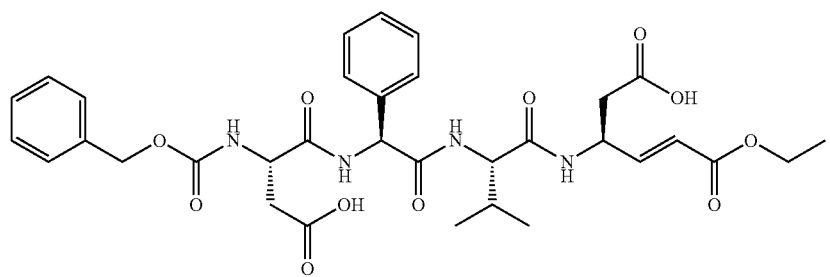

TABLE 1-continued
CPD NO./CPD NAME/STRUCTURE
106. Asp(β-tert-Butyl)Ethyl Vinyl Ester, Tosyl Salt
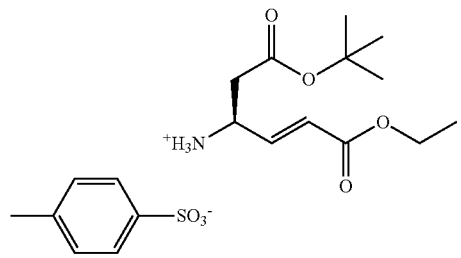
107. Asp(β-tert-Butyl) αchlorovinyl Ethyl Vinyl Ester, Tosyl Salt
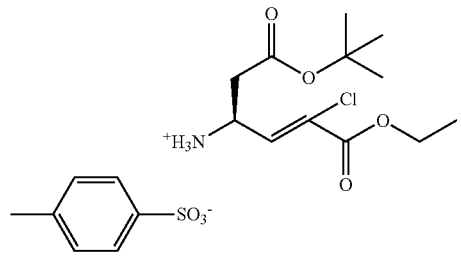
108. Z-Asp(β-tert-Butyl)-Phg-Val-Asp(β-tert-Butyl)αchlorovinyl Ethyl Vinyl Ester
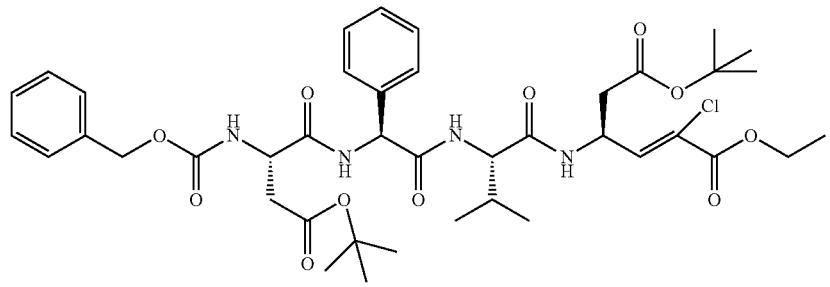
109. Z-Asp-Phg-Val-Asp αchlorovinyl Ethyl Vinyl Ester
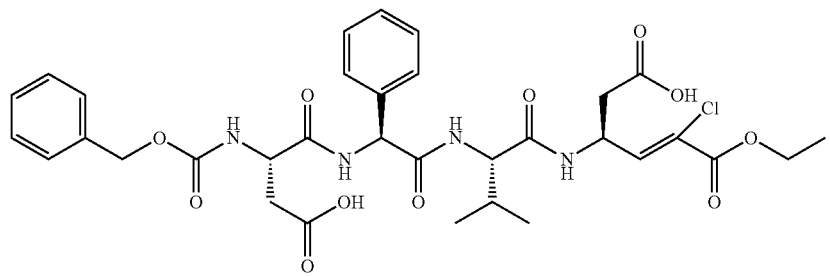

TABLE 1-continued
CPD NO./CPD NAME/STRUCTURE
110. Z-Asp-Phg-Val-(β-1H tetrazole-Ala) Ethyl Vinyl Ester
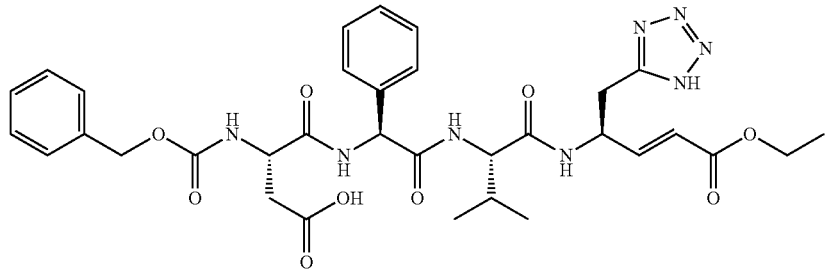
111. Z-Asp-Phg-Val-(β-1H tetrazole-Ala) αchlorovinyl Ethyl Vinyl Ester
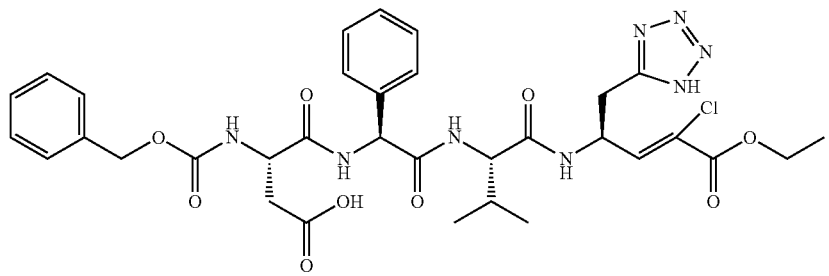
112. (4-amino-3-chlorobenzene carbonyl)-t-Leu-Pro-(β-1H tetrazole-Ala) Ethyl Vinyl Ester
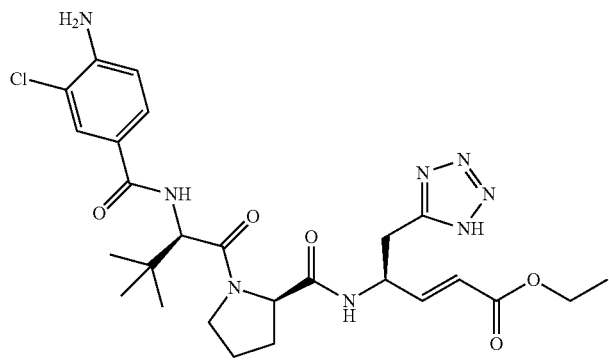

TABLE 1-continued
CPD NO./CPD NAME/STRUCTURE
113. (4-amino-3-chlorobenzene carbonyl)-t-Leu-Pro-(β-1H tetrazole-Ala) αchlorovinyl Ethyl Vinyl Ester
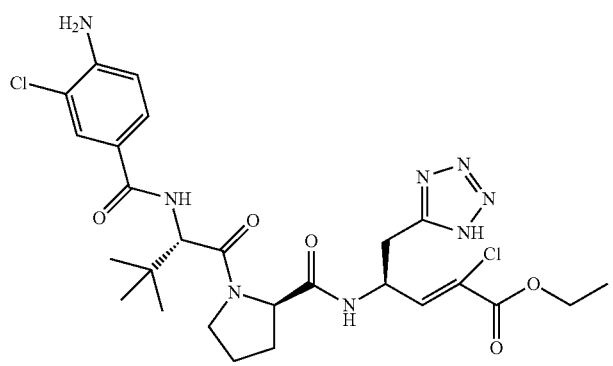
114. 2-Quinoline carbonyl-t-Leu-Pro-(β-1Htetrazole-Ala) Ethyl Vinyl Ester
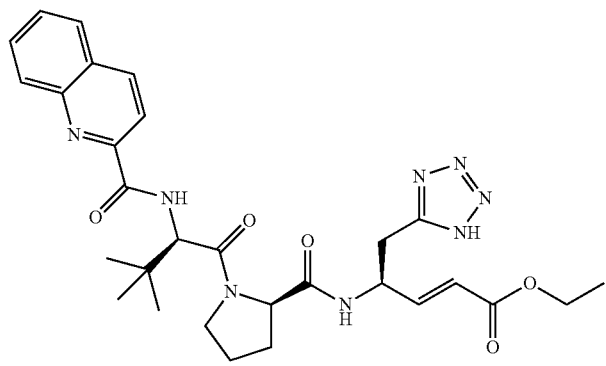
115. 2-Quinoline carbonyl-t-Leu-Pro-(β-1H tetrazole-Ala) αchlorovinyl Ethyl Vinyl Ester
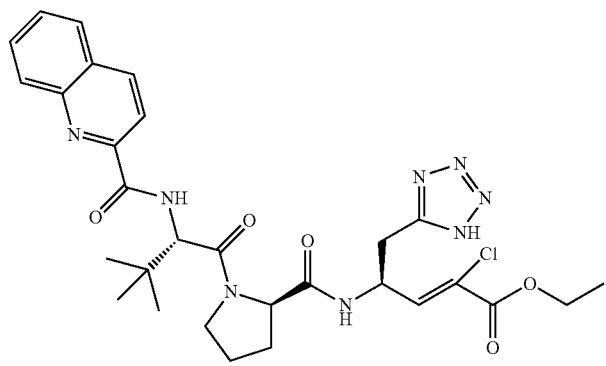

TABLE 1-continued
CPD NO./CPD NAME/STRUCTURE
116. 4-amino-3-chlorobenzene carbonyl-t-Leu-Pro-Asp Ethyl Vinyl Ester
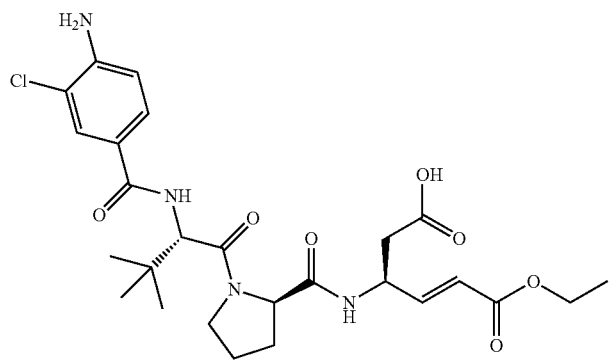
117. 4-amino-3-chlorobenzene carbonyl-t-Leu-Pro-Asp αchlorovinyl Ethyl Vinyl Ester
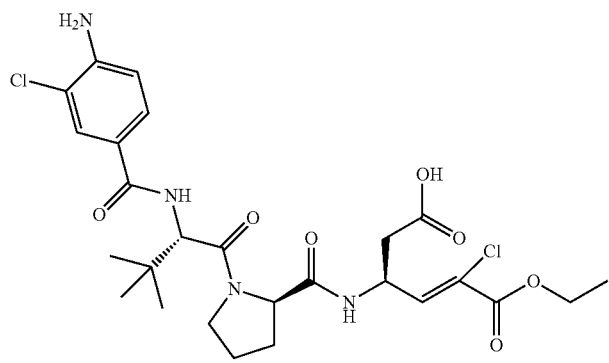
118. 2-Quinoline carbonyl-t-Leu-Pro-Asp Ethyl Vinyl Ester
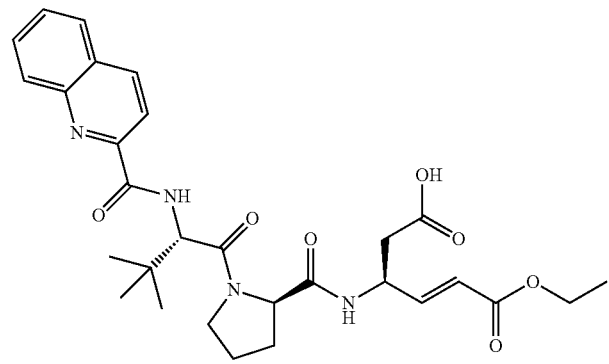

TABLE 1-continued
CPD NO./CPD NAME/STRUCTURE
119. 2-Quinoline carbonyl-t-Leu-Po-Asp
αchlorovinyl Ethyl Vinyl ester
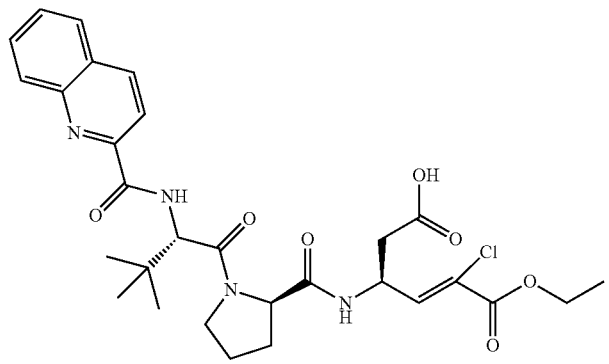
120. 2-Quinoline carbonyl-t-Leu-Pro-Asp (O-
tBu) Ethyl Vinyl Ester
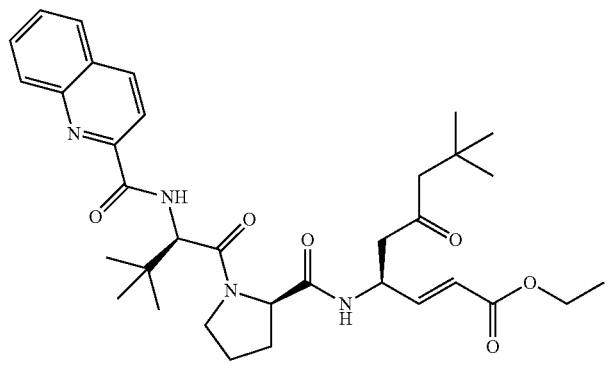
121. Z-Asp-t-Leu-Pro-(β-1Htetrazole-Ala) Ethyl
vinyl ester
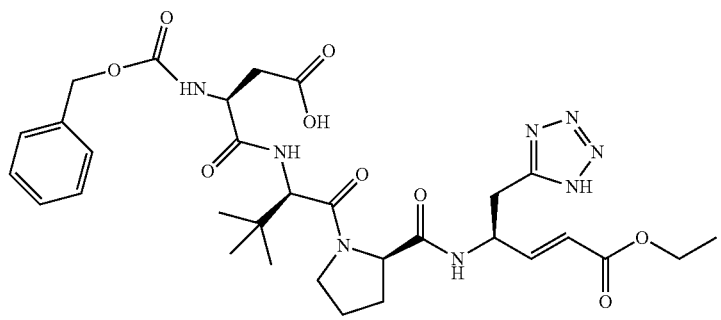

TABLE 1-continued
CPD NO./CPD NAME/STRUCTURE
122. Z-Asp-t-Leu-Pro-(β-1H tetrazole-Ala) αchlorovinyl Ethyl Vinyl Ester
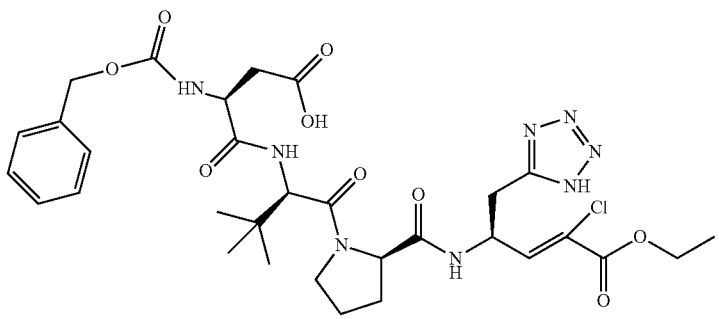
123. Z-Val-Glu-Ile-Asp- αchlorovinyl methyl vinyl sulfone
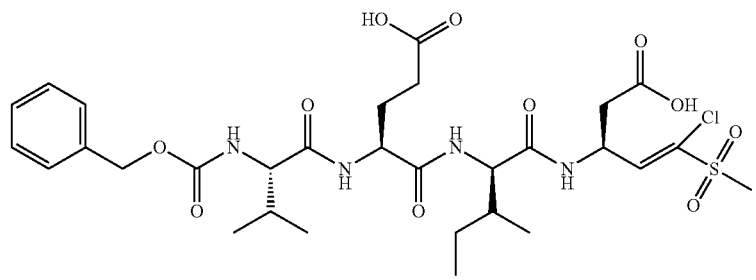
124. Z-Val-Glu-Ile-Asp Ethyl Vinyl ester
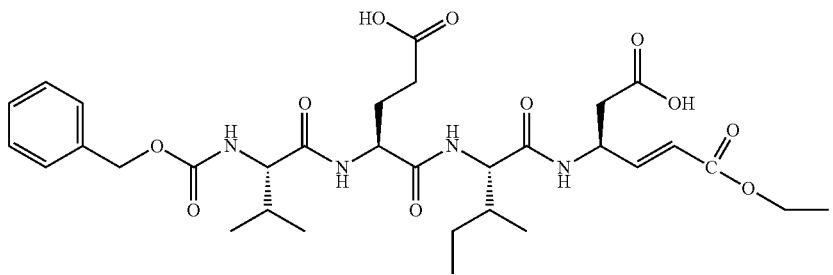
125. Z-Thr-Glu-Ile-Asp Ethyl Vinyl ester
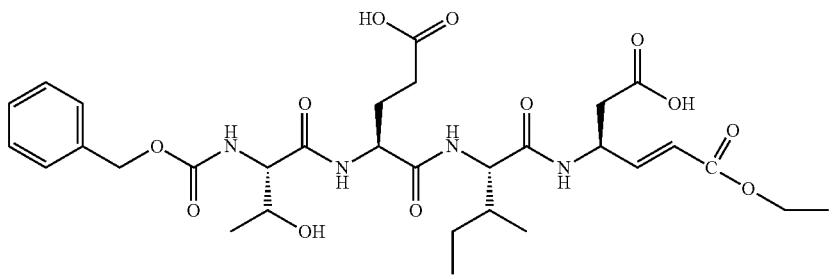

TABLE 1-continued
CPD NO./CPD NAME/STRUCTURE
126. Z-Val-Glu-Phg-Asp-Ethyl Vinyl ester
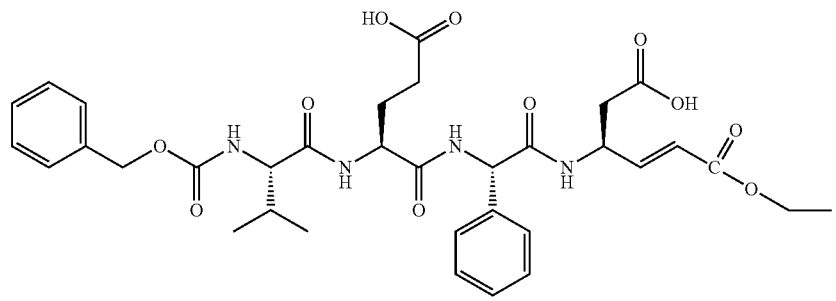
127. Z-Thr-Glu(OtBu)-Ile-OH
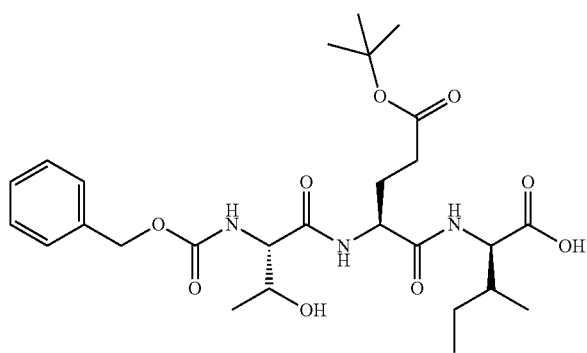
128. Z-Val-Glu(O-tBu)-Phg-OH
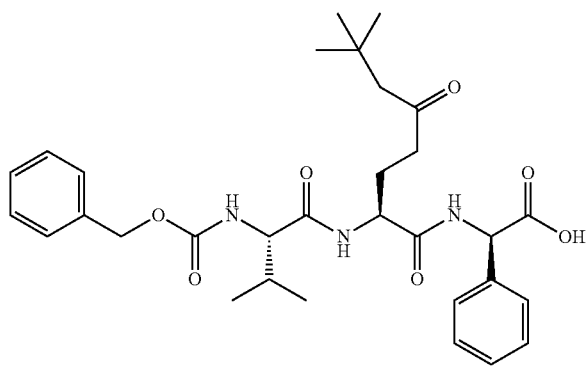
129. Z-Val-Ala-OH
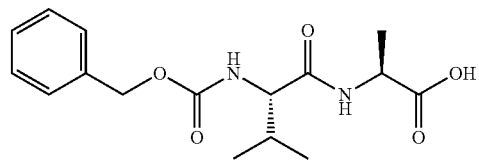

TABLE 1-continued
CPD NO./CPD NAME/STRUCTURE
130. Z-Val-Ala-Asp-αchlorovinyl methyl vinyl sulfone
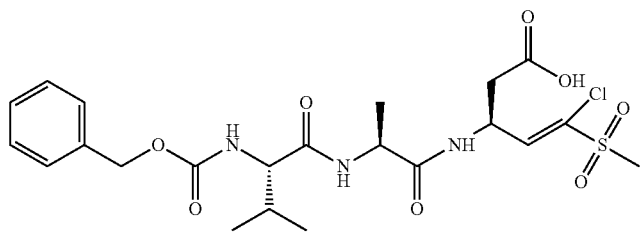
131. Z-Val-Ala-Asp-methyl vinyl sulfone
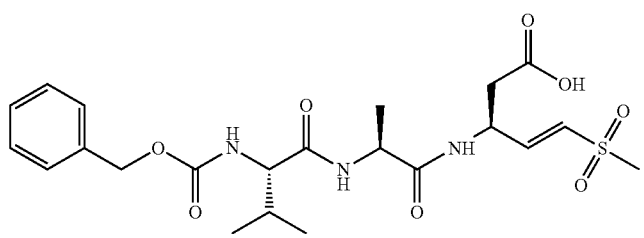
132. Z-Val-Glu(O-tBu)-His(N-Boc)-OH
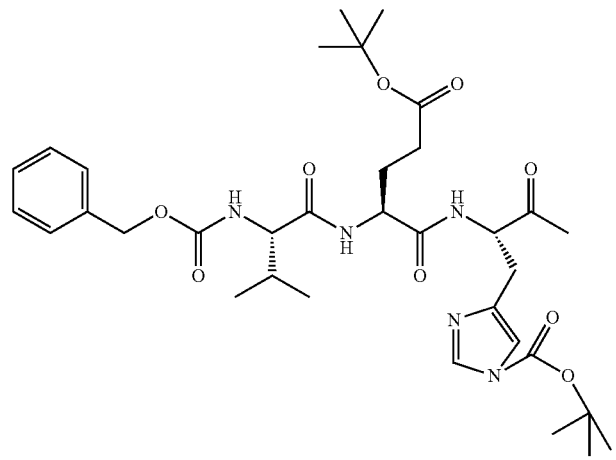
133. Z-Val-Glu-His-Asp methyl vinyl sulfone
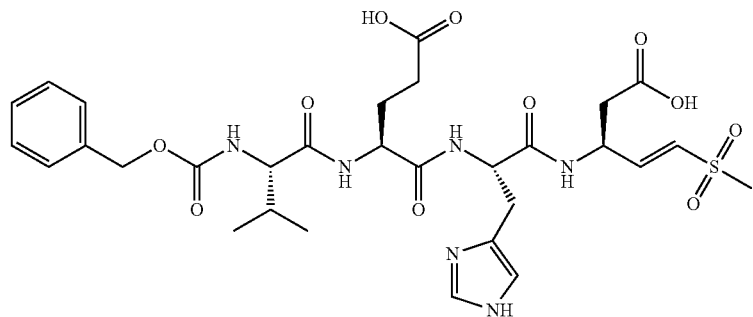

TABLE 1-continued
CPD NO./CPD NAME/STRUCTURE
134. Z-Val-Glu-His-Asp Ethyl Vinyl ester
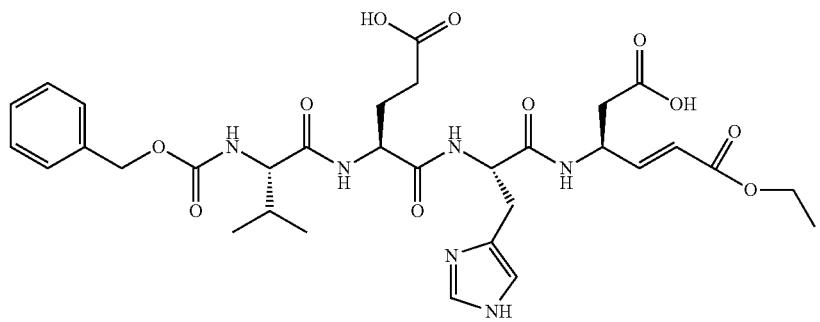
135. Z-Val-Glu-His-Asp αchlorovinyl methyl vinyl sulfone
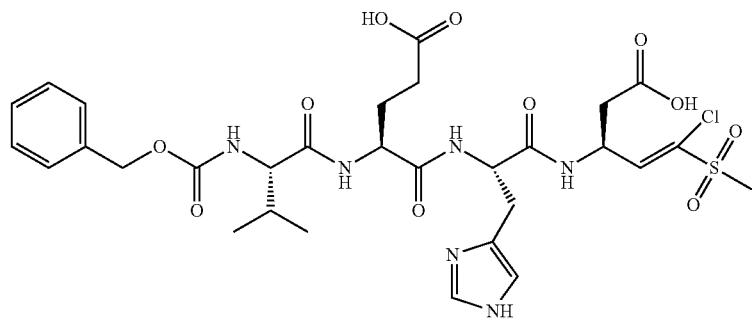
136. N-Tosyl Glu(O-tBu)-Ile-OH
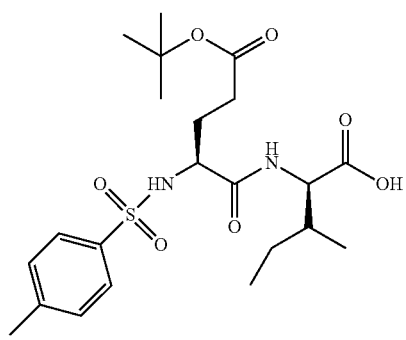

TABLE 1-continued
CPD NO./CPD NAME/STRUCTURE
137. N-Tosyl Glu-Ile-Asp Ethyl Vinyl ester
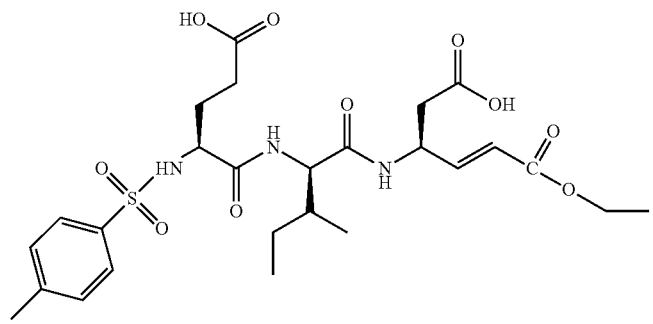
138. N-Tosyl Glu-Ile-Asp methyl vinyl sulfone
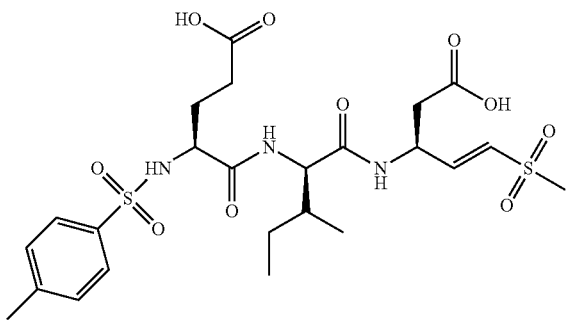
139. Z-Val-Arg-His-Asp methyl vinyl sulfone
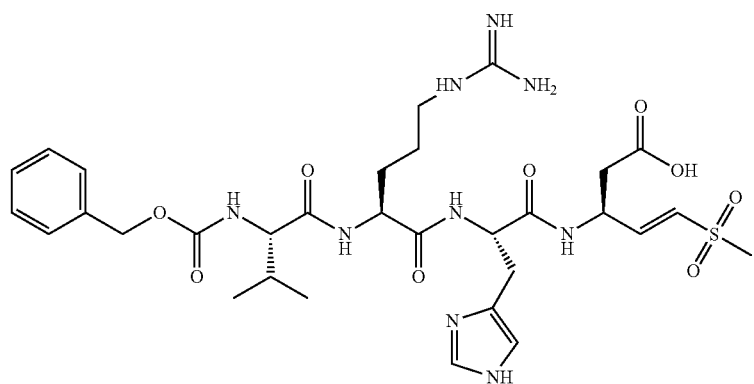

TABLE 1-continued
CPD NO./CPD NAME/STRUCTURE
140. Z-Val-Arg-His-Asp Ethyl Vinyl ester
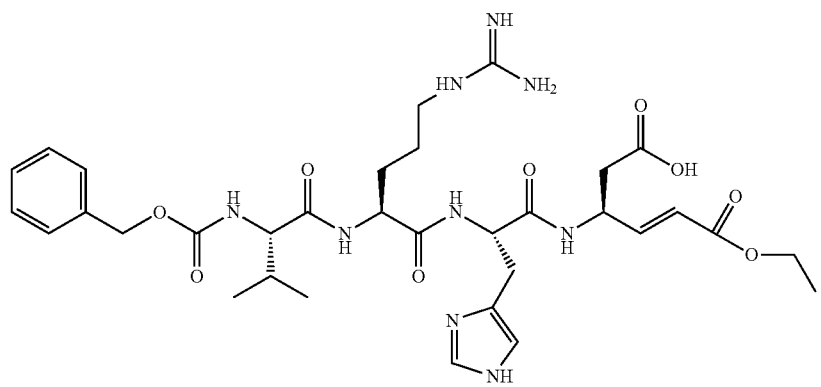
141. Z-Val-Arg-His-Asp αchlorovinyl methyl vinyl sulfone
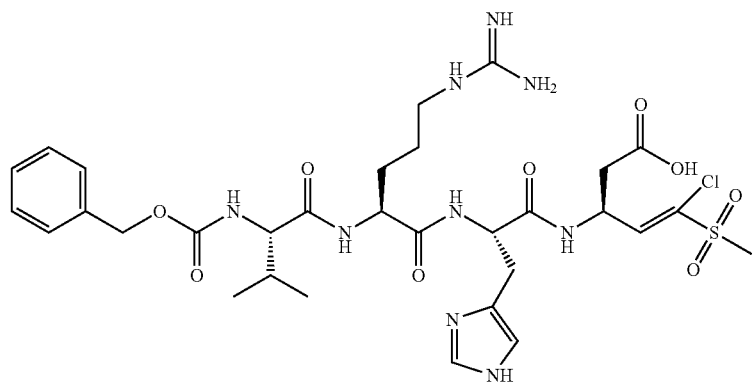
142. N-Boc Asp(β-tert-Butyl) αchlorovinyl Ethyl Vinyl Ester
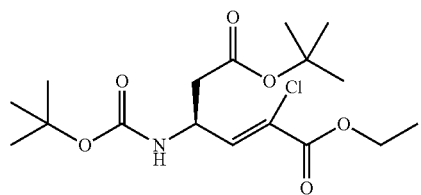
143. Z-Val-Ala-Asp Ethyl vinyl ester
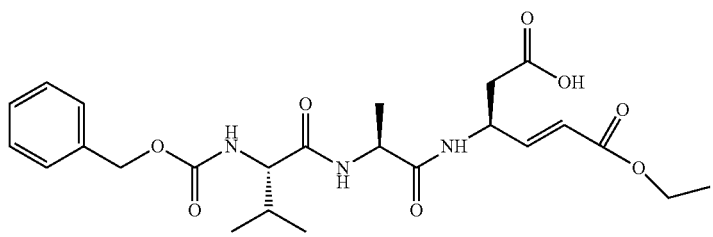

TABLE 1-continued
CPD NO./CPD NAME/STRUCTURE
144. Z-Val-Arg-Ile-Asp methyl vinyl sulfone
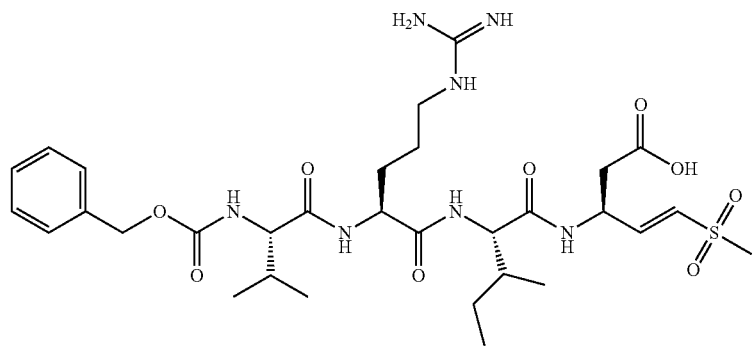
145. Z-Val-Arg-Ile-Asp αchlorovinyl methyl vinyl sulfone
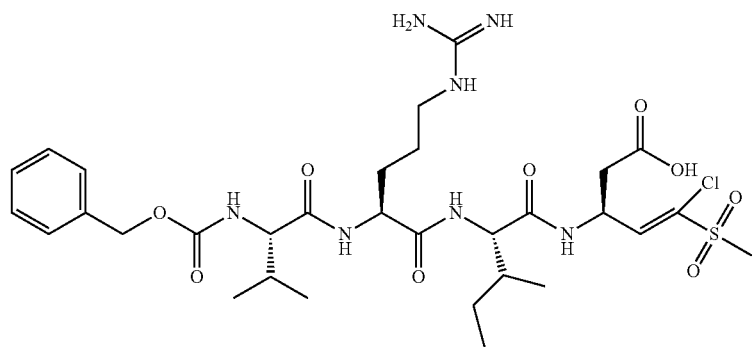
146. Z-Val-Arg-Ile-Asp Ethyl Vinyl ester
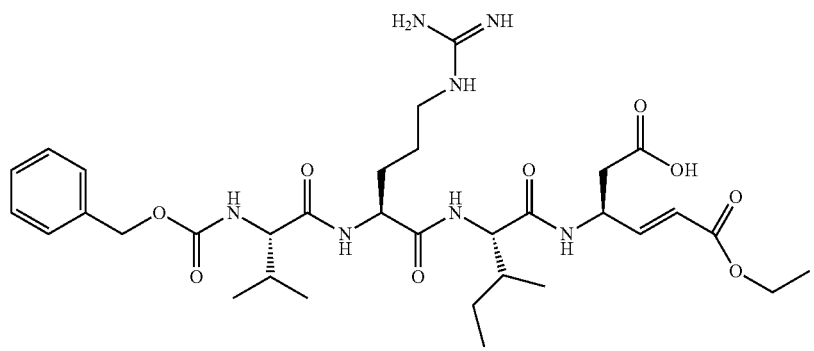

TABLE 1-continued
CPD NO./CPD NAME/STRUCTURE
147. N-Tosyl Arg-Ile-Asp methyl vinyl sulfone
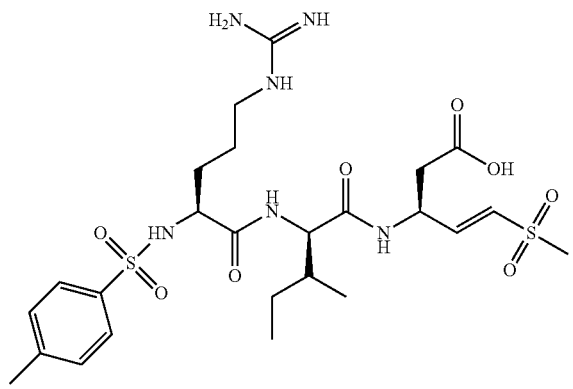
148. N-Tosyl Arg-Ile- Asp achlorovinyl methyl vinyl sulfone
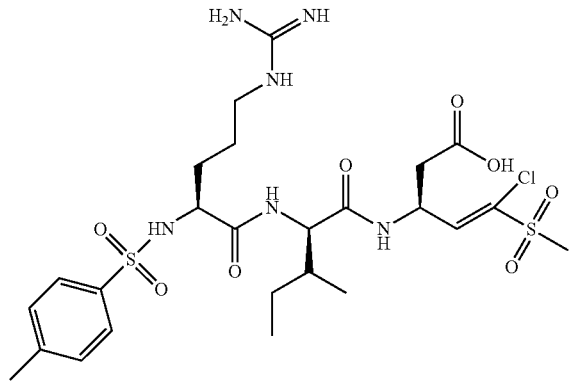
149. N-Tosyl Arg-Ile-Asp Ethyl Vinyl ester
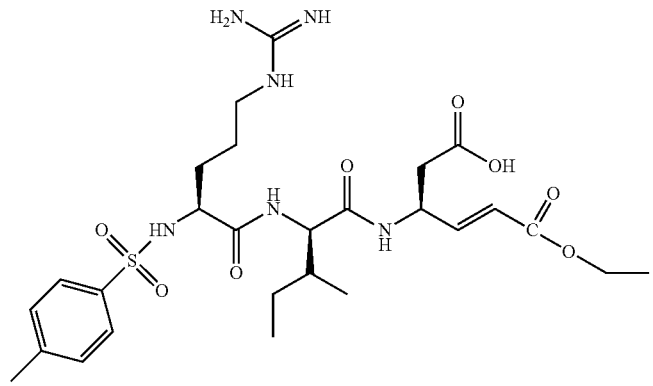

TABLE 1-continued
CPD NO./CPD NAME/STRUCTURE
150. N-Fmoc Arg-Ile-Asp methyl vinyl sulfone
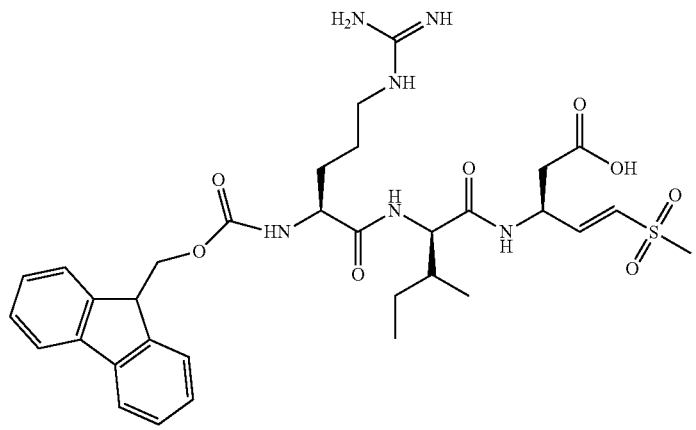
151. N-Fmoc Arg-Ile-Asp αchlorovinyl methyl vinyl sulfone
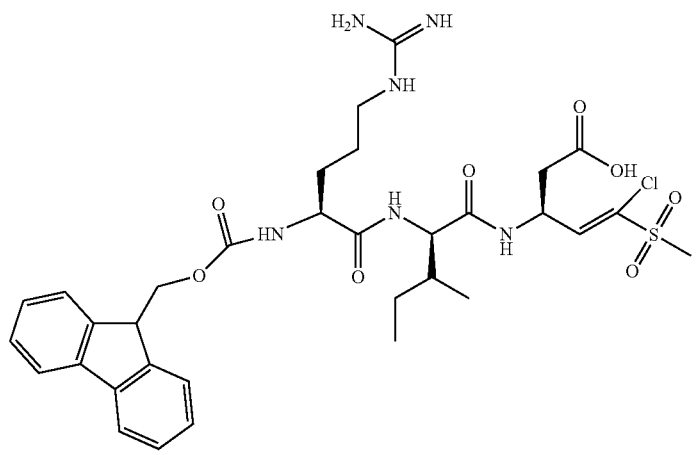
152. N-Fmoc Arg-Ile-Asp Ethyl Vinyl ester
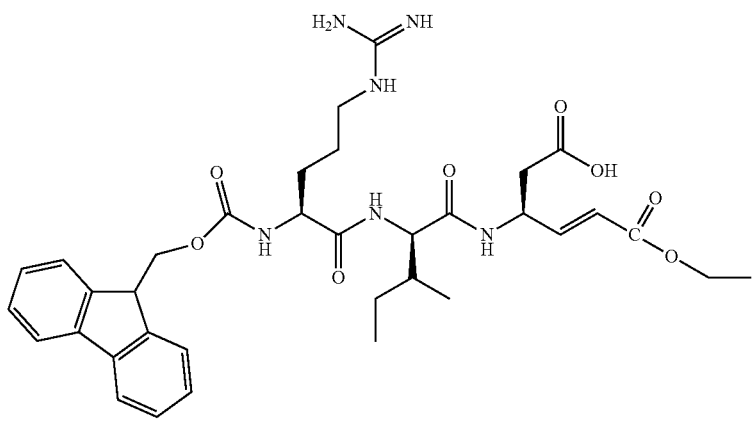

TABLE 1-continued
CPD NO./CPD NAME/STRUCTURE
153. N-Fmoc Arg-His-Asp Ethyl Vinyl ester
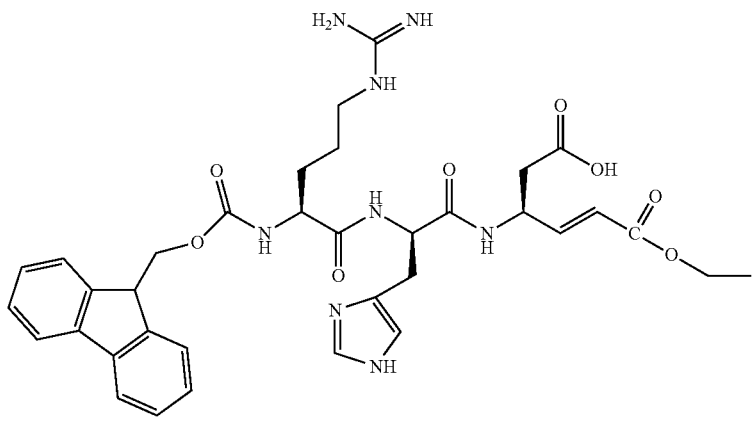
154. N-Fmoc Arg-His-Asp αchlorovinyl methyl vinyl sulfone
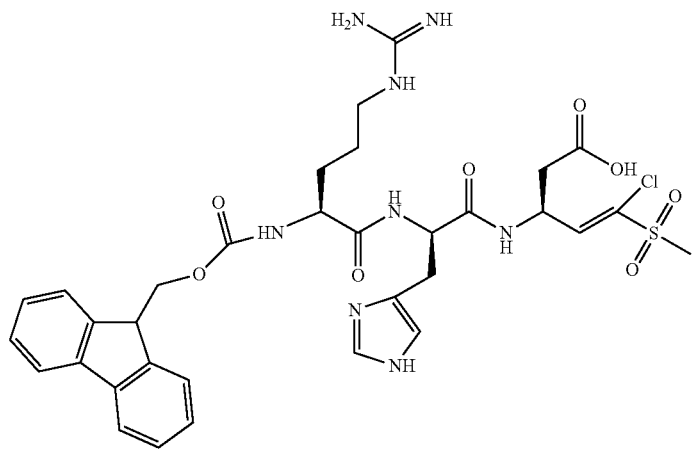
155. N-Fmoc Arg-His-Asp methyl vinyl sulfone
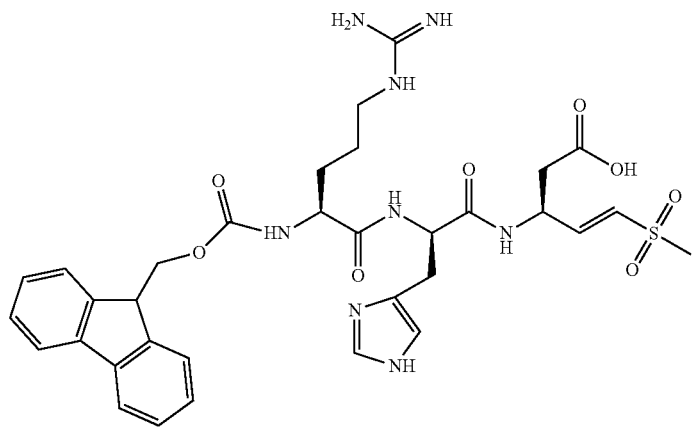

TABLE 1-continued
CPD NO./CPD NAME/STRUCTURE
156. N-Fmoc Glu-Ile-Asp Ethyl Vinyl ester
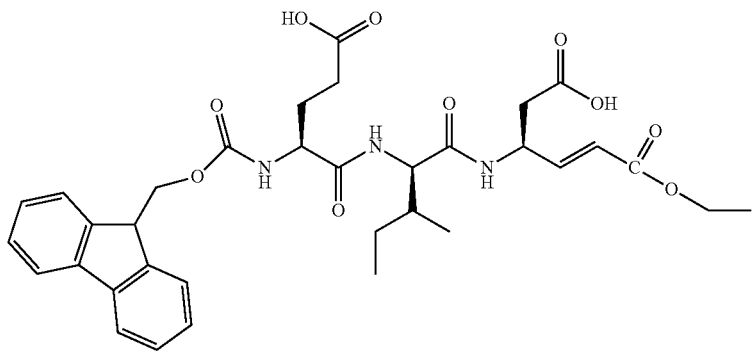
157. N-Fmoc Glu-Ile-Asp αchlorovinyl methyl vinyl sulfone
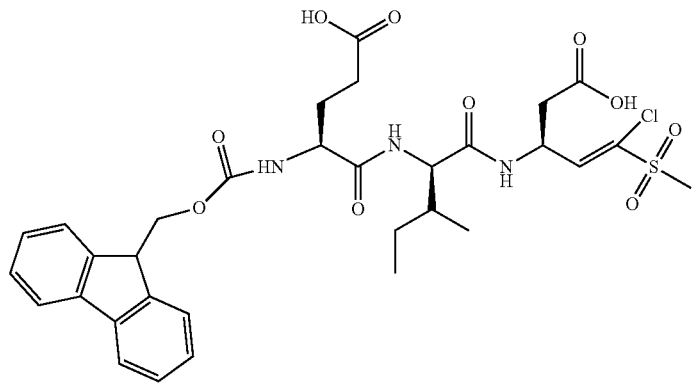
158. N-Fmoc Glu-Ile-Asp methyl vinyl sulfone
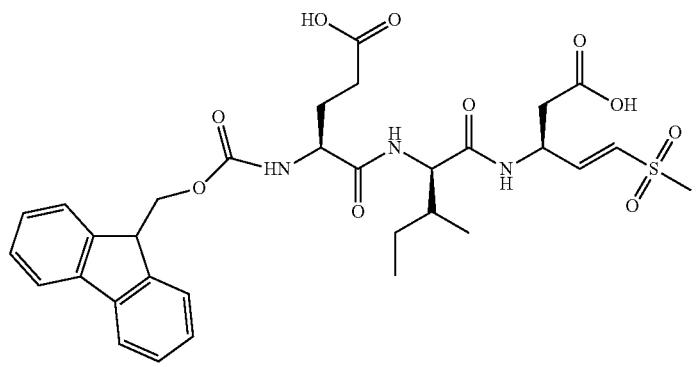

TABLE 1-continued
CPD NO./CPD NAME/STRUCTURE
159. N-Fmoc Glu-His-Asp Ethyl Vinyl ester
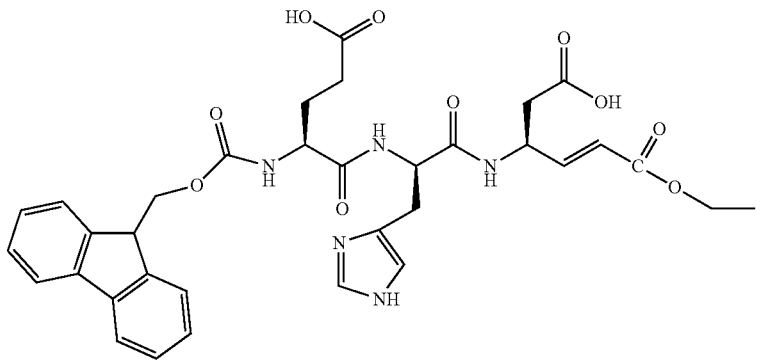
160. N-Fmoc Glu-His-Asp αchlorovinyl methyl vinyl sulfone
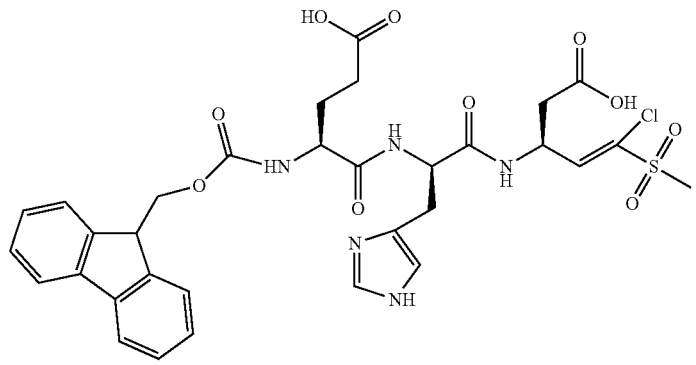
161. N-Fmoc Glu-His-Asp methyl vinyl sulfone
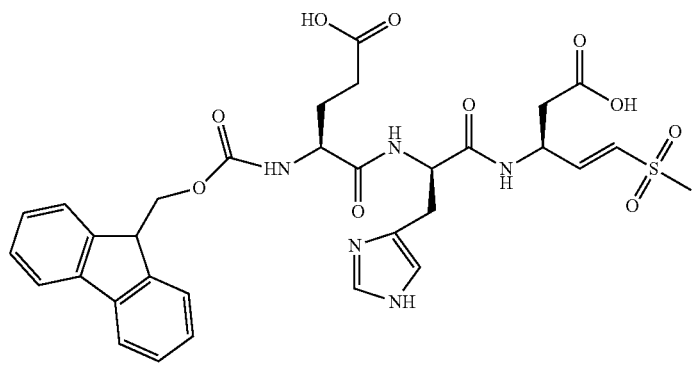

TABLE 1-continued

CPD NO./CPD NAME/STRUCTURE

162. N-Tosyl Glu-Ile-Asp αchlorovinyl methyl vinyl sulfone

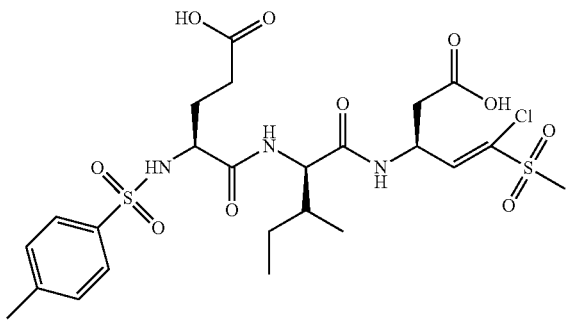

DEFINITIONS

Unless otherwise specified, the following definitions apply:

The singular forms "a", "an" and "the" include corresponding plural references unless the context clearly dictates otherwise.

As used herein, the term "comprising" is intended to mean that the list of elements following the word "comprising" are required or mandatory but that other elements are optional and may or may not be present.

As used herein, the term "consisting of" is intended to mean including and limited to whatever follows the phrase "consisting of". Thus the phrase "consisting of" indicates that the listed elements are required or mandatory and that no other elements may be present.

As used herein, the term "alkyl" is intended to include both branched and straight chain saturated aliphatic hydrocarbon groups having the specified number of carbon atoms, for example, $C_1$-$C_6$ as in $C_1$-$C_6$-alkyl is defined as including groups having 1, 2, 3, 4, 5 or 6 carbons in a linear or branched arrangement. Examples of $C_1$-$C_6$-alkyl and $C_1$-$C_4$ alkyl as defined above include, but are not limited to, methyl, ethyl, n-propyl, i-propyl, n-butyl, t-butyl, i-butyl, pentyl and hexyl.

As used herein, the term, "alkenyl" is intended to mean unsaturated straight or branched chain hydrocarbon groups having the specified number of carbon atoms therein, and in which at least two of the carbon atoms are bonded to each other by a double bond, and having either E or Z regiochemistry and combinations thereof. For example, $C_2$-$C_6$ as in $C_2$-$C_6$ alkenyl is defined as including groups having 1, 2, 3, 4, 5, or 6 carbons in a linear or branched arrangement, at least two of the carbon atoms being bonded together by a double bond. Examples of $C_2$-$C_6$ alkenyl include ethenyl (vinyl), 1-propenyl, 2-propenyl, 1-butenyl and the like.

As used herein, the term "cycloalkyl" is intended to mean a monocyclic saturated aliphatic hydrocarbon group having the specified number of carbon atoms therein, for example, $C_3$-$C_7$ as in $C_3$-$C_7$ cycloalkyl is defined as including groups having 3, 4, 5, 6, or 7 carbons in a monocyclic arrangement. Examples of $C_3$-$C_7$ cycloalkyl as defined above include, but are not limited to, cyclopropyl, cyclobutyl, cyclopentyl, cyclohexyl and cycloheptyl.

As used herein, the term "halo" or "halogen" is intended to mean fluorine, chlorine, bromine and iodine.

As used herein, the term "haloalkyl" is intended to mean an alkyl as defined above, in which each hydrogen atom may be successively replaced by a halogen atom. Examples of haloalkyls include, but are not limited to, $CH_2F$, $CHF_2$ and $CF_3$.

As used herein, the term "aryl", either alone or in combination with another radical, means a carbocyclic aromatic monocyclic group containing 6 carbon atoms which may be further fused to a second 5- or 6-membered carbocyclic group which may be aromatic, saturated or unsaturated. Aryl includes, but is not limited to, phenyl, indanyl, 1-naphthyl, 2-naphthyl and tetrahydronaphthyl. The aryls may be connected to another group either at a suitable position on the cycloalkyl ring or the aromatic ring.

As used herein, the term "heteroaryl" is intended to mean a monocyclic or bicyclic ring system of up to ten atoms, wherein at least one ring is aromatic, and contains from 1 to 4 hetero atoms selected from the group consisting of O, N, and S. The heteroaryl substituent may be attached either via a ring carbon atom or one of the heteroatoms. Examples of heteroaryl groups include, but are not limited to thienyl, benzimidazolyl, benzo[b]thienyl, furyl, benzofuranyl, pyranyl, isobenzofuranyl, chromenyl, xanthenyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalazinyl, napthyridinyl, quinoxalinyl, quinazolinyl, cinnolinyl, pteridinyl, isothiazolyl, isochromanyl, chromanyl, isoxazolyl, furazanyl, indolinyl, isoindolinyl, thiazolo[4,5-b]-pyridine, and fluoroscein derivatives.

As used herein, the term "heterocycle", "heterocyclic" or "heterocyclyl" is intended to mean a 5, 6, or 7 membered non-aromatic ring system containing from 1 to 4 heteroatoms selected from the group consisting of O, N and S. Examples of heterocycles include, but are not limited to pyrrolidinyl, tetrahydrofuranyl, piperidyl, pyrrolinyl, piperazinyl, imidazolidinyl, morpholinyl, imidazolinyl, pyrazolidinyl, and pyrazolinyl.

As used herein, the term "electron withdrawing group (EWG)" is intended to mean a functional group that allows nucleophilic attack by the thiol-group of a caspase at the alkene bond of the inhibitor as a result of the electron withdrawing properties of the EWG. The EWG is conjugated with the alkene bond, such that the electron withdrawing properties of the EWG allow nucleophilic attack by a caspase at the alkene bond, i.e. the alkene bond and the EWG are electronically conjugated. Thus, the covalent bond between the alkene bond and the EWG is a direct one, without intervening moieties that would prevent the electron withdrawing properties of the EWG from being exerted on the alkene bond.

As used herein, the term "detectable label" is intended to mean a group that may be linked to a compound of the present invention to produce a probe or to a caspase, such that when the probe is associated with the caspase, the label allows either direct or indirect recognition of the probe so that it may be detected, measured and quantified.

As used herein, the term "affinity tag" is intended to mean a ligand or group, which is linked to either a compound of the present invention or to a caspase to allow another compound to be extracted from a solution to which the ligand or group is attached.

As used herein, the term "probe" is intended to mean a compound of Formula I, IA, II, IIA, III, or IIIA, which is labeled with either a detectable label or an affinity tag, and which is capable of binding, either covalently or non-covalently, to a caspase. When, for example, the probe is non-covalently bound, it may be displaced by a test compound. When, for example, the probe is bound covalently, it may be used to form cross-linked adducts, which may be quantified and inhibited by a test compound.

As used herein, the term "optionally substituted with one or more substituents" or its equivalent term "optionally substituted with at least one substituent" is intended to mean that the subsequently described event of circumstances may or may not occur, and that the description includes instances where the event or circumstance occurs and instances in which it does not. The definition is intended to mean from zero to five substituents.

If the substituents themselves are incompatible with the synthetic methods of the present invention, the substituent may be protected with a suitable protecting group (PG) that is stable to the reaction conditions used in these methods. The protecting group may be removed at a suitable point in the reaction sequence of the method to provide a desired intermediate or target compound. Suitable protecting groups and the methods for protecting and de-protecting different substituents using such suitable protecting groups are well known to those skilled in the art; examples of which may be found in T. Greene and P. Wuts, Protecting Groups in Chemical Synthesis ($3^{rd}$ ed.), John Wiley & Sons, NY (1999), which is incorporated herein by reference in its entirety. Examples of protecting groups used throughout include, but are not limited to Fmoc, Bn, Boc, CBz and $COCF_3$. In some instances, a substituent may be specifically selected to be reactive under the reaction conditions used in the methods of this invention. Under these circumstances, the reaction conditions convert the selected substituent into another substituent that is either useful in an intermediate compound in the methods of this invention or is a desired substituent in a target compound.

Three and single letter abbreviations for natural α-amino acids used throughout are as follows:

| Amino acid | Abbreviation | Abbreviation |
|---|---|---|
| α-Amino butyric acid | Abu | — |
| Alanine | Ala | A |
| Arginine | Arg | R |

-continued

| Amino acid | Abbreviation | Abbreviation |
|---|---|---|
| Aspartic acid | Asp | D |
| Asparagine | Asn | N |
| Cysteine | Cys | C |
| Glutamic acid | Glu | E |
| Glutamine | Gln | Q |
| Glycine | Gly | G |
| Isoleucine | Ile | I |
| Histidine | His | H |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

A series of non natural amino acids which may be used in place of natural amino acids include, but are not limited to, 3-amino 2-hydroxy pyridine; (2-furyl)alanine; 1-amino-1-cyclohexane carboxylic acid; (2-thienyl)alanine; 2-aminobenzoic acid (2-Abz); 2-pyridylalanine; 1-amino-1-cyclopentanecarboxilic acid; 2-aminobutyric acid (2-Abu); 3-amino-3-phenylpropionic acid; aminocyclopentane carboxylic acid (ACPC); 4-aminomethylbenzoic acid (Amb); aminoisobutiric acid (Aib); p-benzoyl-1-phenylalanine (Bpa); allylglycine; 4-aminomethyl cyclohexane carboxylic acid (Amc); cyclohexyl-alanine (Cha); delta-valine; delta-leucine; cyanobbutylalanine (Cba); indanylglycine (Igl); 3-(1-naphtyl)-alanine; 3-(2-naphthyl)alanine (1-Nal); biphenylalanine (Bip); hydroxyproline (Hyp); isonipecotic acid (Inp); norvaline (Nva); 4-iodophenylalanine (Phe(pl)); 4-nitrophenylalanine; 4-methylphenylalanine; homophenylalanine (hPhe); 4-aminophenylalanine (Phe4NH(Boc); phenyl glycine; alanine(2'-quinolyl); alanine (2' pyridine); tryptophan; tryptophan N-Methyl; 2-azetidine carboxylic acid; pipecolic acid (Pip); propargylglycine; thioproline (Thz); butylglycine (Tle); 3-nitrotyrosine; 3-aminobenzoic acid (3-Abz); 3-amino-3-phenyl propionic acid; (1-indanylglycine); (2-indanylglycine); allyl glycine; 3-nitrotyrosine; 1,2,3,4-tetrahydroisoquinoline-3-carboxylic acid; beta amino acids; gamma amino acids; Asp (tert-butyl)-OH, 3,3-diphenyl-alanine; 3,3,3 dimethylphenyl-alanine; Asp(β ethyl); Glu (β-ethyl), Asp (β-methyl), Asp (β-tert butyl), Glu (β-tert butyl), Leu (O-phosphate), Serine (O-phosphate), Serine (phosphate), leucine phosphate derivatives. The side chains illustrated as $AA_X$, $AA_5$, $AA_4$, $AA_3$, $AA_2$ in the Formulae described above are the side chains of the aforesaid natural and non-natural amino acids.

As used herein, the term "residue" when referring to α-amino acids is intended to mean a radical derived from the corresponding α-amino acid by eliminating the hydroxyl of the carboxy group and one hydrogen of the α-amino group. For example, the terms Gln, Ala, Gly, Ile, Arg, Asp, Phe, Ser, Leu, Cys, Asn, and Tyr represent the residues of L-glutamine, L-alanine, glycine, L-isoleucine, L-arginine, L-aspartic acid, L-phenylalanine, L-serine, L-leucine, L-cysteine, L-asparagine, and L-tyrosine, respectively.

As used herein the term "amino acid side chain" is intended to mean the part of an amino acid's chemistry that differentiates it from other amino acids. Amino acid structure includes a carboxyl group, an amine group plus the individual side chain. Each amino acid has a unique side chain. This is applied to non-natural amino acids as well. This side chain may exist in protected form or not.

As used herein, the term "prodrug" is intended to mean a compound that may be converted under physiological conditions or by solvolysis to a biologically active compound of the present invention. Thus, the term "prodrug" refers to a precursor of a compound of the invention that is pharmaceutically acceptable. A prodrug may be inactive or display limited activity when administered to a subject in need thereof, but is converted in vivo to an active compound of the present invention. Typically, prodrugs are transformed in vivo to yield the compound of the invention, for example, by hydrolysis in blood or other organs by enzymatic processing. The prodrug compound often offers advantages of solubility, tissue compatibility or delayed release in the subject (see, Bundgard, H., Design of Prodrugs (1985), pp. 7-9, 21-24 (Elsevier, Amsterdam). The definition of prodrug includes any covalently bonded carriers which release the active compound of the invention in vivo when such prodrug is administered to a subject. Prodrugs of a compound of the present invention may be prepared by modifying functional groups present in the compound of the invention in such a way that the modifications are cleaved, either in routine manipulation or in vivo, to a parent compound of the invention.

As used herein, the term "pharmaceutically acceptable salt" is intended to mean both acid and base addition salts.

As used herein, the term "pharmaceutically acceptable acid addition salt" is intended to mean those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid and the like, and organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

As used herein, the term "pharmaceutically acceptable base addition salt" is intended to mean those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like.

The compounds of the present invention, or their pharmaceutically acceptable salts may contain one or more asymmetric centers, chiral axes and chiral planes and may thus give rise to enantiomers, diastereomers, and other stereoisomeric forms and may be defined in terms of absolute stereochemistry, such as (R)- or (S)- or, as (D)- or (L)- for amino acids. The present invention is intended to include all such possible isomers, as well as, their racemic and optically pure forms. Optically active (+) and (−), (R)- and (S)-, or (D)- and (L)-isomers may be prepared using chiral synthons or chiral reagents, or resolved using conventional techniques, such as reverse phase HPLC. The racemic mixtures may be prepared and thereafter separated into individual optical isomers or these optical isomers may be prepared by chiral synthesis. The enantiomers may be resolved by methods known to those skilled in the art, for example by formation of diastereoisomeric salts which may then be separated by crystallization, gas-liquid or liquid chromatography, selective reaction of one enantiomer with an enantiomer specific reagent. It will also be appreciated by those skilled in the art that where the desired enantiomer is converted into another chemical entity by a separation technique, an additional step is then required to form the desired enantiomeric form. Alternatively specific enantiomers may be synthesized by asymmetric synthesis using optically active reagents, substrates, catalysts, or solvents or by converting one enantiomer to another by asymmetric transformation.

Certain compounds of the present invention may exist as a mix of epimers. Epimers means diastereoisomers that have the opposite configuration at only one of two or more stereogenic centers present in the respective compound.

Certain compounds of the present invention may exist in Zwitterionic form and the present invention includes Zwitterionic forms of these compounds and mixtures thereof.

In addition, the compounds of the invention also may exist in hydrated and anhydrous forms. Hydrates of the compound of any of the formulas described herein are included as compounds of the invention. In a further embodiment, the compound according to any of the formulas described herein is a monohydrate. In one embodiment, the compound of the invention comprises about 10% or less, about 9% or less, about 8% or less, about 7% or less, about 6% or less, about 5% or less, about 4% or less, about 3% or less, about 2% or less, about 1% or less, about 0.5% or less, about 0.1% or less by weight of water. In another embodiment, the compounds of the invention comprise, about 0.1% or more, about 0.5% or more, about 1% or more, about 2% or more, about 3% or more, about 4% or more, about 5% or more, or about 6% or more by weight of water.

C) Methods of Preparation

General and particular methods for the synthesis of the compounds of the present invention are shown below and are disclosed merely for the purpose of illustration and are not meant to be interpreted as limiting the processes to make the compounds by any other methods. Those skilled in the art will readily appreciate that a number of methods are available for the preparation of the compounds of the present invention.

Example A compound of Formula 2b can be prepared by the procedure described below

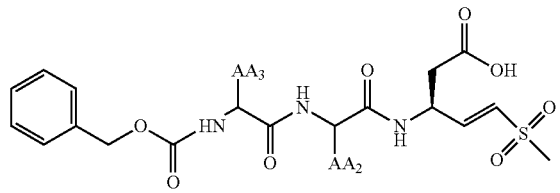

Formula 2b i) Coupling Step Synthesis

The coupling step between Asp methyl vinylsulfone salt and the peptide in the presence of coupling reagents such (isobutyl chloroformate, NMM) results in Asp methyl vinylsulfone tri-peptide derivative.

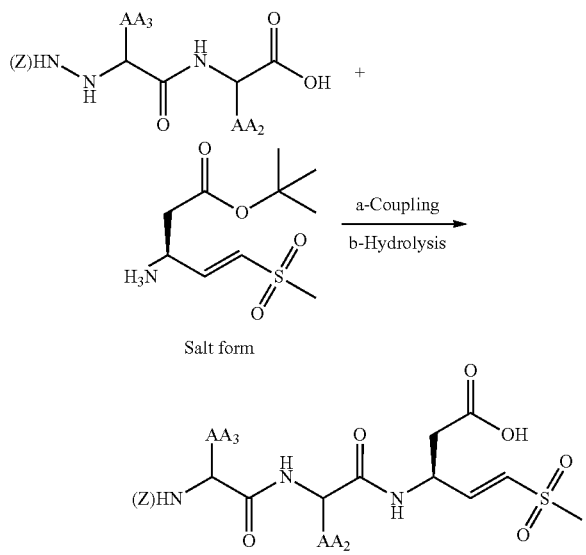

A compound of Formula 2c can be prepared by the procedure described below

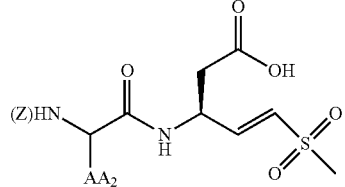

Formula 3c i) Coupling Step Synthesis

The coupling step between Asp methyl vinylsulfone salt and the peptide in the presence of coupling reagents such (isobutyl chloroformate, NMM) results in Asp methyl vinylsulfone di-peptide derivative.

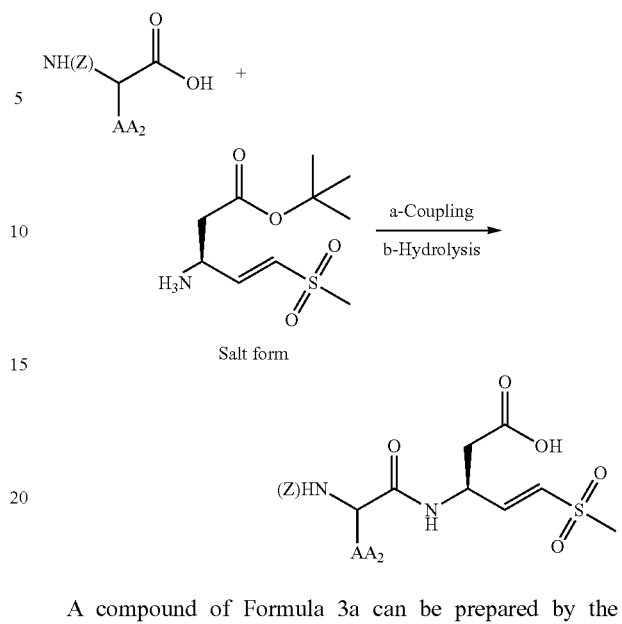

A compound of Formula 3a can be prepared by the procedure described below

Formula 3a

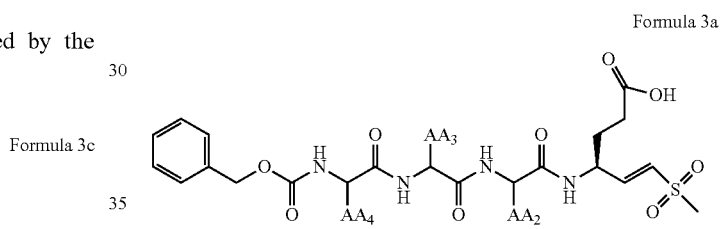

i) Right Arm Synthesis

The suicide substrate proposed in the following scheme is Glu methyl vinylsulfone.

The common intermediate Boc-Glu (B-tert-butyl)-H is synthesized from Boc-Glu (B-tert-butyl)-N-hydroxysuccinimide ester. Treatment of the aldehyde with sodium anion of Diethyl (methylsulfone) methyl phosphonate results in the corresponding Boc-Glu (β-tert-butyl) methylvinylsulfone in the manner of Wadsworth and Emmons.

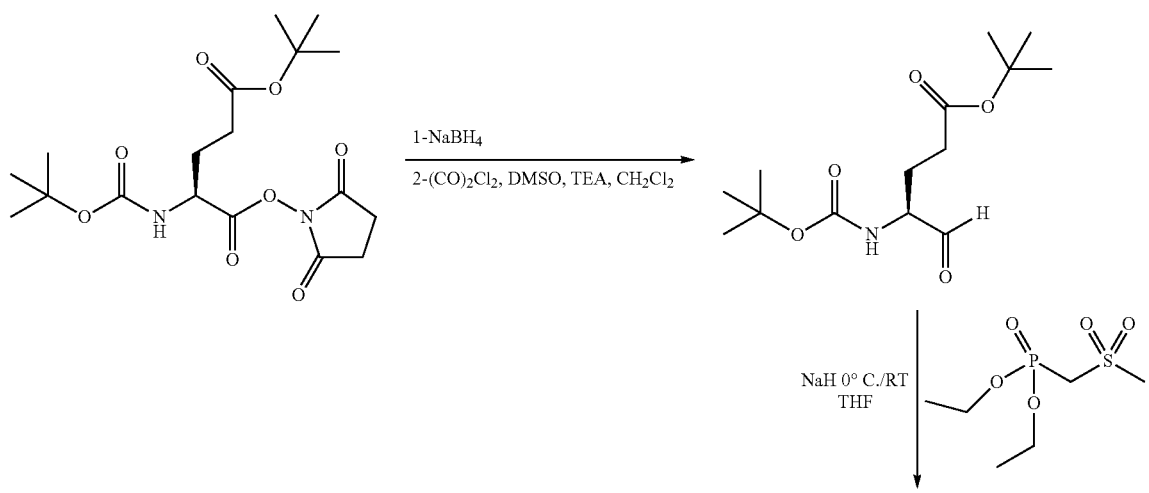

-continued

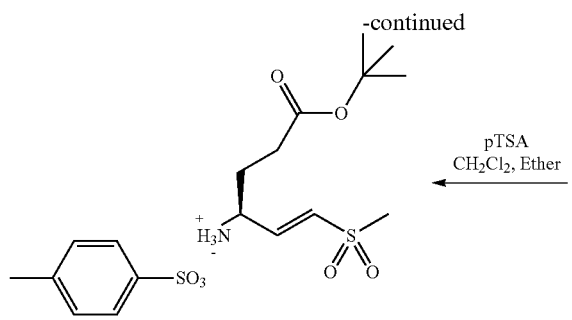 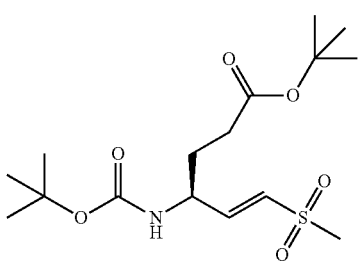

ii) Coupling Step Synthesis

The coupling step between Glu(O-tBu) methyl vinylsulfone salt and the peptide in the presence of coupling reagents such (isobutyl chloroformate, NMM) results in Glu methyl vinylsulfone peptide derivative.

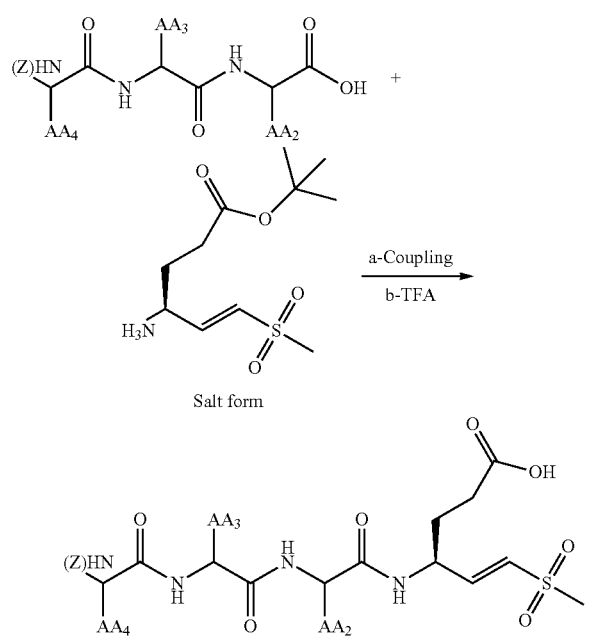

A compound of Formula 3b can be prepared by the procedure described below

Formula 3b

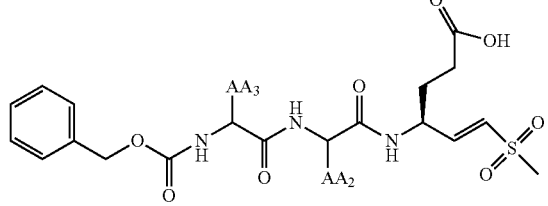

i) Coupling Step Synthesis

The coupling step between Glu(O-tBu) methyl vinylsulfone salt and the peptide in the presence of coupling reagents such (isobutyl chloroformate, NMM) results in Glu methyl vinylsulfone tri-peptide derivative.

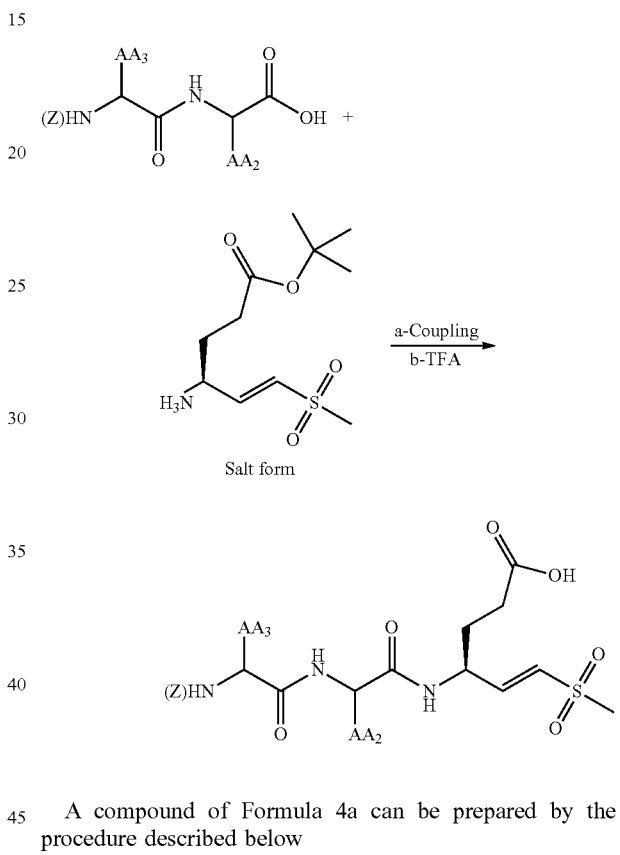

A compound of Formula 4a can be prepared by the procedure described below

Formula 4a i) Right Arm Synthesis

The suicide substrate proposed in the following scheme is (B-terazoleGlycine) methyl vinylsulfone. The common intermediate Boc-(B-terazoleGlycine)-H is synthesized from Boc-(B-Cynao-Glycine)-OCH₃. Treatment of the aldehyde with sodium anion of Diethyl (methylsulfone) methyl phosphonate could result in the corresponding Boc-(B-terazoleGlycine) methylvinylsulfone in the manner of Wadsworth and Emmons.

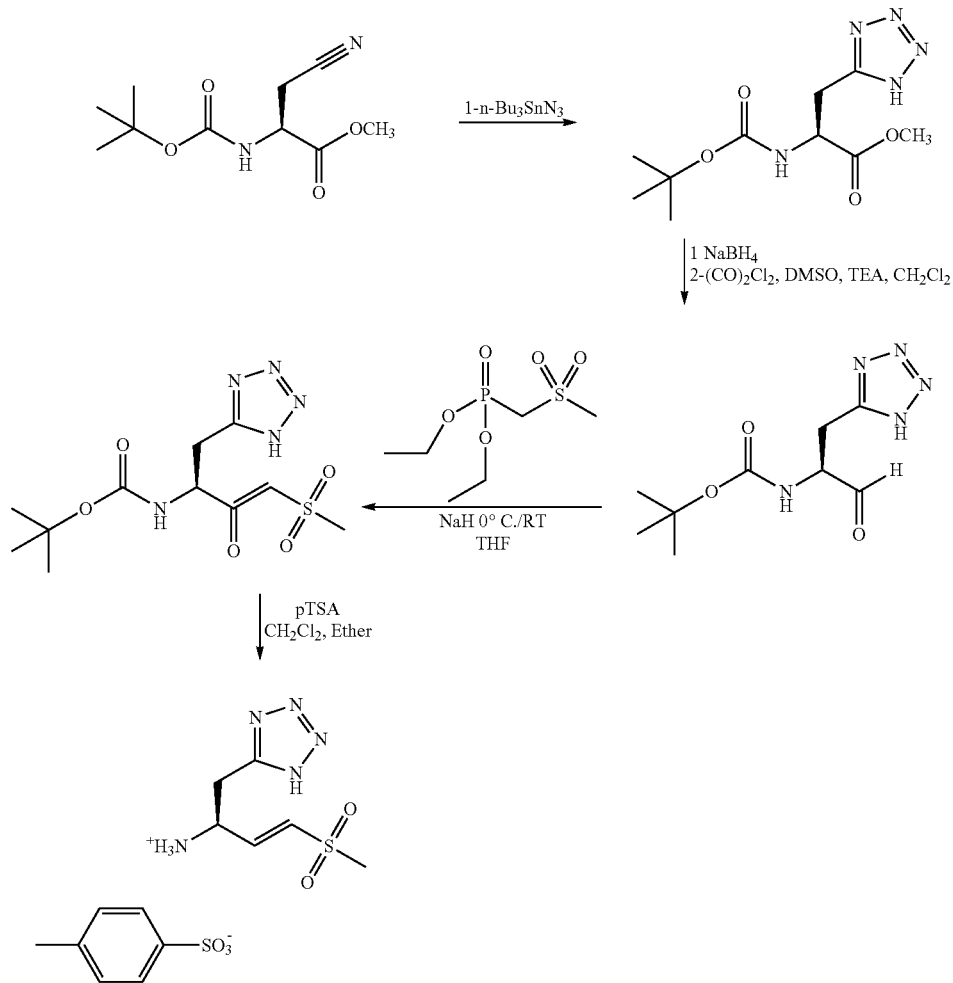

ii) Coupling Step Synthesis

The coupling step between B-terazoleGlycine methyl vinylsulfone salt and the peptide in the presence of coupling reagents such (isobutyl chloroformate, NMM) could result in B-terazoleGlycine methyl vinylsulfone tetra-peptide derivative.

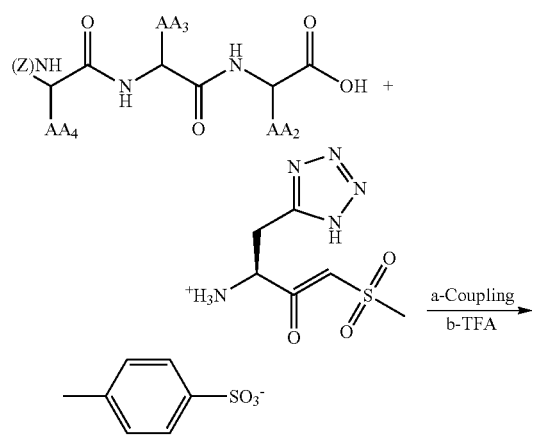

-continued

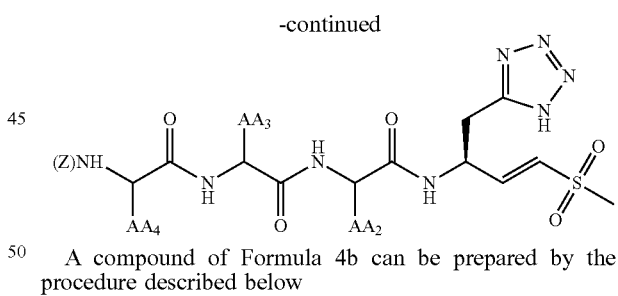

A compound of Formula 4b can be prepared by the procedure described below

Formula 4b

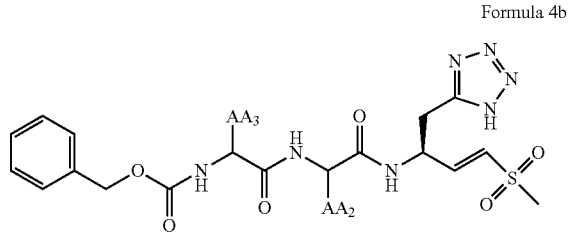

i) Coupling Step Synthesis

The coupling step between B-terazoleGlycine methyl vinylsulfone salt and the peptide in the presence of coupling reagents such (isobutyl chloroformate, NMM) could result in B-terazoleGlycine methyl vinylsulfone tri-peptide derivative.

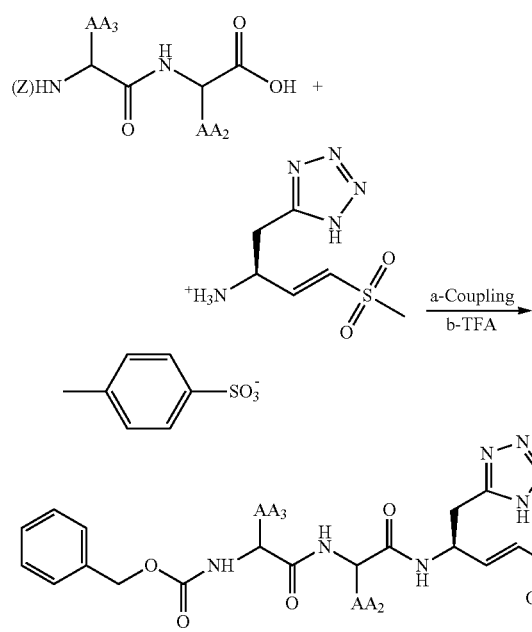

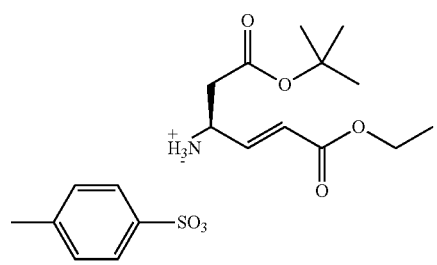

ii) Coupling Step Synthesis

The coupling step between Asp Ethyl Vinyl Ester Salt and the peptide in the presence of coupling reagents such (isobutyl chloroformate, NMM) resulted in Asp Ethyl Vinyl Ester tetra-peptide derivative.

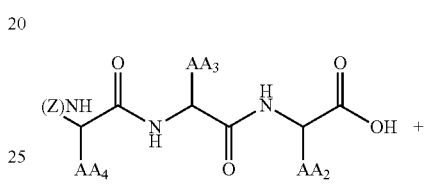

Formula 5a

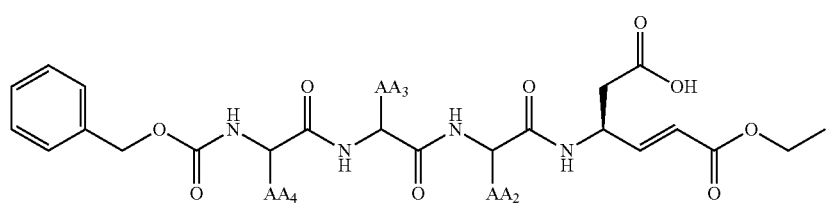

A compound of Formula 5a can be prepared by the procedure described below i) Right Arm Synthesis The suicide substrate proposed in the following scheme is Asp Ethyl Vinyl Ester.

The common intermediate Boc-Asp(B-tert-butyl)-H is synthesized from Boc-Asp(B-tert-butyl)-N-hydroxysuccinimide ester as reported by (Mancuso A et al., 1981, William R. Ewing et al., 1999 and Won Bum Jang. 2004).

Treatment of the aldehyde with sodium anion of Triethylphosphonoacetate results in the corresponding Boc-Asp (β-tert-butyl) Ethyl Vinyl Ester in the manner of Wadsworth and Emmons, 1961 and Palmer et al. 1995.

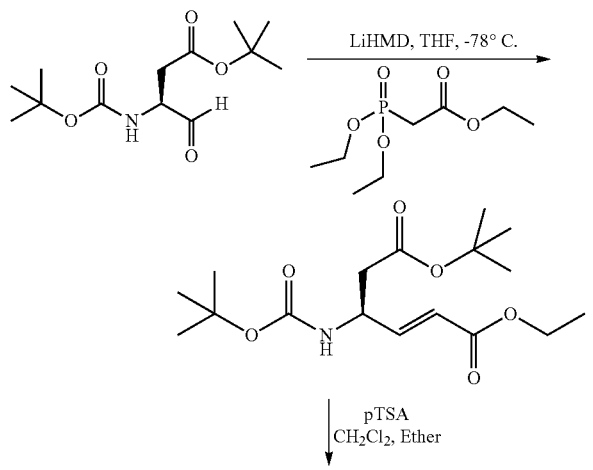

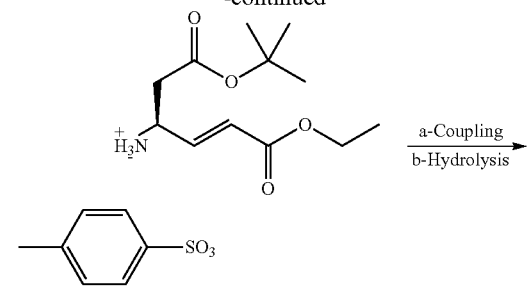

A compound of Formula 5b can be prepared by the procedure described below

Formula 5b

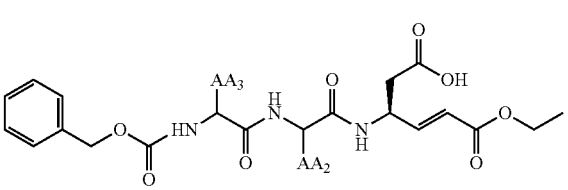

i) Coupling Step Synthesis

The coupling step between Asp Ethyl Vinyl Ester tetra-peptide salt and the peptide in the presence of coupling reagents such (isobutyl chloroformate, NMM) resulted in Asp Ethyl Vinyl Ester tri-peptide.

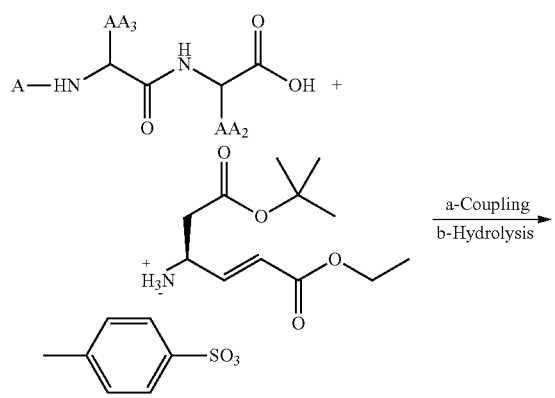

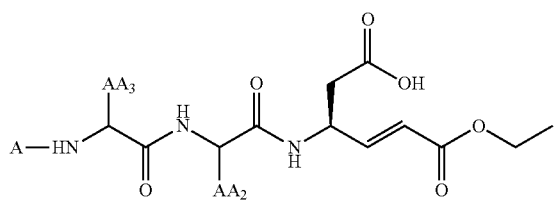

General Method to Generate Other Peptide Asp-Vinyl Electrowithdrawing Groups.

1-Vinyl Phosphonates i) Right Arm Synthesis

Treatment of Boc-Asp(ß-tert-butyl)-H with sodium anion of tetraethyl methylene diphosphonate derivatives could result in the corresponding Boc-Asp(β-tert-butyl) vinyl phosphonate derivatives in the manner of Wadsworth and Emmons.

The vinyl phosphonate derivatives could be deprotected with Tosyl acid to form the corresponding salt and coupled with the appropriate peptide to form the corresponding peptide Asp vinyl phosphonate derivatives.

ii) Coupling Step Synthesis

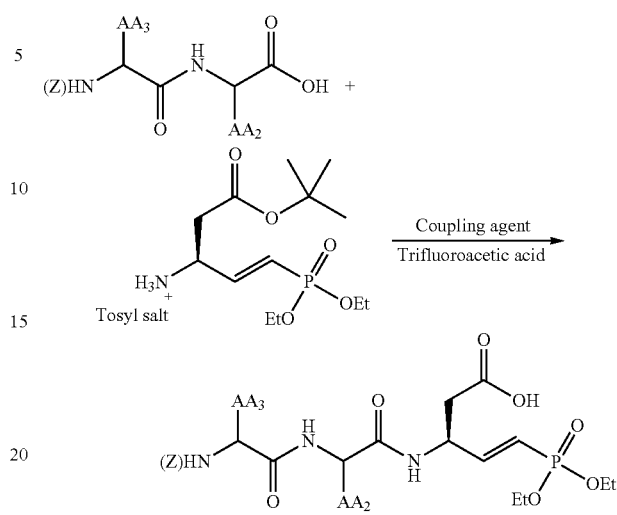

2-Vinyl Nitrites i) Right Arm Synthesis

Treatment of Boc-Asp(ß-tert-butyl)-H with sodium anion of diethyl cyanomethylphosphonate derivatives could result in the corresponding Boc-Asp (β-tert-butyl) vinyl nitrites derivatives in the manner of Wadsworth and Emmons.

The vinyl nitrites derivatives could be deprotected with Tosyl acid to form the corresponding salt and coupled with the appropriate peptide to form the corresponding peptide Asp vinyl nitrites derivatives

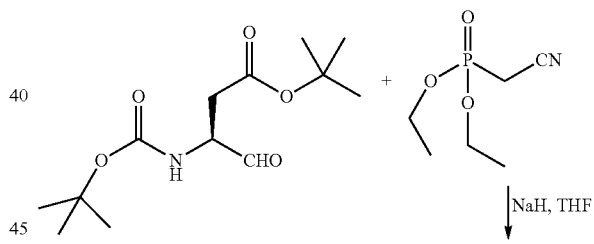

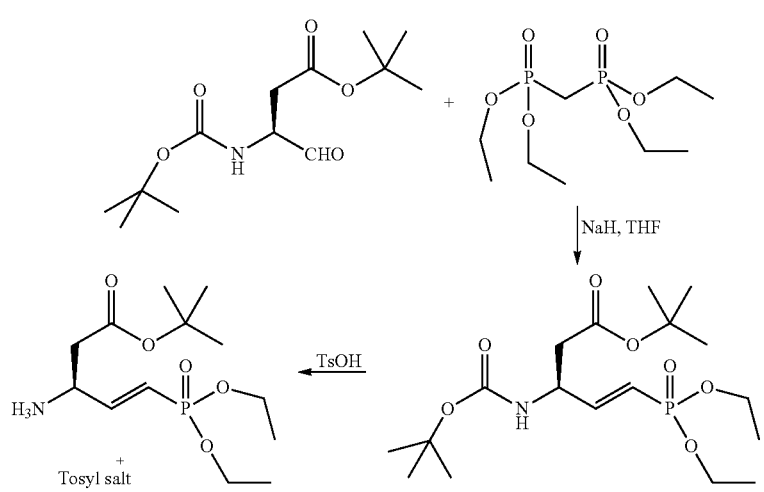

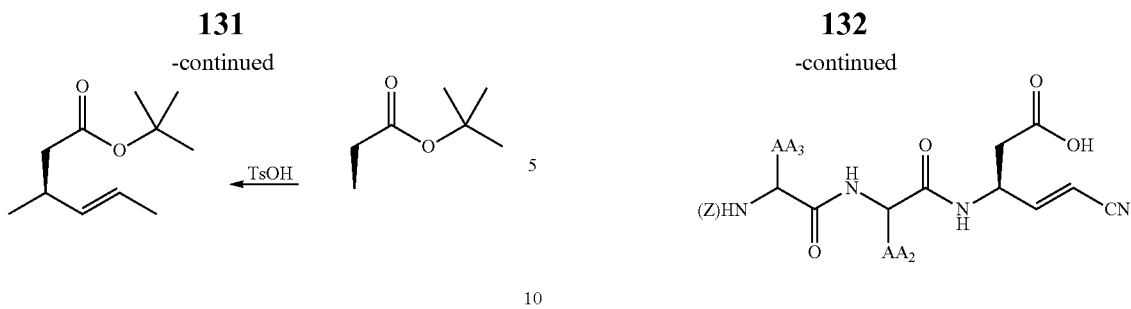

ii) Coupling Step Synthesis

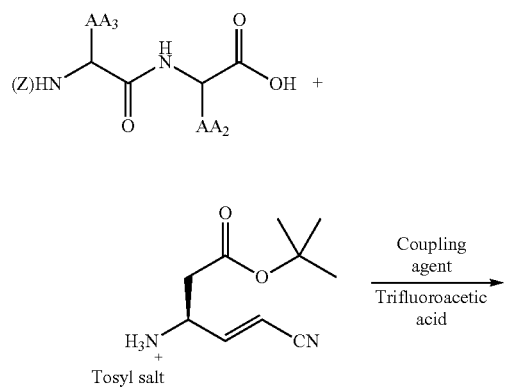

3-Diene Sulfone i) Right Arm Synthesis

Treatment of Boc-Asp(ß-tert-butyl)-H with (triphenyl-phosphoranylidene)acetaldehyde in toluene result in the corresponding Boc-Asp (β-tert-butyl) vinyl acetaldehyde derivatives in the manner of Wadsworth and Emmons. The sodium anion of Diethyl (methylsulfone) phosphonate derivatives could react with Boc-Asp (β-tert-butyl) vinylacetaldehyde derivatives in the manner of Wadsworth and Emmons to form the corresponding cis and trans diene sulfone derivative.

The diene sulfone derivatives could be deprotected with Tosyl acid to form the corresponding salt and coupled with the appropriate peptide to form the corresponding peptide Asp diene sulfone derivatives.

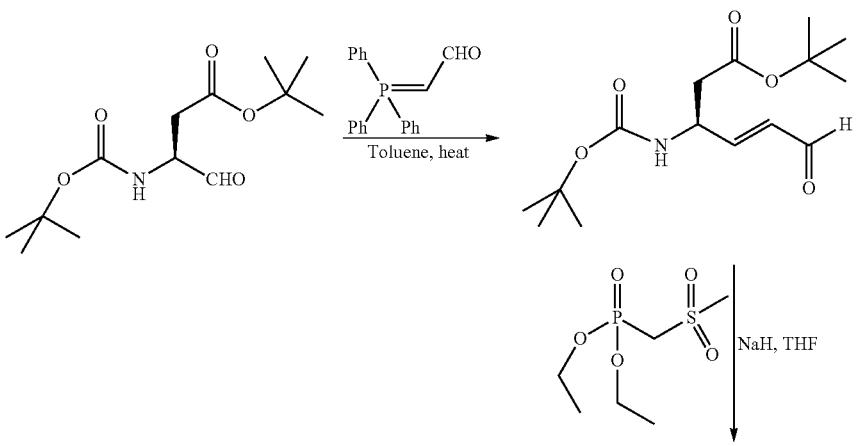

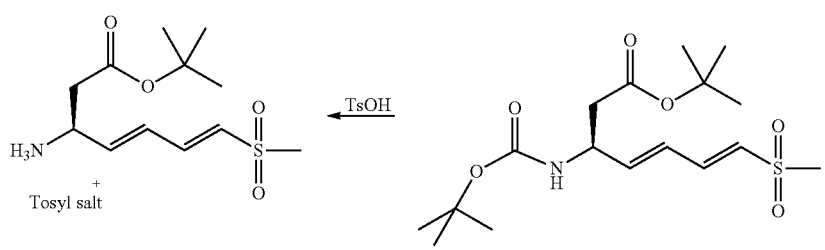

ii) Coupling Step Synthesis

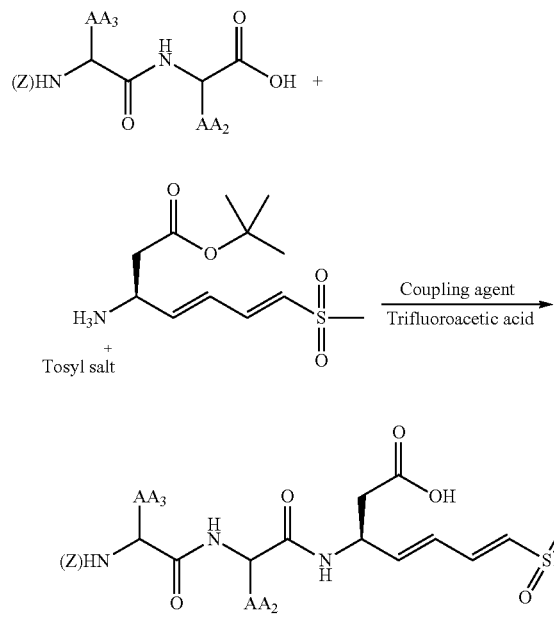

4-Vinyl Amide
i) Right Arm Synthesis

Vinyl amide could be obtained by coupling diethyl phosphonoacetic acid with natural and unnatural amino acids (Ex: Glycine methyl ester or tert butyl) to form the diethyl phosphonoacetyl glycine methyl ester which upon treatment with NaH reacts with Boc-Asp(ß-tert-butyl)-H to form the corresponding Boc-Asp (β-tert-butyl) vinyl amide. N-deprotection of Boc-Asp (β-tert-butyl) vinyl amide followed with coupling reaction with the appropriate peptide could afford the corresponding peptide Asp vinyl amide derivatives.

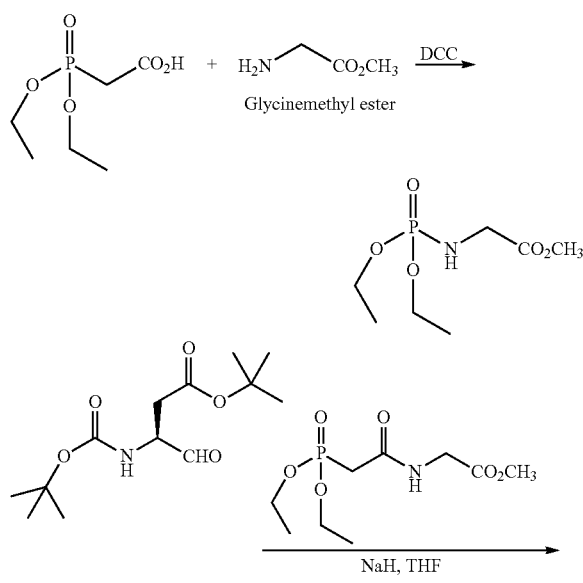

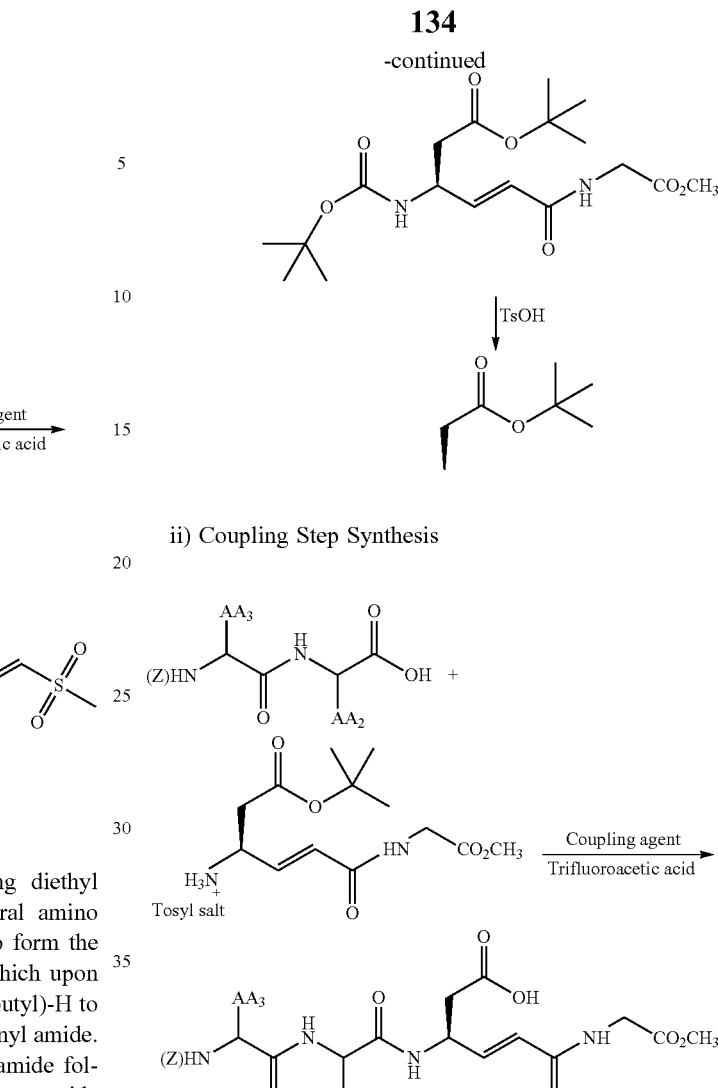

ii) Coupling Step Synthesis

D) Development of Specific Caspase Inhibitors

An additional aspect of the invention relates to a method for designing caspase inhibitors. Following the same approach as outlined hereinafter, those skilled in the art will appreciate that it is conceivable to further improve the potency of the compounds of Formula I, e.g.

2-Quinoline carbonyl-t-Leu-pro-Asp methyl vinyl sulfone (Compound 6) inhibits selectively caspase-1 over other caspases such as caspase-2, caspase-8, and caspase-3. As is known, all caspases cleave substrates to the right of the aspartic acid amino acid in position P1. However, caspase-3 requires an additional Asp at position P4, which confers caspase-3 its specificity. As shown in Table 2, Z-Asp-Phg-Val-Asp Ethyl Vinyl Ester (compound 105) proved to be very potent against caspase-3 (27 nM), and potent against Caspase-1 (1050 nM), Caspase-7 (145 nM), caspase8 (2624 nM), caspase-9 (994 nM) and caspase-10 (592 nM). The class of Ethyl Vinyl ester peptide showed very strong potency against caspases as well.

As shown in Table 3 hereinafter, monopeptide suicide substrates such as Asp αchlorovinyl methyl vinyl sulfone, Tosyl salt (Compound 4) showed inhibition against caspase-10 (43%) at 100 uM.

The di-peptide suicide substrates Z-Val-Asp αchlorovinyl methyl vinyl sulfone (Compound 2) showed inhibition against caspase-7 (60%), caspase-3 (39%), caspase-9 (66%), caspase-8 (49%) and caspase-10 (48%) at 100 uM.

As shown in Table-2 Compounds 123 (Z-Val-Glu-Ile-Asp-αchlorovinyl methyl vinyl sulfone) and 124 (Z-Val-Glu-Ile-Asp Ethyl Vinyl ester) exhibited inhibition against Caspase-6 (229 nM) and (293 nM) respectively. Compound 126 (Z-Val-Glu-Phg-Asp-Ethyl Vinyl ester) exhibited selective inhibition against both caspase initiators Caspase-8 (79 nM) and Caspase-10 (2 nM). Compound 124 (Z-Val-Glu-Ile-Asp Ethyl Vinyl ester) is a pan-caspase inhibitor.

Z-Asp-t-Leu-Pro-Asp-methyl vinyl sulfone (compound 26), proved to be a very potent inhibitor of caspase-3 with an $IC_{50}$ 123 nM, caspase-7 (378 nM), caspase-9 (662 nM), caspase-10 (161 nM. Replacement of t-Leu at position P3 by Phg (compound 30) affected the potency against caspase-3 (3410 nM) and more seriously the activity of the other caspases. Replacement of t-Leu at position P3 (compound 26) by Cyclopropylglycine (compound 28) affected the potency against caspase-3 by 7 fold and more seriously the activity of the other caspases. Replacement of Pro at position P2 by 2-Azetidine (compound 32) did not affect the potency against caspase-3, but affected seriously the activity of the other caspases.

Changes in Position P4

Changes in position P4 can also affect the selectivity of a given inhibitor. The amino acid that has been showed to fit well into the corresponding caspase-1 pockets at position P4 is Tryptophan. Therefore, Z-Trp-Glu-Val-Asp-methyl vinyl sulfone (compound 40) was tested against different caspases, and it proved to be selective against caspase-1 (26 nM). The amino acid that has been showed to fit well into the corresponding caspase-1 pockets at position P3 is glutamic acid.

The P4 of compound 26 could be replaced by a cap to generate tri-peptide EWG (electron withdrawing group). The replacement of aspartic acid in P4 position of compound 26 by quinaldic acid lead to 2-Quinoline carbonyl-t-Leu-pro-Asp methyl vinyl sulfone (compound 6) which proven to be very potent against caspase-1 (42 nM) and potent against caspase-4 (1549 nM), caspase-5 (2320 nM). The replacement of aspartic acid in P4 position by 2-Quinoline carbonyl-t-Leu-pro-Asp methyl vinyl sulfone lead to (4-amino-3-chlorobenzene carbonyl)-t-Leu-Pro-Asp methyl vinyl sulfone (compound 14) which proven to be very potent against caspase-1 (19 nM) and potent against caspase-4 (87 nM), caspase-5 (563 nM), caspase-9 (2311 nM), caspase-10 (2671 nM) and caspase-8 (12.8 uM). The replacement of aspartic acid vinyl sulfone in P1 position of compound 6 by Asp Ethyl Vinyl ester proven to be very potent against caspase-1 as well (31 nM) and showed better potency against caspase-4 (588 nM), caspase-9 and caspase-10.

These specific examples demonstrate that it is possible to make shorter peptide EWG to target selectively caspase-1 or two groups of caspases. Following the same approach as outlined hereinafter, it is conceivable to inhibit selectively additional caspases and to further improve the potency against selected caspases.

D) Pharmaceutical Applications

As indicated hereinbefore and exemplified hereinafter, the compounds of the invention have beneficial pharmaceutical properties and these compounds may have pharmaceutical applications in the prevention and/or treatment of various diseases and conditions in a subject. Medical and pharmaceutical applications contemplated by the inventors include, but are not limited to, cysteine protease-mediated diseases, including caspase-mediated diseases. In addition, the compounds of the present invention may have useful benefits on cells in vitro such as promoting cell survival or the health of the cells.

The term "subject" includes living organisms in a caspase-mediated disease can occur, or which are susceptible to such conditions. The term "subject" includes animals (e.g., mammals (e.g., cats, dogs, horses, pigs, cows, goats, sheep, rodents (e.g., mice or rats), rabbits, squirrels, bears, primates (e.g., chimpanzees, monkeys, gorillas, and humans)), as well as avians (e.g. chickens, ducks, Peking ducks, geese), and transgenic species thereof. Preferably, the subject is a mammal. More preferably, the subject is a human. Even more preferably, the subject is a human patient in need of treatment.

The term "caspase-mediated disease" includes all diseases, disorder and/or conditions in which any one or more of caspase-1, -2, -3, -4, -5, -6, -7, -8, -9, -10, -11, -12, -13, -14 plays a significant role. In some embodiments, the caspase-mediated disease mainly involves executioner caspases (caspase-3, 6, 7). In another embodiment, the caspase-mediated disease mainly involves initiators (caspase-2, 8, 9, 10). In another embodiment, the caspase-mediated disease mainly involves proinflammatory caspases (caspase-1, 4, 5). In some embodiments, a compound of the invention shows a high specificity towards one particular caspase. In another embodiment, a compound of the invention is able to inhibit two or more groups of caspases. Yet, in another embodiment, a compound of the invention even is able to inhibit two or more specific caspases belonging to two or more different groups of caspases.

Examples of cysteine protease-mediated diseases and caspase-mediated diseases according to the invention includes, but are not limited to, apoptosis-mediated diseases, IL-1 mediated diseases, inflammatory diseases, autoimmune diseases, autoinflammatory diseases, proliferative diseases, infectious diseases, degenerative diseases, retinal disorders, inflammatory peritonitis, osteoarthritis, pancreatitis, asthma, respiratory distress syndrome, rheumatoid arthritis, systemic lupus erythematosus, scleroderma, Grave's disease, autoimmune gastritis, diabetes, autoimmune hemolytic anemia, autoimmune neutropenia, thrombocytopenia, hepatitis, inflammatory bowel disease, Crohn's disease, psoriasis, dermatitis, Graft vs. host disease, organ transplant rejection, osteoporosis, leukemias and related disorders, multiple myeloma-related diseases, cancer, metastatic cancer, lung cancer, metastatic melanomas, Kaposi's sarcoma, sepsis, septic shock, Alzheimer's disease, Parkinson's disease, Huntington's disease, cerebral ischemia, epilepsy, myocardial ischemia, acute and chronic heart disease, myocardial infarction, congestive heart failure, atherosclerosis, spinal muscular atrophy, amyotrophic lateral sclerosis, multiple sclerosis, HIV-related encephalitis, aging, neurological damage due to stroke, ulcerative colitis, traumatic brain injury, spinal cord injury, hepatitis-B, hepatitis-C, hepatitis-G, liver-related diseases, renal disease, and HIV infection.

As used herein, "preventing" or "prevention" is intended to refer to at least the reduction of likelihood of the risk of (or susceptibility to) acquiring a disease or disorder (i.e., causing at least one of the clinical symptoms of the disease not to develop in a patient that may be exposed to or predisposed to the disease but does not yet experience or display symptoms of the disease). Biological and physiological parameters for identifying such patients are provided herein and are also well known by physicians.

The terms "treatment" or "treating" of a subject includes the application or administration of a compound of the invention to a subject (or application or administration of a compound of the invention to a cell or tissue from a subject) with the purpose of stabilizing, curing, healing, alleviating, relieving, altering, remedying, less worsening, ameliorating, improving, or affecting the disease or condition, the symptom of the disease or condition, or the risk of (or susceptibility to) the disease or condition. The term "treating" refers to any indicia of success in the treatment or amelioration of an injury, pathology or condition, including any objective or subjective parameter such as abatement; remission; lessening of the rate of worsening; lessening severity of the disease; stabilization, diminishing of symptoms or making the injury, pathology or condition more tolerable to the subject; slowing in the rate of degeneration or decline; making the final point of degeneration less debilitating; or improving a subject's physical or mental well-being. In some embodiments, the term "treating" can include increasing a subject's life expectancy and/or delay before additional treatments are required.

Addressing caspase-mediated diseases is among the medical and pharmaceutical applications contemplated by present invention. Therefore, in one of its aspects the present invention relates to methods, compounds and compositions for prevention and/or treatment of a caspase-mediated disease in a subject, preferably a human patient in need thereof.

Another aspect of the invention relates to the use of the compounds described herein for inhibiting a caspase or a caspase-like protein in a cell, comprising contacting the caspase or caspase-like protein with an effective amount of a caspase inhibitor according to the invention.

In some embodiments, the subject may be suffering from a viral infection. Therefore, the invention also relates to a method for the prophylaxis or therapy of a viral infection, comprising administering to a subject in need thereof an effective dose of a caspase inhibitor according to the invention (or a pharmaceutical composition comprising the same). This may be helpful for inhibiting a cellular caspase thereby inhibiting virus multiplication.

Also of particular interest is a method for the treatment of excessive apoptosis affected by caspase activity in a cell or a tissue, comprising contacting the cell or the tissue with an effective amount of one or more caspase inhibitor according to the invention (or a pharmaceutical composition comprising the same).

Also of particular interest is a method for effecting or stimulating stem cell survival and proliferation by preventing some of the stem cells from entering a partial or complete apoptosis cycle. The method for culturing a large quantity of stem cells may involves an effective amount of one or more caspase inhibitor according to the invention (or a pharmaceutical composition comprising the same) and a medium for culturing stem cells.

Also of particular interest is using compounds of the present invention for effecting or stimulating stem cell survival and proliferation in vivo by preventing some of the stem cells from entering a partial or complete apoptosis cycle. This treatment modality involves administering to the patient an effective amount of one or more caspase inhibitor according to the invention (or a pharmaceutical composition comprising the same) for effecting or stimulating stem cell survival and proliferation in the patient.

Although focusing on caspases, the present is not so limited. For instance, it is conceivable that the compounds of the invention be also effective in inhibiting additional families of proteases, including but not limited to, serine peptidases, cysteine peptidases, aspartic peptidases, metallo-peptidases, and other peptidases of unknown catalytic type. For a more elaborate listing of proteases that may be inhibited by the compounds defined herein, see ZBIGNIEW GRZONKA. Cysteine protease. Industrial Enzymes, 181-195, Chapter 11, 2007 Springer.

In order to evaluate, assess, and/or confirm the efficacy of the method, compounds and/or compositions of the invention, serial measurements can be determined. Quantitative assessment of caspase functions and parameters of caspase dysfunction are well known in the art. Examples of assays for the determination of caspases activity are provided in the Exemplification section.

The compounds according to the invention can be further analyzed, tested or validated for their ability to cross the Blood Brain Barrier BBB is so desired. Many in-vitro, in-vivo and in-silico methods may be employed during drug development to mimic the BBB (Lohmann et al. (2002) Predicting blood-brain barrier permeability of drugs: evaluation of different in vitro assays. *J Drug Target* 10:263-276; Nicolazzo et al. (2006) Methods to assess drug permeability across the blood-brain barrier. *J Pharm Pharmacol* 58:281-293).

In certain embodiments, at least some of the prodrugs administered generates the corresponding pharmaceutical compound only after absorption by the gastrointestinal tract and/or only once it has reached the brain, i.e. after it has passed the blood brain barrier (BBB).

E) Pharmaceutical Compositions and Formulations

A related aspect of the invention concerns pharmaceutical compositions comprising one or more of the compounds of the invention described herein. As indicated hereinbefore, the compounds of the invention may be useful in the prevention and/or treatment of various diseases and conditions in subjects, including cysteine protease-mediated diseases and/or caspase-mediated diseases such as sepsis, myocardial infarction, cancer, tissue atrophy, ischemia, ischemic stroke, spinal cord injury (SCI), traumatic brain injury (TBI) and neurodegenerative diseases such as multiple sclerosis (MS), ALS, Alzheimer's disease, Parkinson's disease, and Huntington's disease).

As used herein, the term "therapeutically effective amount" means the amount of compound that, when administered to a subject for treating or preventing a particular disorder, disease or condition, is sufficient to effect such treatment or prevention of that disorder, disease or condition. Dosages and therapeutically effective amounts may vary for example, depending upon a variety of factors including the activity of the specific agent employed, the age, body weight, general health, gender, and diet of the subject, the time of administration, the route of administration, the rate of excretion, and any drug combination, if applicable, the effect which the practitioner desires the compound to have upon the subject and the properties of the compounds (e.g. bioavailability, stability, potency, toxicity, etc), and the particular disorder(s) the subject is suffering from. In addition, the therapeutically effective amount may depend on the subject's blood parameters (e.g. lipid profile, insulin levels, glycemia), the severity of the disease state, organ function, or underlying disease or complications. Such appropriate doses may be determined using any available assays including the assays described herein. When one or more of the compounds of the invention is to be administered to humans, a physician may for example, prescribe a relatively low dose at first, subsequently increasing the dose until an appropriate response is obtained.

As used herein, the term "pharmaceutical composition" refers to the presence of at least one compound of the invention according to any one of Formula I, II, IA-VA, IVA1-IVA5, IIIA1-IIIA5 as defined herein and at least one pharmaceutically acceptable vehicle. Examples of representative compounds of the invention include the compounds in Table 1, and pharmaceutically acceptable salts thereof.

"Pharmaceutically acceptable vehicle" refers to a diluent, adjuvant, excipient, or carrier with which a compound is administered. The term "pharmaceutically acceptable" refers to drugs, medicaments, inert ingredients etc., which are suitable for use in contact with the tissues of humans and lower animals without undue toxicity, incompatibility, instability, irritation, allergic response, and the like, commensurate with a reasonable benefit/risk ratio. It preferably refers to a compound or composition that is approved or approvable by a regulatory agency of the Federal or state government or listed in the U.S. Pharmacopoeia or other generally recognized pharmacopoeia for use in animals and more particularly in humans. The pharmaceutically acceptable vehicle can be a solvent or dispersion medium containing, for example, water, ethanol, polyol (for example, glycerol, propylene glycol, and liquid polyethylene glycol, and the like), suitable mixtures thereof, and vegetable oils. Additional examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate. Prevention of the action of microorganisms can be achieved by various antibacterial and antifungal agents, for example, parabens, chlorobutanol, phenol, ascorbic acid, thimerosal, and the like. In many cases, isotonic agents are included, for example, sugars, sodium chloride, or polyalcohols such as mannitol and sorbitol, in the composition. Prolonged absorption of injectable compositions can be brought about by including in the composition an agent which delays absorption, for example, aluminum monostearate or gelatin. Nanoparticles, liposomes, and antibodies conjugated to nanoparticles or combinations thereof, are also contemplated as pharmaceutically acceptable vehicles.

In some embodiments, the compositions of the invention comprise an effective amount of a compound of the Formula I, II, IA-VA, IVA1-IVA5, IIIA1-IIIA5 as described hereinbefore, preferably compound 2-Quinoline carbonyl-t-Leu-pro-Asp methyl vinyl sulfone (6); 4-amino-3-chlorobenzene carbonyl-t-Leu-Pro-Asp methyl vinyl sulfone (14), Z-Asp-t-Leu-Pro-Asp-methyl vinyl sulfone (26), Z-Asp-t-Leu-(Azetidine-2-carbonyl)-Asp-methyl vinyl sulfone (32), Z-Asp-Trp(N-Me)-Val-Asp-methyl vinyl sulfone (36), Z-Val-Glu-Ile-Asp-methyl vinyl sulfone (38), Z-Trp-Glu-Val-Asp-methyl vinyl sulfone (40), Z-Asp-Phg-Val-Asp Ethyl Vinyl Ester (105), 2-Quinoline carbonyl-t-Leu-Pro-Asp Ethyl Vinyl Ester (118) or a pharmaceutically acceptable salt, or prodrug, thereof.

In some embodiments the invention pertains to pharmaceutical compositions for preventing and/or treating diseases or other medical conditions in which at least one caspase is significantly involved that include one or more compounds of Formula I, II, IA-VA, IVA1-IVA5, IIIA1-IIIA5 as defined herein.

In some embodiments the invention pertains to pharmaceutical compositions for preventing and/or treating diseases or other medical conditions in which at least one caspase is significantly involved, the composition comprising one or more compounds of Formula I, II, IA-VA, IVA1-IVA5, IIIA1-IIIA5 as defined herein.

The compounds of the invention may be formulated prior to administration into pharmaceutical compositions using available techniques and procedures. For instance, the pharmaceutical compositions may be formulated into suitable administration (orally, parenterally, (intravascular (IV), intraarterial (IA), intramuscular (IM), depo-IM, subcutaneous (SC), and depo SC), sublingually, intranasally (inhalation), intrathecally, topically, or rectally, including slow release or controlled release formulations.

Preferably, the compound(s) of the invention can be orally administered. The formulations may conveniently be presented in unit dosage form and may be prepared by any methods well known in the art of pharmacy. Methods of preparing these formulations or compositions include the step of bringing into association a compound of the present invention with a pharmaceutically acceptable vehicle (e.g. an inert diluent or an assimilable edible carrier) and, optionally, one or more accessory ingredients. In general, the formulations are prepared by uniformly and intimately bringing into association a compound of the present invention with liquid carriers, or finely divided solid carriers, or both, and then, if necessary, shaping the product. The amount of the therapeutic agent in such therapeutically useful compositions is such that a suitable dosage will be obtained.

Formulations of the invention suitable for oral administration may be in the form of capsules (e.g. hard or soft shell gelatin capsule), cachets, pills, tablets, lozenges, powders, granules, pellets, dragees, e.g., coated (e.g., enteric coated) or uncoated, or as a solution or a suspension in an aqueous or non-aqueous liquid, or as an oil-in-water or water-in-oil liquid emulsion, or as an elixir or syrup, or as pastilles or as mouth washes and the like, each containing a predetermined amount of a compound of the present invention as an active ingredient. A compound of the present invention may also be administered as a bolus, electuary or paste, or incorporated directly into the subject's diet. Moreover, in certain embodiments these pellets can be formulated to (a) provide for instant or rapid drug release (i.e., have no coating on them); (b) be coated, e.g., to provide for sustained drug release over time; or (c) be coated with an enteric coating for better gastrointestinal tolerability. Coating may be achieved by conventional methods, typically with pH or time-dependent coatings, such that the compound(s) of the invention is released in the vicinity of the desired location, or at various times to extend the desired action. Such dosage forms typically include, but are not limited to, one or more of cellulose acetate phthalate, polyvinylacetate phthalate, hydroxypropyl methyl cellulose phthalate, ethyl cellulose, waxes, and shellac.

In solid dosage forms for oral administration a compound of the present invention may be mixed with one or more pharmaceutically acceptable carriers, such as sodium citrate or dicalcium phosphate, or any of the following: fillers or extenders, such as starches, lactose, sucrose, glucose, mannitol, or silicic acid; binders, such as, for example, carboxymethylcellulose, alginates, gelatin, polyvinyl pyrrolidone, sucrose or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol and glycerol monostearate; absorbents, such as kaolin and bentonite clay; lubricants, such as talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

Peroral compositions typically include liquid solutions, emulsions, suspensions, and the like. The pharmaceutically acceptable vehicles suitable for preparation of such compositions are well known in the art. Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, tragacanth, and sodium alginate; typical wetting agents include lecithin and polysorbate 80; and typical preservatives include methyl paraben and sodium benzoate. Peroral liquid compositions may also contain one or more components such as sweeteners, flavoring agents and colorants disclosed above.

Pharmaceutical compositions suitable for injectable use may include sterile aqueous solutions (where water soluble) or dispersions and sterile powders for the extemporaneous preparation of sterile injectable solutions or dispersions. In all cases, the composition must be sterile and must be fluid to the extent that easy syringability exists. It must be stable under the conditions of manufacture and storage and must be preserved against the contaminating action of microorganisms such as bacteria and fungi. Sterile injectable solutions can be prepared by incorporating the therapeutic agent in the required amount in an appropriate solvent with one or a combination of ingredients enumerated above, as required, followed by filtered sterilization. Generally, dispersions are prepared by incorporating the therapeutic agent into a sterile vehicle which contains a basic dispersion medium and the required other ingredients from those enumerated above. In the case of sterile powders for the preparation of sterile injectable solutions, the methods of preparation are vacuum drying and freeze-drying which yields a powder of the active ingredient (i.e., the therapeutic agent) plus any additional desired ingredient from a previously sterile-filtered solution thereof.

Pharmaceutical formulations are also provided which are suitable for administration as an aerosol, by inhalation. These formulations comprise a solution or suspension of the desired compound of any Formula herein or a plurality of solid particles of such compound(s). The desired formulation may be placed in a small chamber and nebulized. Nebulization may be accomplished by compressed air or by ultrasonic energy to form a plurality of liquid droplets or solid particles comprising the agents or salts. The liquid droplets or solid particles should have a particle size in the range of about 0.5 to about 5 microns. The solid particles can be obtained by processing the solid agent of any Formula described herein, or a salt thereof, in any appropriate manner known in the art, such as by micronization. The size of the solid particles or droplets will be, for example, from about 1 to about 2 microns. In this respect, commercial nebulizers are available to achieve this purpose. A pharmaceutical formulation suitable for administration as an aerosol may be in the form of a liquid, the formulation will comprise a water-soluble agent of any Formula described herein, or a salt thereof, in a carrier which comprises water. A surfactant may be present which lowers the surface tension of the formulation sufficiently to result in the formation of droplets within the desired size range when subjected to nebulization.

The compositions of this invention can also be administered topically to a subject, e.g., by the direct laying on or spreading of the composition on the epidermal or epithelial tissue of the subject, or transdermally via a "patch". Such compositions include, for example, lotions, creams, solutions, gels and solids. These topical compositions may comprise an effective amount, usually at least about 0.1%, or even from about 1% to about 5%, of a compound of the invention. Suitable carriers for topical administration typically remain in place on the skin as a continuous film, and resist being removed by perspiration or immersion in water. Generally, the carrier is organic in nature and capable of having dispersed or dissolved therein the therapeutic agent. The carrier may include pharmaceutically acceptable emollients, emulsifiers, thickening agents, solvents and the like.

Other compositions useful for attaining systemic delivery of the subject agents include sublingual, buccal and nasal dosage forms. Such compositions typically comprise one or more of soluble filler substances such as sucrose, sorbitol and mannitol; and binders such as acacia, microcrystalline cellulose, carboxymethyl cellulose and hydroxypropyl methyl cellulose. Glidants, lubricants, sweeteners, colorants, antioxidants and flavoring agents disclosed above may also be included.

The compound(s) of the invention may also be administered parenterally, intraperitoneally, intravenously, intraspinally, intrathecally or intracerebrally. For such compositions, the compound(s) of the invention can be prepared in glycerol, liquid polyethylene glycols, and mixtures thereof and in oils. Under ordinary conditions of storage and use, these preparations may contain a preservative to prevent the growth of microorganisms.

In addition to the traditional drug delivery systems (oral, subcutaneous, intravenous (IV), intraperitoneal (IP)) intranasal drug delivery may constitutes a suitable alternative to deliver the compound(s) of the invention directly to CNS (critical reviews in therapeutic Drug Carrier Systems 23(4): 319-347, 2006).

Intranasal drug delivery allows certain drugs to be delivered in low doses, avoiding hepatic first pass metabolism with minimal side effects, improving cost effectiveness and better patient compliance. Intranasal delivery allows the drug that do not cross the BBB to be delivered to the central nervous system within minutes. It also directly delivers drugs that do cross the BBB to the brain. This is due to the unique connection that the olfactory and trigeminal nerves provide between the brain and external environment (Recent Patents on drug Delivery & Formulation 2008, 2, 25-40).

Formulation of the invention suitable for intranasal administration may involve gelling agent or gel-forming carriers such as hydroxypropylcellulose, methylcellulose, poly(vinyl pyrrolidone); poly(ethylene oxide); crosslinked poly(acrylic acid), and chitosan. Such agents can increase the residence time and uptake of the compound(s) of the invention in the nasal cavity, Cosolvents such as glycols ethyl alcohol, diethylene glycol monoethyl ether, medium chain glycerides, and labrasol are Examples of agents that can be used to enhance solubility. The use of surfactants or cyclodextrins such as hydroxypropyl-B-cyclodextrine in combination with lipophilic absorption enhancers can be considered as well. Other Intranasal formulation involves cationic liposomes, microspheres, nanoparticles. Regardless to the method of the formulation used, buffering agents and protease inhibitors may be added as well.

The method of treatment of the present invention may also include co-administration of the at least one compound according to the invention, or a pharmaceutically acceptable salt thereof together with the administration of another therapeutically effective agent. Therefore, an additional aspect of the invention relates to methods of concomitant therapeutic treatment of a subject, comprising administering to a subject in need thereof an effective amount of a first agent and a second agent, wherein the first agent is as defined in I, II, IA-VA, IVA1-IVA5, IIIA1-IIIA5 and the second agent is for the prevention or treatment of any one of disorder or disease indicated hereinbefore. As used herein, the term "concomitant" or "concomitantly" as in the phrases "concomitant therapeutic treatment" or "concomitantly with" includes administering a first agent in the present of a second agent. A concomitant therapeutic treatment method includes methods in which the first, second, third or additional agents are co-administered. A concomitant therapeutic treatment method also includes methods in which the first or additional agents are administered in the presence of a second or additional agents, wherein the second or additional agents, for example, may have been previously administered. A concomitant therapeutic treatment method may be executed step-wise by different actors. For example, one actor may administer to a subject a first agent and as a second actor may administer to the subject a second agent and the administering steps may be executed at the same time, or nearly the same time, or at distant times, so long as the first agent (and/or additional agents) are after administration in the presence of the second agent (and/or additional agents). The actor and the subject may be the same entity (e.g. a human).

Accordingly, the invention also relates to a method for preventing, reducing or eliminating a symptom or complication of any one of the above mentioned disease or condition. The method comprises administering, to a subject in need thereof, a first pharmaceutical composition comprising at least one compound of the invention and a second pharmaceutical composition comprising one or more additional active ingredients, wherein all active ingredients are administered in an amount sufficient to inhibit, reduce, or eliminate one or more symptoms or complications of the disease or condition to be treated. In one aspect, the administration of the first and second pharmaceutical composition is temporally spaced apart by at least about two minutes. Preferably the first agent is a compound of Formula I, II, IA-VA, IVA1-IVA5, IIIA1-IIIA5 as defined herein, or a pharmaceutically acceptable salt thereof.

F) Screening Assays

The compounds of the present invention may also be used in screening methods. For instance, these compounds may be used in methods for tracking activity of caspases in vitro and/or in vivo. The compounds of the present invention may also be helpful for identifying other compounds that bind to a caspase active side. In some embodiments, the compounds of the invention are labeled or tagged (e.g. fluorescently or radioactively labeled, affinity tag). Fluorescent or radiolabeled compounds may also be useful in diagnostic assays.

There are a number of ways in which to determine the binding of a compound of the present invention to the caspase. In one embodiment the caspase is bound to a support, and a labeled compound of the invention is added to the assay. Alternatively, the compound of the invention may be bound to the support and the caspase is added.

The compounds of the invention may also be used as competitors to screen for additional drug candidates or test compounds. As used herein, the terms "drug candidate" or "test compounds" are used interchangeably and describe any molecule, for example, protein, oligopeptide, small organic molecule, polysaccharide, polynucleotide, and the like, to be tested for bioactivity.

Typically, the signals that are detected in the assay (e.g. in vitro, in vivo and/or diagnostic) may include fluorescence, resonance energy transfer, time resolved fluorescence, radioactivity, fluorescence polarization, plasma resonance, or chemiluminescence and the like, depending on the nature of the label. Detectable labels useful in performing screening assays in this invention include a fluorescent label such as Fluorescein, Oregon green, dansyl, rhodamine, tetramethyl rhodamine, texas red, $Eu^{3+}$; a chemiluminescent label such as luciferase; colorimetric labels; enzymatic markers; or radioisotopes such as tritium, $I^{125}$ and the like. Affinity tags, which may be useful in performing the screening assays of the present invention include be biotin, polyhistidine and the like.

F) Kits

The compound(s) of the invention may be packaged as part of a kit, optionally including a container (e.g. packaging, a box, a vial, etc). The kit may be commercially used according to the methods described herein and may include instructions for use in a method of the invention. Additional kit components may include acids, bases, buffering agents, inorganic salts, solvents, antioxidants, preservatives, or metal chelators. The additional kit components are present as pure compositions, or as aqueous or organic solutions that incorporate one or more additional kit components. Any or all of the kit components optionally further comprise buffers.

The compound(s) of the invention may or may not be administered to a patient at the same time or by the same route of administration. Therefore, the methods of the invention encompass kits which, when used by the medical practitioner, can simplify the administration of appropriate amounts of two or more active ingredients to a patient.

A typical kit of the invention comprises a unit dosage form of a at least one compound according to the invention, e.g., a compound of Formula I, II, IA-VA, IVA1-IVA5, IIIA1-IIIA5 as defined herein or a pharmaceutically acceptable salt thereof, and a unit dosage form of at least one additional active ingredient. Examples of additional active ingredients that may be used in conjunction with the compounds according to the invention, include, but are not limited to any of the compounds that could be used in combination with the compound(s) of the invention as indicated herein before.

Kits of the invention can further comprise devices that are used to administer the active ingredients. Examples of such devices include, but are not limited to, syringes, drip bags, patches, inhalers, enemas, and dispensers for the administration of suppository formulations.

Kits of the invention can further comprise pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles are provided hereinbefore.

EXAMPLES

The Examples set forth herein below provide exemplary methods for the preparation of certain representative compounds encompassed by general Formula I, II, IA-VA, IVA1-IVA5, IIIA1-IIIA5. Some Examples provide exemplary uses of certain representative compounds of the invention. Also provided are exemplary methods for assaying the compounds of the invention for in vitro and in vivo efficacy.

Example 1: Synthesis of Compound 2
(Cbz-Val-Asp αchlorovinyl Methyl Vinyl Sulfone)

a) Synthesis of Cbz-Val-Asp(O-tBu) αchlorovinyl Methyl Vinyl Sulfone

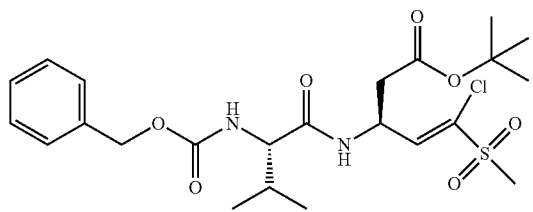 [SMILES: CC(C)[C@H](NC(=O)OCc1ccccc1)C(=O)N[C@H](/C=C(\Cl)S(C)(=O)=O)CC(=O)OC(C)(C)C]

The Z-Val-OH (20 mg, 0.0795 mmol) is dissolved in a mix of THF and DMF (0.45 ml/0.10 ml). The mixture was allowed to reach −18° C. (ice/MeOH bath) before dropwise addition of N-methyl morpholine (9.5 µl) followed 3 min later with dropwise addition of isobutyl chloroformate (11 µl). The mixture was stirred for 10 minutes (the ice bath was changed after 8 minutes when the temperature of the bath dropped −13° C.). Next, Asp (β-tert-butyl) αchlorovinyl methyl vinyl sulfone tosyl salt (38 mg, 1 eq) was added in one shot, followed by dropwise addition of N-methyl morpholine (9.5 µl). The mixture was stirred for 35 minutes, then diluted with 5 ml of dichloromethane and quenched with dropwise addition of water (1 ml) at −12° C. The mixture was stirred 2 minutes at −12° C. and 5 minutes at RT. The mixture was transferred in a separatory funnel and it was diluted with dichloromethane (8 ml). The aqueous layer was washed with dichloromethane (2*8 ml). The combined organic layer was dried over magnesium sulphate. The solvent was evaporated to dryness, then added to the sample of Biotage column (10 g). The purification is carried out first with ethyl acetate/hexane (40%, 12 CV) to afford 28 mg of Z-Val-Asp(O-tBu) αchlorovinyl methyl vinyl sulfone, obtained as E-isomer. NMR $^1$H (CD$_3$OD, 500 MHz) δ: 7.40-7.30 (m, 5H); 7.05 (d, 1H, J=8.60 Hz); 5.11-5.06 (m, 3H); 3.89 (d, 1H, J=7.15 Hz); 3.09 (s, 3H); 2.74-2.65 (m, 2H); 2.03 (m, 1H); 1.45 (s, 9H); 0.95 (dd, 6H, J=2.40, 6.80 Hz).

b) Synthesis of Cbz-Val-Asp αchlorovinyl Methyl Vinyl Sulfone

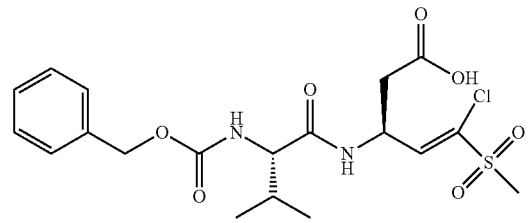 [SMILES: CC(C)[C@H](NC(=O)OCc1ccccc1)C(=O)N[C@H](/C=C(\Cl)S(C)(=O)=O)CC(=O)O]

Z-Val-Asp(O-tBu) αchlorovinyl methyl vinyl sulfone (27 mg) was dissolved in dichloromethane (0.7 ml) for 4 min, followed by quick addition of trifluoroacetic acid (1 ml). The mixture was stirred at room temperature overnight (15 h). It was then quenched with diethyl ether (6 ml) and the solvent was removed under vacuum. The obtained residue was diluted again with ether (6 ml) and the process was repeated twice. The obtained solid was washed with ether (2*1 ml). The filtrate was removed and the precipitate was dried to give 20 mg of the desired compound. NMR $^1$H (CD$_3$OD, 500 MHz) δ: 7.40-7.29 (m, 5H); 7.10 (d, 1H, J=8.50 Hz); 5.17-5.06 (m, 3H); 3.90 (d, 1H, J=6.55 Hz); 3.09 (s, 3H); 2.87-2.68 (m, 2H); 2.10-2.02 (m, 1H); 0.95 (m, 6H).

Example 2: Synthesis of Compound 4 (Asp αchlorovinyl Methyl Vinyl Sulfone, Tosyl Salt)

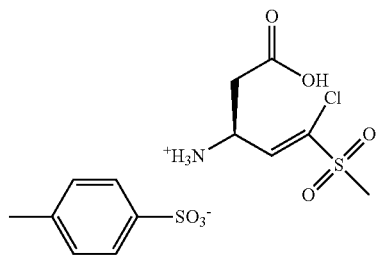

(β-tert-butyl)αchlorovinyl methylsulfone tosyl salt (15 mg) was dissolved in dichloromethane (0.5 ml) for 4 min, followed by quick addition of trifluoroacetic acid (0.7 ml). The mixture was stirred at room temperature overnight (15 h). It was then quenched with diethyl ether (5 ml) and the solvent was removed under vacuum. The obtained residue was diluted again with ether (5 ml) and the process was repeated twice. The obtained solid was washed with ether (2*0.6 ml). The filtrate was removed and the precipitate was dried to give the desired compound. NMR $^1$H (CD$_3$OD, 500 MHz) δ: 7.74-7.72 (m, 2H); 7.25 (d, 2H, J=7.90 Hz); 7.17 (d, 1H, J=9.00 Hz); 4.63-4.57 (m, 1H); 3.18 (s, 3H); 2.93 (d, 2H, J=6.15 Hz); 2.39 (s, 3H).

Example 3: Synthesis of Compound 6 (2-Quinoline carbonyl-t-Leu-P,Io/ro-Asp Methyl Vinyl Sulfone)

a) 2-Quinoline carbonyl-t-Leu-Pro-OH

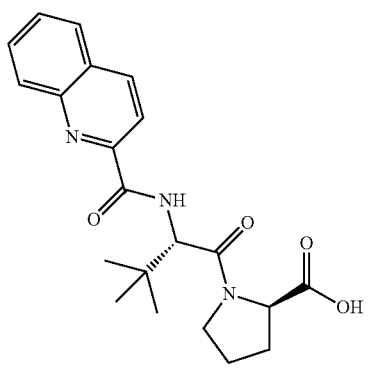 [SMILES: CC(C)(C)[C@H](NC(=O)c1ccc2ccccc2n1)C(=O)N1CCC[C@@H]1C(=O)O]

a1) Synthesis of Pro-OAllyl TFA Salt

Boc-Pro-OH (1.5 g, 6.97 mmol) in dichloromethane and DMF (35 ml/3 ml) were added sequentially Allyl alcohol (0.5 ml, 1.05 eq), followed with DMAP (0.085 g, 0.1 eq); 4-N-methyl morpholine ((0.82 ml, 1.06 eq), and EDC (1.4 g, 1.05 eq). The mixture was stirred for 2 h at RT, and then it was diluted with dichloromethane (40 ml) and washed with water (20 ml). The aqueous layer was re-extracted with dichloromethane (2*20 ml) dried over MgSO$_4$, filtered off and concentrated to dryness. The obtained crude was purified on Biotage column (50 g), using a gradient of Ethyl acetate/Hexane (5-40%) to get 1.53 g of the desired compound.

1.53 g (6.01 mmol) of the previous crude material (Boc-Pro-OAllyl) was solvated in a solution of dichloromethane (10 ml) followed with slow addition of TFA (10 ml). The mixture was stirred at room temperature for 1 hour. It was then evaporated to dryness, and co-evaporated with dichloromethane (3*20 ml), then it was kept under higher vacuum for 2 hours) to get 1.6 g of Pro-OAllyl TFA salt.

a2) Synthesis of t-Leu-Pro-OAllyl TFA Salt

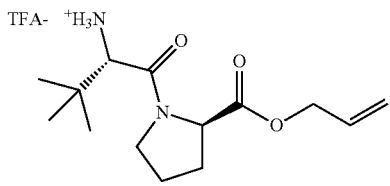 [SMILES: C=CCOC(=O)[C@H]1CCCN1C(=O)[C@@H]([NH3+])C(C)(C)C]

A solution of Pro-OAllyl TFA salt (0.858 g, 1 eq) in DMF (8 ml) was added N,N-diisopropyl ethyl amine (0.56 ml, 1 eq) and the mixture was stirred for 5 min, then added to a solution of Boc-t-Leu-OH (0.75 g, 3.21 mmol) in 6 ml of DMF. The mixture was chilled at 0° C. HOBT anhydrous (0.434 g, 1 eq) was added followed with EDC (0.675 g; 1.1 eq) in DMF (2 ml, as a suspension), the vial of EDC was washed with DMF (2*2 ml) and was added to the solution. The mixture was stirred for 22 h (0° C. to RT). The DMF was evaporated under vacuum. It was then diluted with EtOAc (60 ml), the organic layer was washed with H$_2$SO$_4$ 2 N (3*10 ml), then K$_2$CO$_3$ (7.5% w/w) (3*10 ml), then Brine (1*10 ml). The organic layer was dried with MgSO$_4$, filtered off and the solvent was evaporated to dryness. The crude was purified on Biotage column (50 g) using a gradient of Ethyl acetate/Hexane (7-60%) to get 0.43 g of the desired of Boc-t-Leu-Pro-OAllyl. This compound was solvated in a solution of dichloromethane (2.5 ml) followed with slow addition of TFA (2.5 ml). The mixture was stirred at room temperature for 1 hour. It was then evaporated to dryness, and co-evaporated with dichloromethane (3*8 ml), then it was kept under higher vacuum for 2 hours to get 0.446 g of t-Leu-Pro-OAllyl TFA salt a3) Synthesis of 2-Quinoline carbonyl-t-Leu-Pro-OAllyl

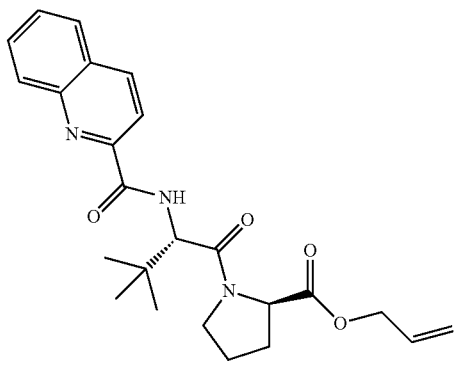 [SMILES: C=CCOC(=O)[C@H]1CCCN1C(=O)[C@@H](NC(=O)c1ccc2ccccc2n1)C(C)(C)C]

A solution of t-Leu-Pro-OAllyl TFA salt (0.228 g, 1 eq) in DMF (0.84 ml) was added N,N-diisopropyl ethyl amine (0.1 ml, 1 eq) and the mixture was stirred for 5 min, then added to a solution of Quinaldic acid (0.104 g, 0.6 mmol) in 0.55 ml of DMF. The mixture was chilled at 0° C. HOBT anhydrous (0.082 g, 1 eq) was added followed with EDC (0.125 g; 1.1 eq) in DMF (0.42 ml, as a suspension), the vial of EDC was washed with DMF (2*0.3 ml) and was added to the solution. The mixture was stirred for 22 h (0° C. to RT). The DMF was evaporated under vacuum. It was then diluted with EtOAc (10 ml), the organic layer was washed with Citric acid 0.5 M (3*3 ml), then K$_2$CO$_3$ (7.5% w/w) (3*3 ml), then Brine (1*3 ml). The organic layer was dried with MgSO$_4$, filtered off and the solvent was evaporated to dryness to get the desired compound (0.164 g).

a4) Synthesis of 2-Quinolinecarbonyl-t-Leu-Pro-OH

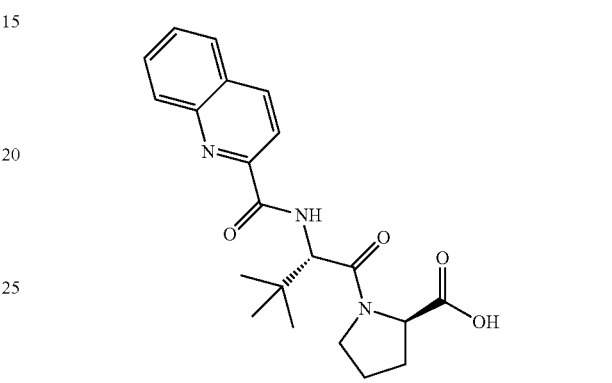

2-Quinoline carbonyl-t-Leu-Pro-OAllyl (0.164 g; 0.387 mmol) was co-evaporated with THF to dryness (2*2 ml), then dissolved under argon in dry THF (4.6 ml, inhibitor free). The solvent was degassed three times under argon (3 min+2+2) before dropwise addition of morpholine (0.169 ml, 5 eq) followed with addition of Tetrakis in one shot (45 mg, 0.1 eq). The mixture was purged under argon for 3 min. the reaction was carried out in the absence of light and at room temperature for 30 minutes. It was then diluted with ether (5 ml) followed with citric acid 0.5M (5 ml). The mixture was stirred for 3 minutes, then extracted. The aqueous layer was washed with ether (3*6 ml) then combined. The organic layer was washed with Brine (2 ml), dried with MgSO$_4$. The solvent was evaporated to dryness. The crude was purified on normal silica, Biotage column (10 g) using a gradient of MeOH/CH2Cl2 (10-100%) to get 0.092 g of 2-Quinoline carbonyl-t-Leu-Pro-OH. NMR $^1$H (CD$_3$OD, 500 MHz) δ: 8.51 (d, 1H, J=8.15 Hz); 8.23-8.17 (m, 2H); 8.04-8.01 (m, 1H); 7.88-7.85 (m, 1H); 7.74-7.72 (m, 1H); 4.94 (s, 1H); 4.51-4.47 (m, 1H); 4.04-3.99 (m, 1H); 3.89-3.84 (m, 1H); 2.35-2.00 (m, 4H); 1.20 (s, 9H).

a5) Synthesis of Compound 5 (2-Quinoline carbonyl-t-Leu-pro-Asp(O-tBu)methyl Vinyl Sulfone)

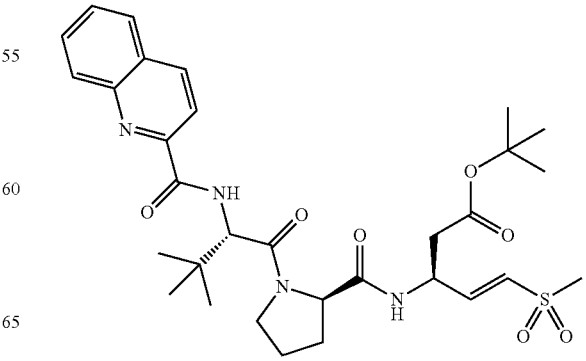

The 2-Quinoline carbonyl-t-Leu-Pro-OH (25 mg, 0.065 mmol) is dissolved in a mix of THF and DMF (0.45 ml/0.1 ml). The mixture was allowed to reach −18° C. (ice/MeOH bath) before dropwise addition of N-methyl morpholine (8 µl) followed 3 min later with dropwise addition of isobutyl chloroformate (9.5 µl). The mixture was stirred for 10 minutes (the ice bath was changed after 8 minutes when the temperature of the bath dropped −13° C.). Next, Asp (β-tert-butyl) methyl vinyl sulfone tosyl salt (29.5 mg, 1 eq) was added in one shot, followed by dropwise addition of N-methyl morpholine (8 µl). The mixture was stirred for 35 minutes, then diluted with 6 ml of dichloromethane and quenched with dropwise addition of saturated solution of sodium bicarbonate (1 ml) at −12° C. The mixture was stirred 2 minutes at −12° C. and 5 minutes at RT. The mixture was transferred in a separatory funnel and it was diluted with dichloromethane (5 ml). The aqueous layer was washed with dichloromethane (2*6 ml). The combined organic layer was dried over magnesium sulphate. The solvent was evaporated to dryness. The obtained residue was added to the samplet of Biotage column (10 g). The purification is carried out first with ethyl acetate/hexane (40%, 12 CV), then dichloromethane/methanol (0 to 15%, 10 CV) to afford 36 mg of 2-Quinoline carbonyl-t-Leu-pro-Asp(O-tBu) methyl vinyl sulfone obtained as E-isomer.

a6) Synthesis of 2-Quinoline carbonyl-t-Leu-pro-Asp Methyl Vinyl Sulfone

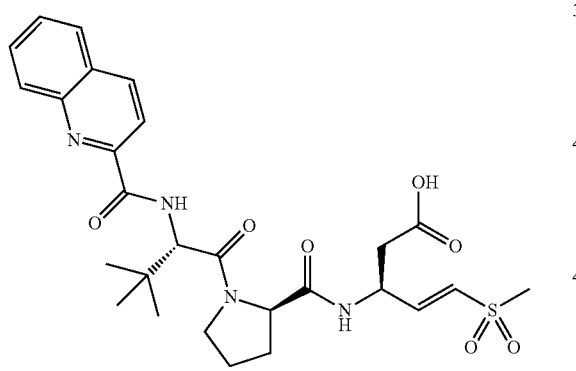

2-Quinoline carbonyl-t-Leu-pro-Asp(O-tBu) methyl vinyl sulfone (34 mg) was dissolved in dichloromethane (0.6 ml) for 4 min, followed by quick addition of trifluoroacetic acid (0.8 ml). The mixture was stirred at room temperature overnight (15 h). It was then quenched with diethyl ether (6 ml) and the solvent was removed under vacuum. The obtained residue was diluted again with ether (6 ml) and the process was repeated twice. The obtained solid was washed with ether (2*1 ml). The filtrate was removed and the precipitate was dried to give 32 mg of the desired compound. NMR $^1$H (CD$_3$OD, 500 MHz) δ: 8.52 (d, 1H, J=8.20 Hz); 8.22 (d, 1H, J=8.50 Hz); 8.18 (d, 1H, J=8.50 Hz); 8.03 (d, 1H, J=7.68 Hz); 7.89-7.85 (m, 1H); 7.74-7.71 (m, 1H); 6.94-6.90 (m, 1H); 6.77-6.71 (m, 1H); 4.92 (s, 1H); 4.45-4.42 (m, 1H); 4.06-4.02 (m, 1H); 3.86-3.82 (m, 1H); 3.01 (s, 3H); 2.92-2.70 (m, 2H); 2.35-1.90 (m, 4H); 1.14 (s, 9H).

Example 4: Synthesis of Compound 14 ((4-amino-3-chlorobenzene carbonyl)-t-Leu-Pro-methyl Vinyl Sulfone)

a) Synthesis of 4-((tert-butoxycarbonyl)amino)-3-chlorobenzene carbonyl-t-Leu-Pro-OH

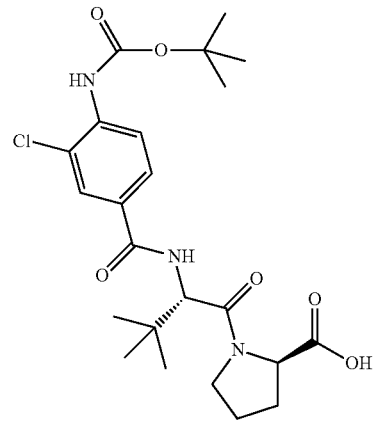 [SMILES: CC(C)(C)OC(=O)Nc1ccc(C(=O)N[C@H](C(=O)N2CCC[C@@H]2C(=O)O)C(C)(C)C)cc1Cl]

a1) Synthesis of (4-(tert-butoxycarbonyl)amino)-3-chlorobenzene carbonyl)-t-Leu-Pro-OAllyl

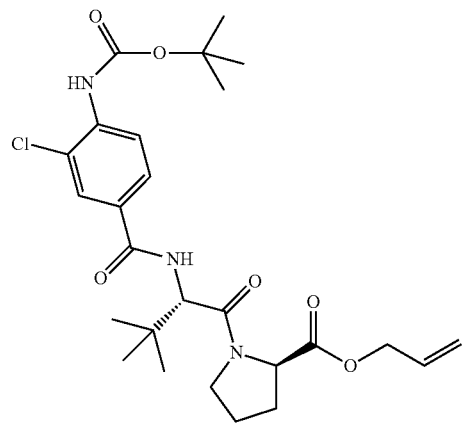 [SMILES: C=CCOC(=O)[C@H]1CCCN1C(=O)[C@@H](NC(=O)c1ccc(NC(=O)OC(C)(C)C)c(Cl)c1)C(C)(C)C]

a1a) Synthesis of 4-((tert-butoxycarbonyl)amino)-3-chlorobenzoic Acid

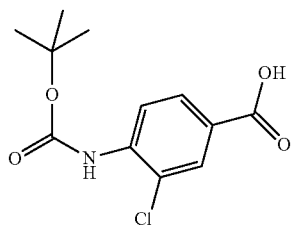 [SMILES: CC(C)(C)OC(=O)Nc1ccc(C(=O)O)cc1Cl]

a1b) Synthesis of methyl 4-amino-3-chlorobenzoate

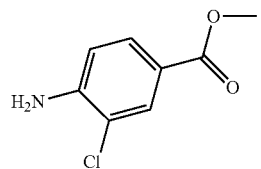

4-amino-3-chlorobenzoic acid in Methanol (10 ml) was added H$_2$SO$_4$ c (0.3 ml) and the mixture refluxed in the presence of a deen stark for the week end. It was allowed to reach the room temperature, then diluted with dichloromethane. A saturated solution of NaHCO3 (12 ml) was added (12 ml) and transferred to a separatory funnel. The organic layer was washed with brine, dried with MgSO4 and the solvent was evaporated to dryness to get the desired ester.

a1c) Synthesis of Methyl of 4-((tert-butoxycarbonyl)amino)-3-chlorobenzoate

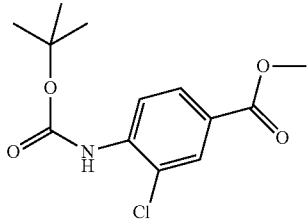 [SMILES: COC(=O)c1ccc(NC(=O)OC(C)(C)C)c(Cl)c1]

Step 1: methyl 4-amino-3-chlorobenzoate (1.24 g, 6.68 mmol) was dissolved in THF (20 ml) followed with Boc anhydride (20.4 ml, 1M in THF) and DMAP (0.1 eq). The mixture was refluxed for 1 h15, then it was allowed to reach the room temperature before to evaporate it to dryness.

Step 2: The obtained crude was dissolved in MeOH (40 ml), K2CO3 (2.3 g) was added and the mixture was refluxed for 2 h. The mixture was allowed to reach the room temperature, it was then diluted with ether (100 ml) and washed with Brine (3*30 ml), followed with citric acid 0.5 M (10 ml). The organic layer was dried with MgSO4, filtered off and purified on silica gel Biotage column to get the desired compound.

a1d) Synthesis of 4-((tert-butoxycarbonyl)amino)-3-chlorobenzoic Acid

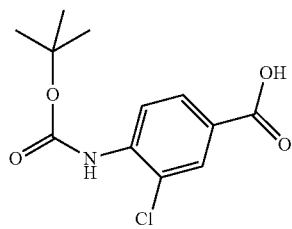 [SMILES: CC(C)(C)OC(=O)Nc1ccc(C(=O)O)cc1Cl]

Methyl of 4-((tert-butoxycarbonyl)amino)-3-chlorobenzoate (0.189 g, 0.66 mmol) was dissolved in THF (2.4 ml) and allowed to reach 0° C. LiOH 1M (0.72 ml, 1.1 eq) was added and the mixture was stirred overnight. The mixture was diluted with Ethyl acetate, then washed with citric acid 0.5 M (10 ml). The organic layer was dried with MgSO4, filtered off and the solvent was evaporated to dryness. The crude was purified on Biotage silica column, using gradient (Dichloromethane/Methanol, 0-15%) to get the desired 4-((tert-butoxycarbonyl)amino)-3-chlorobenzoic acid.

NMR $^1$H (CDCl$_3$, 500 MHz) δ: 8.36 (d, 1H, J=8.75 Hz); 8.11 (m, 1H); 8.01 (m, 1H); 1.58 (m, 9H).

a1e) Synthesis of (4-(tert-butoxycarbonyl)amino)-3-chlorobenzene carbonyl)-t-Leu-Pro-OAllyl

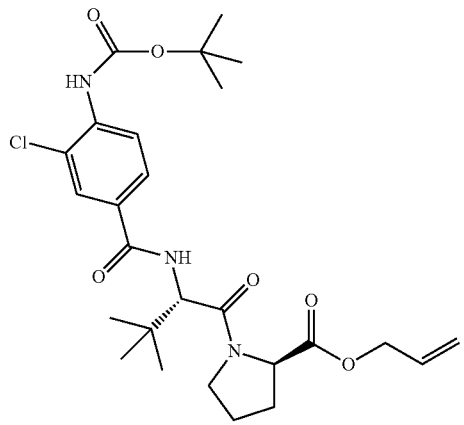 [SMILES: C=CCOC(=O)[C@H]1CCCN1C(=O)[C@@H](NC(=O)c1ccc(NC(=O)OC(C)(C)C)c(Cl)c1)C(C)(C)C]

A solution of t-Leu-Pro-OAllyl TFA salt (0.157 g, 1 eq) in DMF (0.6 ml) was added N,N-diisopropyl ethyl amine (0.069 ml, 1 eq) and the mixture was stirred for 5 min, then added to a solution of 4-((tert-butoxycarbonyl)amino)-3-chlorobenzoic acid (0.111 g, 0.41 mmol) in 0.4 ml of DMF. The mixture was chilled at 0° C. HOBT anhydrous (0.056 g, 1 eq) was added followed with EDC (0.087 g; 1.1 eq) in DMF (0.3 ml, as a suspension), The vial of EDC was washed with DMF (2*0.2 ml) and was added to the solution. The mixture was stirred for 22 h (0° C. to RT). The DMF was evaporated under vacuum. It was then diluted with EtOAc (15 ml), the organic layer was washed with Citric acid 0.5 M (3*3 ml), then K$_2$CO$_3$ (7.5% w/w) (3*3 ml), then Brine (1*3 ml). The organic layer was dried with MgSO$_4$, filtered off and the solvent was evaporated to dryness. The obtained crude was purified using a gradient of Ethyl acetate/Hexane (0-40%) to get the desired compound (0.1 g).

a2) Synthesis of (4-(tert-butoxycarbonyl)amino)-3-chlorobenzene carbonyl)-t-Leu-Pro-OH

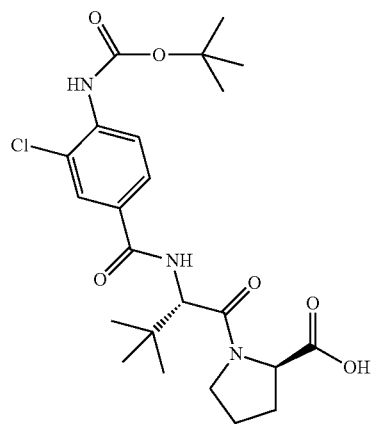 [SMILES: CC(C)(C)OC(=O)Nc1ccc(C(=O)N[C@H](C(=O)N2CCC[C@@H]2C(=O)O)C(C)(C)C)cc1Cl]

Same procedure to get 1,5-Naphthyridine-2-carbonyl-t-Leu-Pro-OH

NMR $^1$H (CD$_3$OD, 500 MHz) δ: 8.08 (d, 1H, J=9.12 Hz); 7.93 (d, 1H, J=2.00 Hz); 7.80-7.77 (m, 1H); 4.90 (s, 1H); 4.45-4.43 (m, 1H); 4.00-3.96 (m, 1H); 3.83-3.79 (m, 1H); 2.31-1.98 (m, 4H); 1.56 (s, 9H); 1.15 (s, 9H).

a3) Synthesis of (4-((tert-butoxycarbonyl)amino)-3-chlorobenzene carbonyl-t-Leu-Pro-methyl Vinyl Sulfone

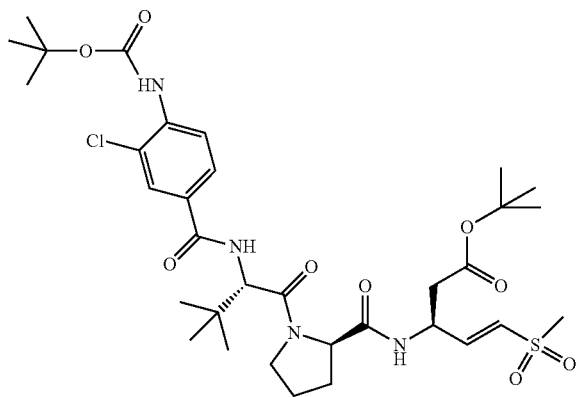 [SMILES: CC(C)(C)OC(=O)C[C@@H](/C=C/S(C)(=O)=O)NC(=O)[C@H]1CCCN1C(=O)[C@@H](NC(=O)c1ccc(NC(=O)OC(C)(C)C)c(Cl)c1)C(C)(C)C]

Same procedure to get (1,5-Naphthyridine-2-carbonyl)-t-Leu-Pro-Asp(O-tBu)methyl vinyl sulfone NMR ¹H (CD$_3$OD, 500 MHz) δ: 8.08 (d, 1H, J=8.50 Hz); 7.93 (d, 1H, J=2.05 Hz); 7.80-7.77 (m, 1H); 6.87 (dd, 1H, J=4.8, 15.20 Hz); 6.74 (dd, 1H, J=1.65, 15.20 Hz); 4.90 (s, 1H); 4.44-4.41 (m, 1H); 4.02-4.00 (m, 1H); 3.79-3.77 (m, 1H); 3.30 (m, 1H, hidden); 3.01 (s, 3H); 2.79 (dd, 1H, J=6.80, 16.00 Hz); 2.68 (dd, 1H, J=7.05, 16.00 Hz); 2.28-1.94 (m, 4H); 1.56 (s, 9H); 1.49 (s, 9H); 1.15 (s, 9H).

a4) Synthesis of (4-amino-3-chlorobenzene carbonyl)-t-Leu-Pro Methyl Vinyl Sulfone TFA Salt

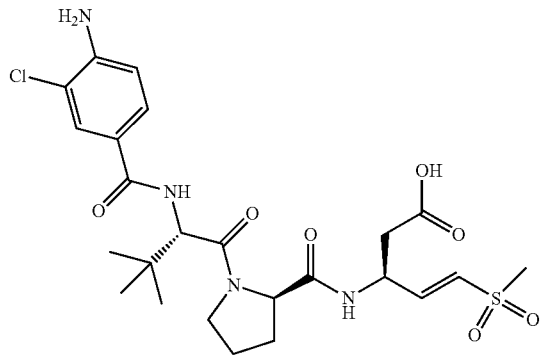 [SMILES: CC(C)(C)[C@H](NC(=O)c1ccc(N)c(Cl)c1)C(=O)N1CCC[C@@H]1C(=O)N[C@H](/C=C/S(C)(=O)=O)CC(=O)O]

Same procedure to get (1,5-Naphthyridine-2-carbonyl)-t-Leu-pro-Asp methyl vinyl sulfone Example 5: Synthesis of Compound 26 (Z-Asp-t-Leu-Pro-Asp-methyl Vinyl Sulfone)

a) Synthesis of z-Asp(O-tBu)-t-Leu-Pro-OH

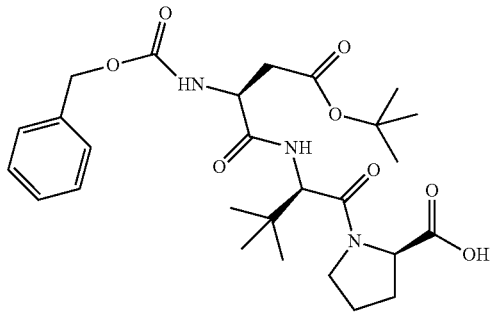 [SMILES: CC(C)(C)OC(=O)C[C@H](NC(=O)OCc1ccccc1)C(=O)N[C@@H](C(=O)N1CCC[C@@H]1C(=O)O)C(C)(C)C]

a1) Synthesis of z-Asp(O-tBu)-t-Leu-Pro-OAllyl

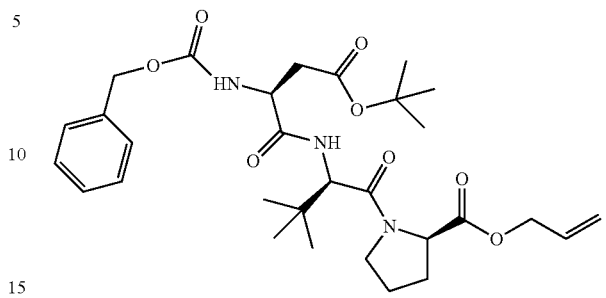

Same condition to get Synthesis of 2-Quinoline carbonyl-t-Leu-Pro-OAllyl (Cpd 6) from t-Leu-Pro-OAllyl TFA salt (0.45 g, 1 eq) and z-Asp(OtBu)-OH.

a2) Synthesis of z-Asp(O-tBu)-t-Leu-Pro-OH

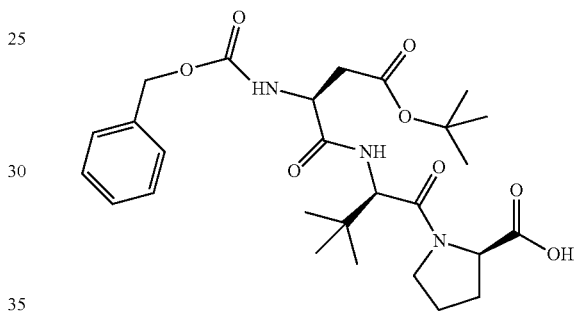

Same condition to get Synthesis of 2-Quinoline carbonyl-t-Leu-Pro-OH (Cpd 6) from z-Asp(O-tBu)-t-Leu-Pro-OAllyl. The crude was purified on C-18 column 50 g (pH: 3.5; gradient: 7 to 100% MeOH/Water; 4 ml methanol injection volume) to get 0.35 g of the desired product (second pic). NMR ¹H (CD$_3$OD, 500 MHz) δ: 7.39-7.29 (m, 5H); 5.13 (s, 2H); 4.63 (s, 1H); 4.54 (t, 1H, J=7.80 Hz); 4.43-4.41 (m, 1H); 3.89-3.85 (m, 1H); 3.76-3.71 (m, 1H); 2.79 (dd, 1H, J=6.20, 15.90 Hz); 2.58 (dd, 1H, J=8.10, 16.20 Hz); 2.28-1.99 (m, 4H); 1.43 (s, 9H); 1.03 (s, 9H).

b) Synthesis of Z-Asp(O-tBu)-t-Leu-Pro-Asp(O-tBu)-methyl Vinyl Sulfone

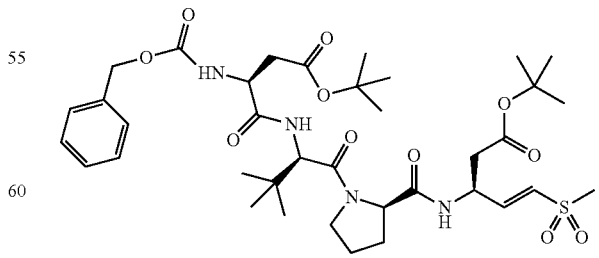

Same condition to get (2-Quinoline carbonyl-t-Leu-pro-Asp(O-tBu)methyl vinyl sulfone from z-Asp(O-tBu)-t-Leu-Pro-OH and Asp (β-tert-butyl) methyl vinyl sulfone tosyl salt c) Synthesis of Z-Asp-t-Leu-Pro-Asp-methyl Vinyl Sulfone

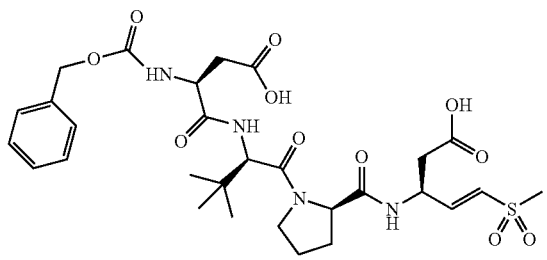 [SMILES: CC(C)(C)[C@@H](NC(=O)[C@H](CC(=O)O)NC(=O)OCc1ccccc1)C(=O)N1CCC[C@@H]1C(=O)N[C@H](/C=C/S(C)(=O)=O)CC(=O)O]

Same condition to get (2-Quinoline carbonyl-t-Leu-pro-Asp methyl vinyl sulfone (Cpd 6) from Z-Asp(O-tBu)-t-Leu-Pro-Asp(O-tBu)-methyl vinyl sulfone. NMR $^1$H (CD$_3$OD, 500 MHz) δ: 7.39-7.31 (m, 5H); 6.90 (dd, 1H, J=4.65, 15.20 Hz); 6.74 (dd, 1H, J=1.30, 15.35 Hz); 5.13 (m, 2H); 4.61 (s, 1H); 4.55 (t, 1H, J=6.70 Hz); 4.39 (m, 1H); 3.92 (m, 1H); 3.70 (m, 1H); 3.01 (s, 3H); 2.87-2.67 (m, 2H); 2.23-1.94 (m, 4H); 1.03 (s, 9H).

Example 6: Synthesis of Compound 6 (2-Quinoline carbonyl-t-Leu-(2-Azetidine carbonyl)-Asp Methyl Vinyl Sulfone)

a) 2-Quinoline carbonyl-t-Leu-Azetidine-2-carboxylic Acid

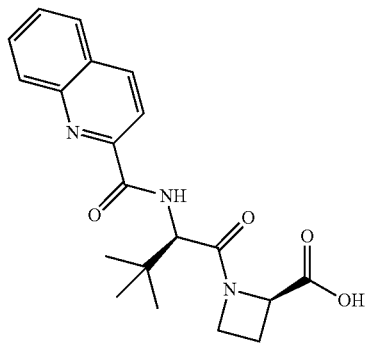 [SMILES: CC(C)(C)[C@@H](NC(=O)c1ccc2ccccc2n1)C(=O)N1CC[C@@H]1C(=O)O]

a1) Synthesis of Allyl azetidine-2-carboxylate TFA Salt

Same condition as to get Pro-OAllyl TFA salt, starting from Boc-Azetidine-2-carboxylic acid). Boc-Azetidine-2-carboxylic acid was obtained from Azetidine-2-carboxylic (7.02 mmol) in the presence of Boc anhydride (1.25 eq); NaOH (1.05 eq); EtOH/water (14/7 ml) from 0° C. to Rt over 18 h.

a2) Synthesis of t-Leu-Allyl azetidine-2-carboxylate TFA Salt

Same condition as to get t-Leu-Pro-OAllyl TFA salt

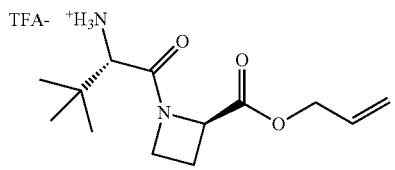 [SMILES: C=CCOC(=O)[C@H]1CCN1C(=O)[C@@H]([NH3+])C(C)(C)C]

a3) Synthesis of 2-Quinoline carbonyl-t-Leu-Allyl Azetidine-2-carboxylate

Same condition as to get 2-Quinoline carbonyl-t-Leu-Pro-OAllyl, starting from t-Leu-Allyl azetidine-2-carboxylate TFA salt and Quinaldic acid.

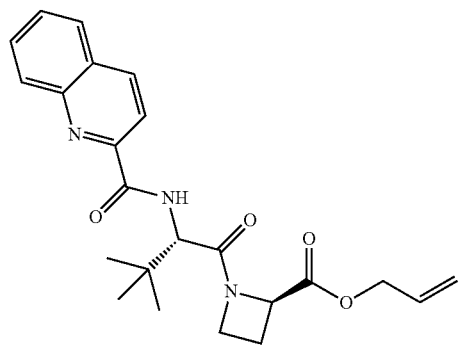 [SMILES: C=CCOC(=O)[C@H]1CCN1C(=O)[C@@H](NC(=O)c1ccc2ccccc2n1)C(C)(C)C]

a4) Synthesis of 2-Quinoline carbonyl-t-Leu-Azetidine-2-carboxylic Acid

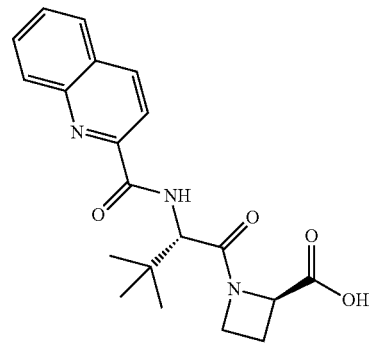 [SMILES: CC(C)(C)[C@H](NC(=O)c1ccc2ccccc2n1)C(=O)N1CC[C@@H]1C(=O)O]

Same condition as to get 2-Quinoline carbonyl-t-Leu-Pro-OH a5) Synthesis of 2-Quinoline carbonyl-t-Leu-(Azetidine-2-carbonyl)-Asp(O-tBu)methyl Vinyl Sulfone

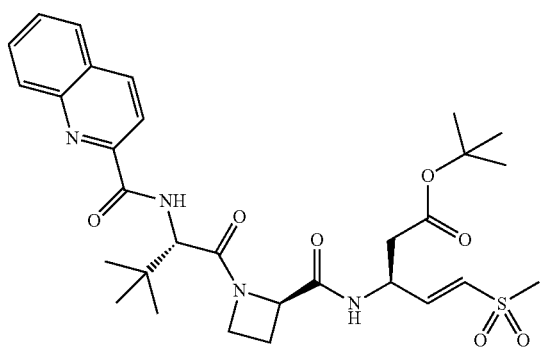 [SMILES: CC(C)(C)OC(=O)C[C@@H](/C=C/S(C)(=O)=O)NC(=O)[C@H]1CCN1C(=O)[C@@H](NC(=O)c1ccc2ccccc2n1)C(C)(C)C]

a6) Synthesis of 2-Quinoline carbonyl-t-Leu-(Azetidine-2-carbonyl)-Asp Methyl Vinyl Sulfone

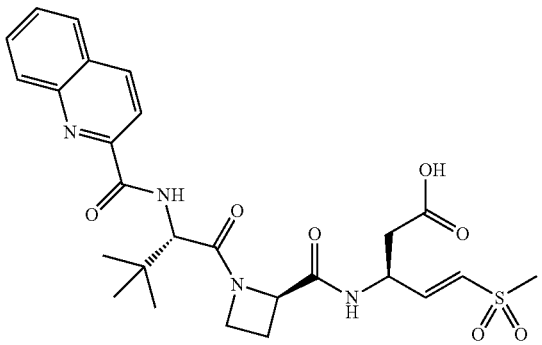 [SMILES: CC(C)(C)[C@H](NC(=O)c1ccc2ccccc2n1)C(=O)N1CC[C@@H]1C(=O)N[C@H](/C=C/S(C)(=O)=O)CC(=O)O]

Example 7: Synthesis of Compound 40 (Z-Trp-Glu-Val-Asp-methyl Vinyl Sulfone)

a) Synthesis of Z-Trp-Glu(O-tBu)-Val-OH

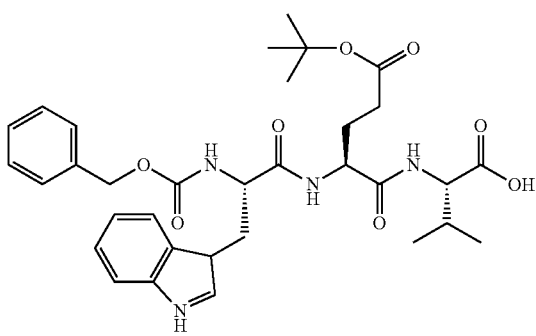 [SMILES: CC(C)[C@H](NC(=O)[C@H](CCC(=O)OC(C)(C)C)NC(=O)[C@H](CC1C=Nc2ccccc21)NC(=O)OCc1ccccc1)C(=O)O]

a1) Synthesis of Boc-Glu(O-tBu)-Val-OAllyl

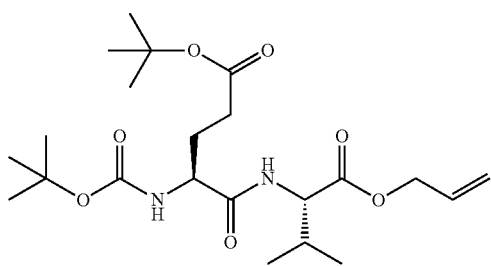 [SMILES: C=CCOC(=O)[C@@H](NC(=O)[C@H](CCC(=O)OC(C)(C)C)NC(=O)OC(C)(C)C)C(C)C]

To a solution of Tosyl valine (OAllyl) (1.5 g, 1 eq) in DMF (5.9 ml) was added N,N-diisopropyl ethyl amine (0.793 ml, 1 eq) and the mixture was stirred for 4 min, then added to a solution of Boc-Glu(O-tBu)-OH (1.381 g, 4.55 mmol) in 4 ml of DMF. The mixture was chilled at 0° C. HOBT anhydrous (0.615 g, 1 eq) was added followed with EDC (0.951 g; 1.09 eq) in DMF (3 ml, as a suspension), The vial of EDC was washed with DMF (3 ml) and added to the solution. The mixture was stirred for 22 h (0° C. to RT). It was then diluted with EtOAc (50 ml), the organic layer was washed with citric acid (2*5 ml), then K₂CO₃ (7.5% w/w) (3*10 ml), then Brine (1*10 ml). The organic layer was dried with MgSO4, filtered off and the solvent was evaporated to dryness to get the desired compound which was used for the next step as a crude material.

a2) Glu(O-tBu)-Val-OAllyl TFA Salt

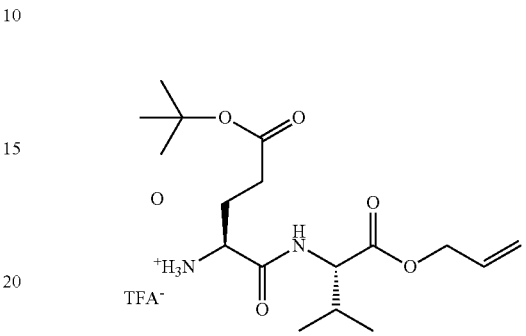

Boc-Glu(O-tBu)-Val-OAllyl 0.346 g (0.782 mmol) was solvated in a solution of dichloromethane (2.8 ml) and anisole (0.1 ml). It was allowed to reach 0° C., before a slow addition of TFA (2.8 ml). The mixture was stirred for 45 min 0° C. It was then evaporated quickly to dryness (Rotavap bath at 0° C.), then it was kept under higher vacuum for 2 hours) to get 0.35 g of Glu(O-tBu)-Val-OAllyl TFA salt. This compound is purified upon coupling with zTrp-OH.

a3) Z-Trp-Glu-(OtBu)-Val-OAllyl

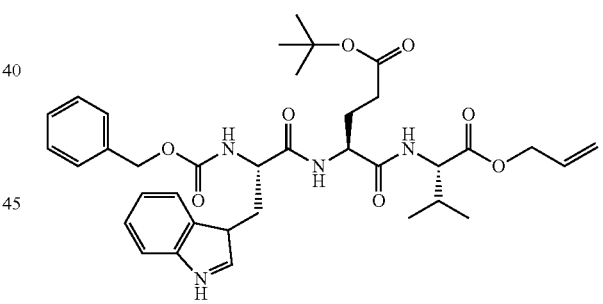

A solution of Glu(O-tBu)-Val-OAllyl TFA salt (0.356 g, 1 eq) in DMF (2 ml) was added N,N-diisopropyl ethyl amine (0.14 ml, 1 eq) and the mixture was stirred for 4 min, then added to a solution of Z-Trp-OH (0.264 g, 0.78 mmol) in 2.4 ml of DMF. The mixture was chilled at 0° C. HOBT anhydrous (0.105 g, 1 eq) was added followed with EDC (0.164 g; 1.1 eq) in DMF (1 ml, as a suspension), The vial of EDC was washed with DMF (2*1 ml) and was added to the solution. The mixture was stirred for 22 h (0° C. to RT). It was then diluted with EtOAc (50 ml), the organic layer was washed with citric acid 0.5 M (3*10 ml), then K₂CO₃ (7.5% w/w) (3*10 ml), then Brine (1*10 ml). The organic layer was dried with MgSO₄, filtered off and the solvent was evaporated to dryness to get 1.1 g of the desired and clean compound, which was purified on Biotage column silica gel, using a gradient Ethyl acetate/Hexane (30%) to get 0.28 g of Z-Trp-Glu-(OtBu)-Val-OAllyl.

a4) Z-Trp-Glu-(OtBu)-Val-OH

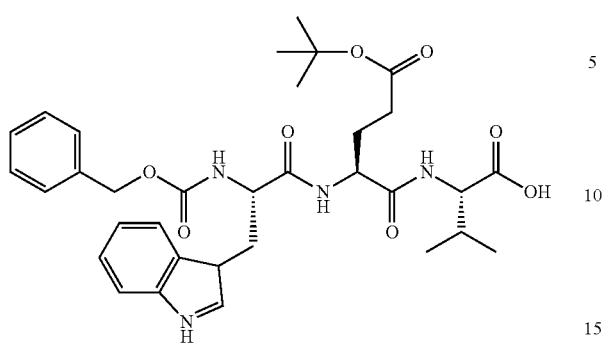

Same condition to get Synthesis of z-Asp(O-tBu)-t-Leu-Pro-OH (Cpd 26) from Z-Trp-Glu-(OtBu)-Val-OAllyl. NMR $^1$H (CD$_3$OD, 500 MHz) δ: 7.61 (d, 1H, J=7.90 Hz); 7.35-7.27 (m, 6H); 7.14-7.08 (m, 2H); 7.02-7.00 (m, 1H); 5.07-4.91 (m, 2H); 4.51-4.43 (m, 2H); 4.34-4.29 (m, 1H); 3.30-3.03 (m, 2H); 2.26-1.82 (m, 5H); 1.45 (s, 9H); 0.98 (d, 6H, J=5.80 Hz).

b) Synthesis of (Z-Trp-Glu-(OtBu)-Val-Asp(O-tBu) Methyl Vinyl Sulfone)

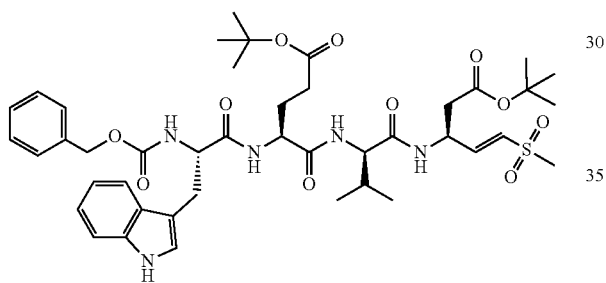

Same condition to get (2-Quinoline carbonyl-t-Leu-pro-Asp(O-tBu)methyl vinyl sulfone (Cpd 6) from Z-Trp-Glu-(OtBu)-Val-OH and Asp (β-tert-butyl) methyl vinyl sulfone tosyl salt.

c) Synthesis of (Z-Trp-Glu-Val-Asp Methyl Vinyl Sulfone)

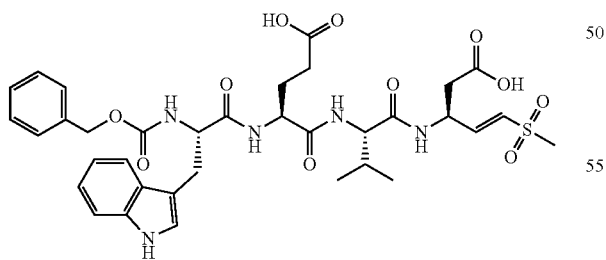

Same condition to get (2-Quinoline carbonyl-t-Leu-pro-Asp methyl vinyl sulfone (Cpd 6) from Z-Trp-Glu-(OtBu)-Val-Asp(O-tBu) methyl vinyl. NMR $^1$H (CD$_3$OD, 500 MHz) δ: 7.57 (d, 1H, J=7.65 Hz); 7.36-7.27 (m, 6H); 7.26-7.01 (m, 3H); 6.90 (dd, 1H, J=4.30, 15.15 Hz); 6.75 (d, 1H, J=15.05 Hz); 5.10-5.00 (m, 3H); 4.42 (t, 1H, J=6.75 Hz); 4.17-4.13 (m, 2H); 3.30-3.03 (m, 2H); 2.96 (s, 3H); 2.78-2.76 (m, 2H); 2.30-1.80 (m, 5H); 0.94 (m, 6H).

Example 8: Synthesis of Compound 36
(Z-Asp-Trp(N-Me)-Val-Asp-methyl Vinyl Sulfone)

a) Synthesis of Z-Asp(O-tBu)-Trp(N-Me)-Val-OH

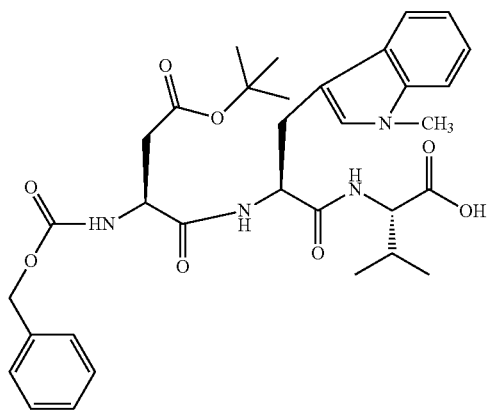 [SMILES: CC(C)[C@H](NC(=O)[C@H](Cc1cn(C)c2ccccc12)NC(=O)[C@H](CC(=O)OC(C)(C)C)NC(=O)OCc1ccccc1)C(=O)O]

A1) Trp(N-Me)-Val-OAllyl TFA Salt

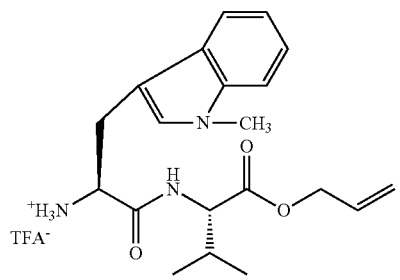 [SMILES: C=CCOC(=O)[C@@H](NC(=O)[C@@H]([NH3+])Cc1cn(C)c2ccccc12)C(C)C]

Step 1: Boc-Trp(N-Me)-Val-OAllyl was obtained in the same condition as to get Boc-Glu(O-tBu)-Val-OAllyl, starting from Boc-Trp(N-Me)-OH and Tosyl valine (OAllyl).

Step 2: Boc-Trp(N-Me)-Val-OAllyl 1.347 g (3.04 mmol) was solvated in a solution of dichloromethane (6.5 ml). It was allowed to reach 0° C., before a slow addition of TFA (6.5 ml). The mixture was stirred at room temperature for 60 min. It was then evaporated to dryness, then it was kept under higher vacuum for 45 min to get 1.33 g of Trp(N-Me)-Val-OAllyl TFA salt a2) zAsp-(O-tBu)-Trp(N-Me)-Val-OAllyl

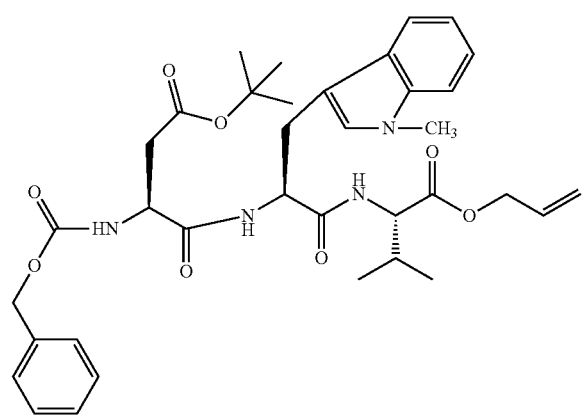 [SMILES: C=CCOC(=O)[C@@H](NC(=O)[C@H](Cc1cn(C)c2ccccc12)NC(=O)[C@H](CC(=O)OC(C)(C)C)NC(=O)OCc1ccccc1)C(C)C]

Same condition as to get Z-Trp-Glu-(OtBu)-Val-OAllyl, starting from zAsp(OtBu)-OH and Trp(N-Me)-Val-OAllyl TFA salt. It was used as a crude for the next step.

a4) zAsp-(O-tBu)-Trp(N-Me)-Val-OH

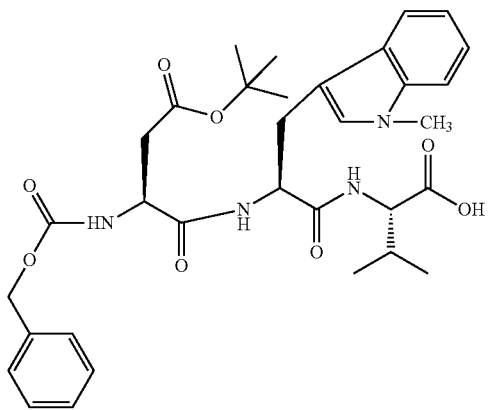 [SMILES: CC(C)[C@H](NC(=O)[C@H](Cc1cn(C)c2ccccc12)NC(=O)[C@H](CC(=O)OC(C)(C)C)NC(=O)OCc1ccccc1)C(=O)O]

zAsp-(O-tBu)-Trp(N-Me)-Val-OH was obtained in the same condition as to get Z-Trp-Glu-(OtBu)-Val-OH, starting from Z-Trp-Glu-(OtBu)-Val-OAllyl. NMR $^1$H (CD$_3$OD, 500 MHz) δ: 7.67-7.62 (m, 1H); 7.37-7.22 (m, 6H); 7.17-7.13 (m, 1H); 7.06-6.99 (m, 2H); 5.10-5.00 (m, 2H); 4.82-4.71 (m, 1H); 4.51-4.47 (m, 1H); 4.29-4.28 (m, 1H); 3.71 (s, 3H); 3.32-3.14 (m, 2H); 2.75-2.70 (m, 1H); 2.53-2.48 (m, 1H); 2.17-2.10 (m, 1H); 1.41 (s, 9H); 0.93 (m, 6H).

b) Synthesis of (zAsp-(O-tBu)-Trp(N-Me)-Val-Asp-(O-tBu)-methyl Vinyl Sulfone)

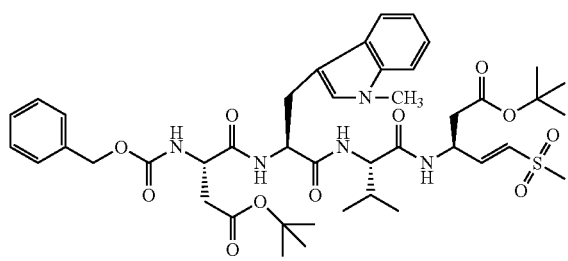 [SMILES: CC(C)[C@H](NC(=O)[C@H](Cc1cn(C)c2ccccc12)NC(=O)[C@H](CC(=O)OC(C)(C)C)NC(=O)OCc1ccccc1)C(=O)N[C@H](/C=C/S(C)(=O)=O)CC(=O)OC(C)(C)C]

The Z-Trp-Glu-(OtBu)-Val-OH (208 mg, 0.367 mmol) is dissolved in a mix of THF and DMF (2.5 ml/0.52 ml). The mixture was allowed to reach −18° C. (ice/MeOH bath) before dropwise addition of N-methyl morpholine (42 μl) followed 3 min later with dropwise addition of isobutyl chloroformate (50 μl). The mixture was stirred for 10 minutes (the ice bath was changed after 8 minutes when the temperature of the bath dropped to −13° C.). Next, Asp (β-tert-butyl) methyl vinyl sulfone tosyl salt (159 mg, 1 eq) was added in one shot, followed by dropwise addition of N-methyl morpholine (42 μl). The mixture was stirred for 35 minutes, then diluted with 8 ml of dichloromethane and quenched with dropwise addition of saturated solution of sodium bicarbonate (3 ml) at −12° C. The mixture was stirred 2 minutes at −12° C. and 5 minutes at RT. The mixture was transferred in a separatory funnel and it was diluted with dichloromethane (16 ml). The aqueous layer was washed with dichloromethane (2*16 ml). The combined organic layer was dried over magnesium sulphate. The solvent was evaporated to dryness, then added to the samplet of Biotage column (25 g). The purification is carried out first with ethyl acetate/hexane (40%, 12 CV), then dichloromethane/methanol (0 to 15%, 10 CV) to afford 260 mg of zAsp-(O-tBu)-Trp(N-Me)-Val-Asp-(O-tBu)-methyl vinyl sulfone, obtained as E-isomer.

c) Synthesis of (zAsp-Trp(N-Me)-Val-Asp-methyl Vinyl Sulfone)

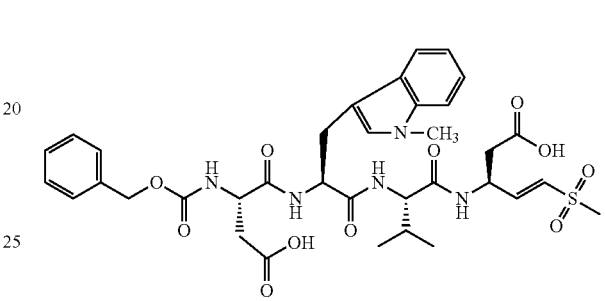

zAsp-(O-tBu)-Trp(N-Me)-Val-Asp-(-tBu)-methyl vinyl sulfone (260 mg) was dissolved in dichloromethane (4 ml) for 4 min, followed by quick addition of trifluoroacetic acid (5 ml). The mixture was stirred at room temperature overnight (15 h). It was then quenched with diethyl ether (12 ml) and the solvent was removed under vacuum. The obtained residue was diluted again with ether (12 ml) and the process was repeated twice. The obtained solid was washed with ether (3*1 ml). The filtrate was removed and the precipitate was dried to give 240 mg of the desired compound. It was then recrystallized in ethanol (2 ml) to get a pure E-isomer. NMR $^1$H (DMSO-d6, 500 MHz) δ: 8.23 (d, 1H, J=7.60 Hz, —NH); 8.04 (d, 1H, J=7.45 Hz, —NH); 7.83 (d, 1H, J=8.05 Hz); 7.62 (d, 1H, J=8.30 Hz); 7.57 (d, 1H, J=8.25 Hz); 7.36-7.86 (m, 6H); 7.13-6.99 (m, 3H); 6.76-6.65 (m, 2H); 5.06-4.98 (m, 2H); 4.84 (m, 1H); 4.57 (m, 1H); 4.38 (m, 1H); 4.13 (m, 1H); 3.69 (s, 3H); 3.20-2.90 (m, 2H); 2.97 (s, 3H); 2.70-2.40 (m, 4H); 2.00 (m, 1H); 0.83 (m, 6H).

Example 9: Synthesis of Compound 38 (Z-Val-Glu-Ile-Asp-methyl Vinyl Sulfone)

a) Synthesis of Z-Val-Glu(O-tBu)-Ile-OH

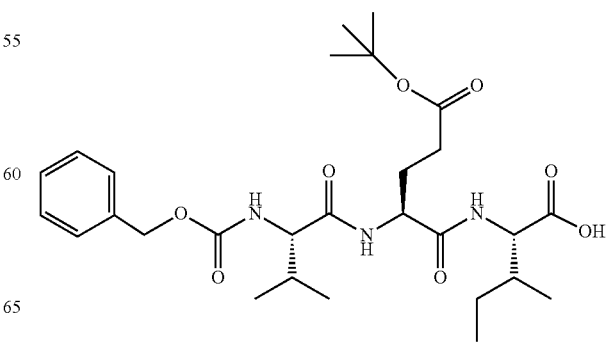

a1) Synthesis of Boc-Glu(O-tBu)-Ile-OAllyl

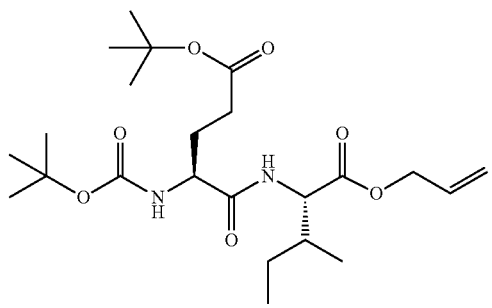 [SMILES: C=CCOC(=O)[C@@H](NC(=O)[C@H](CCC(=O)OC(C)(C)C)NC(=O)OC(C)(C)C)C(C)CC]

Boc-Glu(O-tBu)-Ile-OAllyl was obtained in the same condition than Boc-Glu(O-tBu)-Val-OAllyl.

a2) Glu(O-tBu)-Ile-OAlly TFA Salt

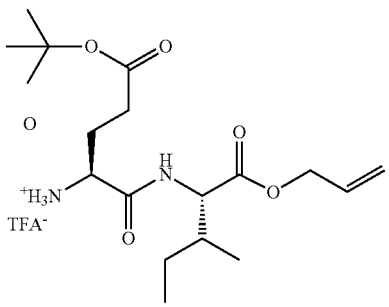 [SMILES: C=CCOC(=O)[C@@H](NC(=O)[C@@H]([NH3+])CCC(=O)OC(C)(C)C)C(C)CC ; O]

Glu(O-tBu)-Ile-OAllyl TFA salt was obtained as for Glu(O-tBu)-Val-OAllyl TFA salt (45 min reaction time).

a3) Z-Val-Glu-(OtBu)-Ile-OAllyl

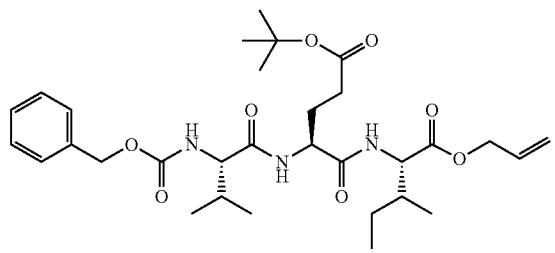 [SMILES: C=CCOC(=O)[C@@H](NC(=O)[C@H](CCC(=O)OC(C)(C)C)NC(=O)[C@@H](NC(=O)OCc1ccccc1)C(C)C)C(C)CC]

Z-Val-Glu-(OtBu)-Ile-OAllyl was obtained as for Z-Trp-Glu-(OtBu)-Val-OAllyl, staring from Z-val-OH and Glu(O-tBu)-Ile-OAllyl TFA. It was purified on Biotage column silica gel, using a gradient of Ethyl acetate/Hexane (7-60%).

a4) Z-Val-Glu-(OtBu)-Ile-OH

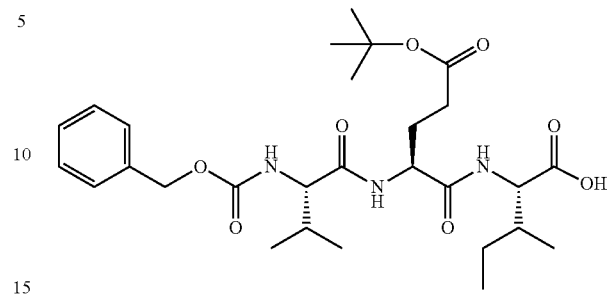

Z-Val-Glu-(OtBu)-Ile-OH was obtained in the same condition as for Z-Trp-Glu-(OtBu)-Val-OH. NMR $^1$H (CD$_3$OD, 500 MHz) δ: 7.40-7.29 (m, 5H); 5.11 (m, 2H); 4.50-4.48 (m, 1H); 4.38-4.37 (m, 1H); 3.97 (d, 1H, J=6.95 Hz); 2.41-2.31 (m, 2H); 2.12-1.90 (m, 4H); 1.53 (m, 1H); 1.46 (s, 9H); 1.30 (m, 1H); 0.97-0.92 (m, 12H).

b) Synthesis of (Z-Val-Glu-(OtBu)-Ile-Asp(O-tBu) Methyl Vinyl Sulfone)

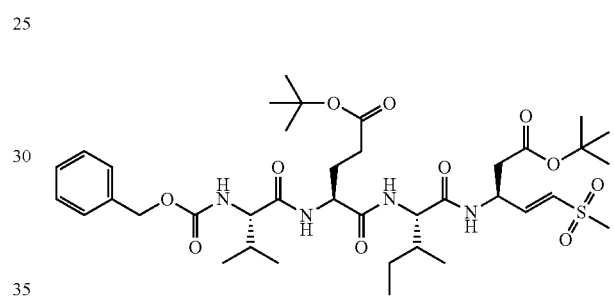

Z-Val-Glu-(OtBu)-Ile-Asp(O-tBu) methyl vinyl sulfone was obtained in the same condition to get (zAsp-(O-tBu)-Trp(N-Me)-Val-Asp-(O-tBu)-methyl vinyl sulfone) (Cpd 36) starting from Z-Val-Glu-(OtBu)-Ile-OH and Asp (β-tert-butyl) methyl vinyl sulfone. The crude was solubilise in small quantity of dichloromethane at 40° C., then added to the samplet of Biotage column (10 g). The purification is carried out first with ethyl acetate/hexane (40%, 12 CV), then dichloromethane/methanol (0 to 15%, 10 CV) to afford the desired compound, obtained as E-isomer.

c) Synthesis of (Z-Val-Glu-Ile-Asp Methyl Vinyl Sulfone)

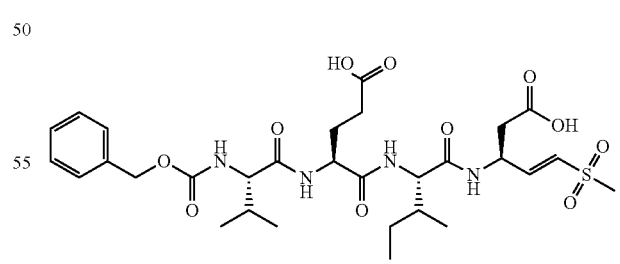

Z-Val-Glu-Ile-Asp methyl vinyl sulfone was obtained as for Synthesis of (zAsp-Trp(N-Me)-Val-Asp-methyl vinyl sulfone) (Cpd 36). NMR $^1$H (CD$_3$OD, 500 MHz) δ: 7.40-7.30 (m, 5H); 6.90-6.68 (m, 2H); 5.14 (m, 2H); 4.99-4.90 (m, 1H); 4.41 (m, 1H); 4.21 (m, 1H); 3.96 (d, 1H, J=6.50 Hz); 3.00 (s, 3H); 2.76 (d, 2H, J=7.05 Hz); 2.47-2.41 (m, 2H); 2.20-1.85 (m, 4H); 1.55 (m, 1H); 1.25 (m, 1H); 0.95 (m, 12H).

Example 10: Synthesis of Compound 105
(Z-Asp-Phg-Val-Asp Ethyl Vinyl Ester)

a) Asp (β-tert-butyl) Ethyl Vinyl Ester Tosyl Salt

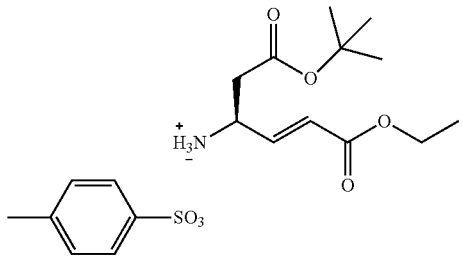

a1) Boc-Asp(β-tert-butyl) Ethyl Vinyl Ester

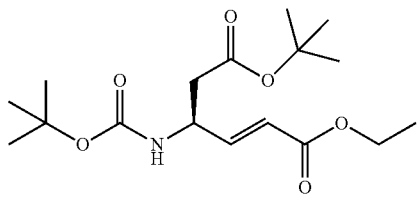 [SMILES: CCOC(=O)/C=C/[C@H](CC(=O)OC(C)(C)C)NC(=O)OC(C)(C)C]

LiHMD (3.64 ml, 1M) was added at −78° C. to a solution of triethylphosphonoacetate in THF (32 ml). The mixture was stirred for 20 min at −78° C., then Boc Asp (OtBu)-H (1 g, 3.64 mmol; described in the previous patents) in THF (8 mL) was added dropwise to the solution. The mixture was stirred for 2 h at −78° C., then 0° C. for 10 min. The solution was poured into a solution of EtOAc/NH$_4$Cl s (75/15 ml) and extracted. The organic layer was dried over MgSO$_4$, filtered and concentrated. The residue was purified on silica using a gradient of Hex/EtOAc to elute 0.51 g of the trans compound. NMR $^1$H (CDCl$_3$, 400 MHz) δ: 6.90 (dd, 1H, J=4.85, 15.60 Hz); 5.97 (dd, 1H, J=1.85, 15.70 Hz); 5.32 (bs, 1H); 4.67 (bs, 1H); 4.21 (q, 2H, J=7.10 Hz); 2.62 (dd, 1H, J=5.45, 15.55 Hz); 2.54 (dd, 1H, J=6.16, 15.65 Hz); 1.47 (s, 9H); 1.46 (s, 9H); 1.30 (t, 3H, J=7.10 Hz).

a2) Asp(β-tert-butyl) Ethyl Vinyl Ester Tosyl Salt

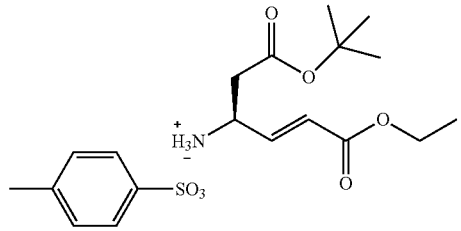

Boc-Asp(β-tert-butyl) ethyl vinyl ester (1.41 g, 4.12 mmol) was solvated in CH$_2$Cl$_2$ (3.4 ml) followed by the addition of Et$_2$O (3.4 ml). p-Toluene sulfonic Acid monohydrate (0.817 g, 1.04 eq) was added over a period of 6 min. The vial was washed with dichloromethane/ether (0.15 ml/0.15 ml). After 15 hours of stirring at room temperature, it was then diluted with Ether (14 mL), the solvent was evaporated under vacuum at room temperature and the obtained residue was washed with cold ether (4 ml) and the surnatant was removed. This operation was repeated twice with cold ether (2*2 ml). The while solid was then dried over vacuum to get Asp(β-tert-butyl) ethyl vinyl ester tosyl salt. NMR $^1$H (DMSO-d6, 500 MHz) δ: 8.18 (bs, 3H); 7.49-7.47 (m, 2H); 7.12 (dd, 2H, J=0.65, 8.40 Hz); 6.82-6.79 (m, 1H); 6.17-6.13 (m, 1H); 4.24 (bs, 1H); 4.19-4.15 (m, 2H); 2.79-2.64 (m, 2H); 2.29 (s, 3H); 1.41 (s, 9H); 1.22 (t, 3H, J=3.95 Hz).

a3) Asp(β-tert-butyl) Ethyl Vinyl Ester Tosyl Salt

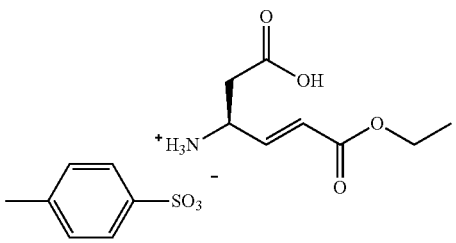

Boc-Asp(β-tert-butyl) ethyl vinyl ester (0.176 g, 0.5 mmol) was solvated in CH$_2$Cl$_2$ (1.3 mL) followed by the addition of Et$_2$O (1.3 mL). p-Toluene sulfonic Acid monohydrate (0.46 g, 4.7 eq) was added. After 15 hours of stirring at room temperature, it was then diluted with Ether (8 mL) and filtered off. The while solid was then dried over vacuum, 0.12 g of the Asp(β-tert-butyl) ethyl vinyl ester tosyl salt was obtained. NMR $^1$H (DMSO-d6, 500 MHz) δ: 8.33-8.01 (bs, 3H, —NH$_3$); 7.49-7.47 (m, 2H); 7.12 (dd, 2H, J=0.60, 8.40 Hz); 6.83 (dd, 1H, J=6.40, 15.95 Hz); 6.16 (dd, 1H, J=1.40, 15.95 Hz); 4.27-4.24 (m, 1H); 4.16 (q, 2H, J=8.35 Hz); 2.76 (d, 2H, J=6.55 Hz); 2.29 (s, 3H); 1.23 (t, 3H, J=7.10 Hz).

a4) Asp(β-tert-butyl) αchlorovinyl Ethyl Vinyl Ester Tosyl Salt

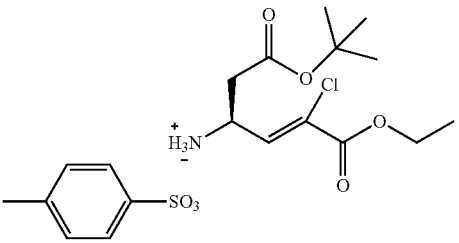

a4-1) Asp(β-tert-butyl) αchlorovinyl Ethyl Vinyl Ester

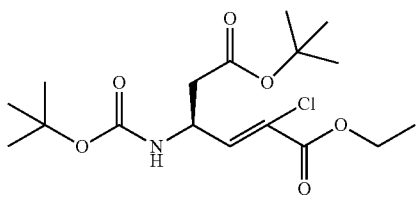 [SMILES: CCOC(=O)/C(Cl)=C/[C@H](CC(=O)OC(C)(C)C)NC(=O)OC(C)(C)C]

1M LiHMDS (1.72 ml) was added to a solution of Ethyl 2-chloro-2(diethoxyphosphoryl) acetate (0.445 g, 1 eq) in THF (25 ml) at −78° C. The reaction was stirred at −78° C. for 20 min and N-Boc Asp(O-t-Bu)-H (0.47 g, 1.72 mmol) was added dropwise in THF over a period of 20 min. The reaction was then stirred for 2 h at −78° C. and then for 10 min at ° C. The solution was poured into a solution of ethyl acetate/NH$_4$Cl (50/20), extracted, dried over MgSO4, filtered and concentrated. The crude was purified on silica using a gradient (2-20%: Ethyl Acetate/Hexane) to get 0.27 g of Asp(β-tert-butyl) αchlorovinyl Ethyl vinyl ester.

a4-2) Asp(β-tert-butyl) αchlorovinyl Ethyl Vinyl Ester Tosyl Salt

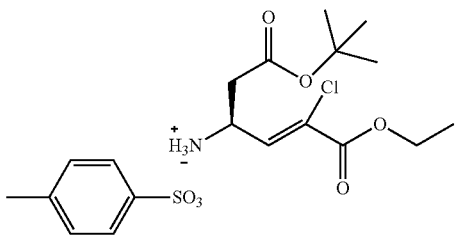

Asp(β-tert-butyl) αchlorovinyl Ethyl vinyl ester (0.27 g, 0.72 mmol) was solvated in CH$_2$Cl$_2$ (0.61 ml) followed by the addition of Et$_2$O (0.61 ml). p-Toluene sulfonic Acid monohydrate (0.14 g, 1.02 eq) was added. After 15 hours of stirring at room temperature, it was then diluted with Ether (4 mL) and filtered off. The solid was then purified on C-18 using 10 g column (pH: 3.5; gradient: 10 to 100% MeOH/Water; 1 ml methanol volume injection). The desired product was dried over vacuum. NMR $^1$H (DMSO-d6, 500 MHz) δ: 8.13 (bs, 3H); 7.49-7.47 (m, 2H); 7.13-7.11 (m, 2H); 6.60-6.55 (m, 1H); 4.88 (bs, 1H); 4.31-4.26 (m, 2H); 2.79-2.64 (m, 2H); 2.29 (s, 3H); 1.41 (s, 9H); 1.29 (t, 3H, J=6.8 Hz).

c) Syntheses of Z-Asp(β-tert-Butyl)-Phg-Val-Asp(β-tert-Butyl)Ethyl Vinyl Esterlog10

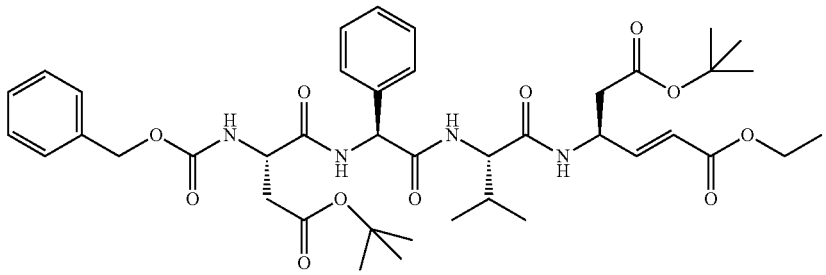 [SMILES: CCOC(=O)/C=C/[C@H](CC(=O)OC(C)(C)C)NC(=O)[C@@H](NC(=O)[C@@H](NC(=O)[C@H](CC(=O)OC(C)(C)C)NC(=O)OCc1ccccc1)c1ccccc1)C(C)C]

The Z-Asp(β-tert-Butyl)-Phg-Val-OH (120 mg, 0.216 mmol) is dissolved in a mix of THF and DMF (1.47 ml/0.3 ml). The mixture was allowed to reach −18° C. (Ice/MeOH bath) before dropwise addition of N-methyl morpholine (24.5 µl) followed 3 min later with dropwise addition of isobutyl chloroformate (29 µl). The mixture was stirred for 10 minutes (the ice bath was changed after 8 minutes when the temperature of the bath dropped −13° C.). Next, Asp(β-tert-butyl) Ethyl Vinyl Ester tosyl salt (92 mg, 1 eq) was added in one shot, followed by dropwise addition of N-methyl morpholine (24.5 µl). The mixture was stirred for 35 minutes, then diluted with 6 ml of dichloromethane and quenched with dropwise addition of water (2 ml) at −12° C. The mixture was stirred 2 minutes at −12° C. and 5 minutes at RT. The mixture was transferred in a separatory funnel and it was diluted with dichloromethane (18 ml). The aqueous layer was washed with dichloromethane (2*15 ml). The combined organic layer was dried over magnesium sulphate. The solvent was evaporated to dryness. The obtained residue was solubilized in a minimum of dichloromethane at 44° C., then added to the samplet of Biotage column (25 g). The purification is carried out first with ethyl acetate/hexane (40%, 12 CV), then dichloromethane/methanol (0 to 15%, 10 CV) to afford 100 mg of Z-Asp(β-tert-Butyl)-Phg-Val-Asp(β-tert-Butyl) Ethyl Vinyl Ester. The compound get out in both purification gradient.

d) Synthesis of Z-Asp-Phg-Val-Asp Ethyl Vinyl Ester

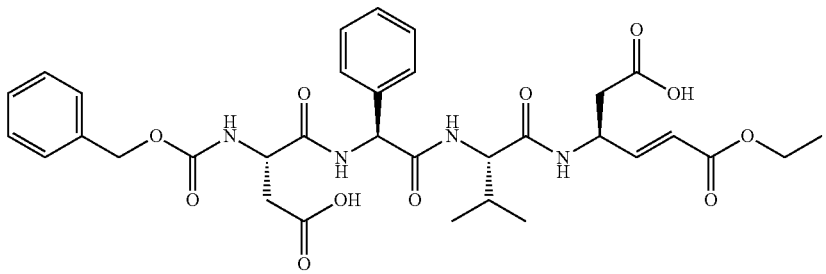 [SMILES: CCOC(=O)/C=C/[C@H](CC(=O)O)NC(=O)[C@@H](NC(=O)[C@@H](NC(=O)[C@H](CC(=O)O)NC(=O)OCc1ccccc1)c1ccccc1)C(C)C]

Z-Asp(β-tert-Butyl)-Phg-Val-Glu(β-tert-buty Ethyl Vinyl Ester (75 mg) was dissolved in dichloromethane (1.2 ml) for 4 min, followed by quick addition of trifluoroacetic acid (1.5 ml). The mixture was stirred at room temperature overnight (15 h). It was then quenched with diethyl ether (10 ml) and the solvent was removed under vacuum. The obtained residue was diluted again with ether (10 ml) and the process was repeated twice. The obtained solid was washed with ether (3*1 ml). The filtrate was removed and the precipitate was dried to give the desired compound. NMR $^1$H (CD$_3$OD, 500 MHz) δ: 7.44-7.30 (m, 10H); 6.88 (dd, 1H, J=5.35, 15.70 Hz); 5.94 (dd, 1H, J=1.60, 15.73 Hz); 5.46 (s, 1H); 5.13-5.09 (m, 2H); 4.60 (t, 1H, J=7.20 Hz); 4.21-4.16 (m, 3H); 2.90-2.76 (m, 2H); 2.60 (dd, 2H, J=1.15, 6.80 Hz); 2.20 (m, 1H); 1.29 (t, 3H, J=7.10 Hz); 0.99 (t, 6H, J=4.80 Hz).

Example 11: Synthesis of Compound 118
(2-Quinoline carbonyl-t-Leu-Pro-Asp Ethyl Vinyl Ester)

a) Syntheses of 2-Quinoline carbonyl-t-Leu-pro-Asp (O-tBu) Ethyl Vinyl Ester

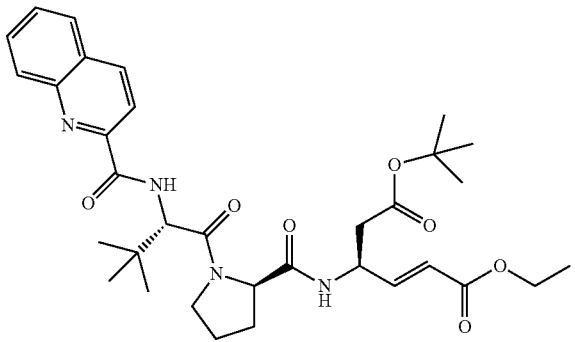 [SMILES: CCOC(=O)/C=C/[C@H](CC(=O)OC(C)(C)C)NC(=O)[C@H]1CCCN1C(=O)[C@@H](NC(=O)c1ccc2ccccc2n1)C(C)(C)C]

2-Quinoline carbonyl-t-Leu-pro-Asp (O-tBu) Ethyl Vinyl Ester has been synthesized in the same condition to get 2-Quinoline carbonyl-t-Leu-pro-Asp(O-tBu)methyl vinyl sulfone (compound 5), starting from 2-Quinoline carbonyl-t-Leu-pro-OH and Asp(β-tert-Butyl)Ethyl Vinyl Ester, Tosyl Salt.

b) Syntheses of 2-Quinoline carbonyl-t-Leu-pro-Asp Ethyl Vinyl Ester

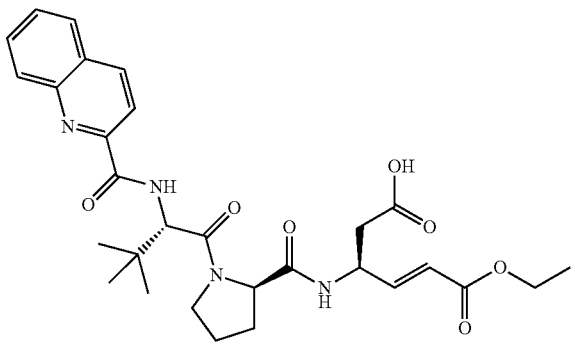 [SMILES: CCOC(=O)/C=C/[C@H](CC(=O)O)NC(=O)[C@H]1CCCN1C(=O)[C@@H](NC(=O)c1ccc2ccccc2n1)C(C)(C)C]

2-Quinoline carbonyl-t-Leu-pro-Asp Ethyl Vinyl Ester has been synthesized in the same condition to get 2-Quinoline carbonyl-t-Leu-pro-Asp methyl vinyl sulfone (compound 6), starting from 2-Quinoline carbonyl-t-Leu-pro-Asp (O-tBu) Ethyl Vinyl Ester (previously described). NMR $^1$H (CD$_3$OD, 500 MHz) δ: 8.52 (d, 1H, J=8.45 Hz); 8.23-8.16 (m, 2H); 8.04-8.00 (m, 1H); 7.89-7.85 (m, 1H); 7.74-7.70 (m, 1H); 6.96 (dd, 1H, J=5.25, 15.70 Hz); 6.01 (dd, 1H, J=1.75, 15.75 Hz); 4.92 (s, 1H); 4.88 (1H, Hidden); 4.46-4.44 (m, 1H); 4.21 (q, 2H, J=7.20 Hz); 4.05-4.02 (m, 1H); 3.84-3.82 (m, 1H); 2.88-2.80 (m, 1H); 2.68 (dd, 1H, J=7.75, 16.35 Hz); 2.29-2.25 (m, 1H); 2.16-2.14 (m, 1H); 2.04-1.95 (m, 2H); 1.30 (t, 3H, J=7.10 Hz); 1.20 (s, 9H).

Example 12: Synthesis of Compound 123
(Z-Val-Glu-Ile-Asp-αchlorovinyl Methyl Vinyl Sulfone)

Same as to get the Cpd 38 from Z-Val-Glu(O-tBu)-Ile-OH and Asp αchlorovinyl methyl vinyl sulfone Tosyl salt (except the hydrolysis with sat NaHCO$_3$ was replaced with water) followed with TFA deprotection.

NMR $^1$H (CD$_3$OD, 500 MHz) δ: 7.39-7.29 (m, 5H); 7.11 (dd, 1H, J=8.45; 1.15 Hz); 5.16-5.04 (m, 3H); 4.41 (m, 1H); 4.2 (m, 1H); 3.94 (m, 1H); 3.1 (s, 3H); 2.93-2.7 (m, 2H); 2.47-2.39 (m, 2H); 2.20-1.1 (m, 6H); 1.06-0.84 (m, 12H).

Example 13: Synthesis of Compound 124
(Z-Val-Glu-Ile-Asp-Ethyl Vinyl Ester)

Same as to get the Cpd 38 from Z-Val-Glu(O-tBu)-Ile-OH and Asp Ethyl vinyl sulfone Tosyl salt followed with TFA deprotection.

NMR $^1$H (CD$_3$OD, 500 MHz) δ: 7.39-7.29 (m, 5H); 6.94-6.90 (m, 1H); 5.96 (ddd, 1H, J=1.25; 3.6; 15.5 Hz); 5.12 (s, 2H); 4.94 (m, 1H); 4.42 (m, 1H); 4.25-4.17 (m, 3H); 3.96 (d, 1H, J=6.8 Hz); 2.7 (m, 2H); 2.45 (m, 2H); 2.25-1.45 (m, 6H); 1.28 (T, 3H, J=7.0 Hz); 1.1-0.89 (m, 12H).

Example 14: Synthesis of Compound 125
(Z-Thr-Glu-Ile-Asp-Ethyl Vinyl Ester)

Same as to get the Cpd 38 from Z-Thr-Glu(O-tBu)-Ile-OH and Asp Ethyl vinyl sulfone Tosyl followed with TFA deprotection.

Example 15: Synthesis of Compound 126
(Z-Val-Glu-Phg-Asp-Ethyl Vinyl Ester)

Same as to get the Cpd 38 from Z-Val-Glu(O-tBu)-Phg-OH and Asp Ethyl vinyl sulfone Tosyl followed with TFA deprotection.

Example 16: Synthesis of Compound 130
(Z-Val-Ala-Asp-αchlorovinyl Methyl Vinyl Sulfone)

Z-Val-Ala-OH was synthesized from Ala-OAllyl and Z-Val-OH which upon Allyl deprotection gave the peptide Z-Val-Ala-OH. It was then coupled with Asp αchlorovinyl methyl vinyl sulfone Tosyl salt followed with TFA deprotection to give Cpd 127 as for Cpd 38.

Example 17: Synthesis of Compound 116 ((4-amino-3-chlorobenzene carbonyl)-t-Leu-Pro-Asp Ethyl Vinyl Ester)

Same as described in Cpd 14 coupling 4-((tert-butoxycarbonyl)amino)-3-chlorobenzene carbonyl-t-Leu-Pro-OH and Asp Ethyl vinyl sulfone Tosyl (purified ethyl acetate/Hexane 40%) followed with TFA deprotection.

Example 18: Synthesis of Compound 133 (Z-Val-Glu-His-Asp Methyl Vinyl Sulfone)

The peptide Z-Val-Glu(O-tBu)-His(N-Boc)-OH was obtained using Fmoc chemistry as described in previous patents, Starting from N-FmocHis-Oallyl and Fmoc Glu(O-tBu)-OH. Fmoc was deprotected with Piperidine in dichloromethane (11 eq, 50 min) to generate His (N-Boc)-Oallyl and (8 eq, 45 min) to generate the peptide Glu(O-tBu)-His (N-Boc)-Oallyl. Some deprotection of allyl group was observed as well and was removed by flash chromatography. The subsequent coupling with Z-Val and allyl deprotection gave the desired Z-Val-Glu(O-tBu)-His(N-Boc)-OH whish upon coupling with Asp methyl vinyl sulfone Tosyl salt followed with TFA deprotection gave Cpd 133 as described in Cpd 84.

Example 19: Synthesis of Compound 119 (2-Quinoline carbonyl-t-Leu-Pro-Asp αchlorovinyl Ethyl Vinyl Ester)

Same as to get compound 6: 2-Quinoline carbonyl-t-Leu-Pro-OH was coupled with αchlorovinyl Ethyl Vinyl Ester salt as to get compound 6 and 36 (except the hydrolysis with saturated sodium bicarbonate was replaced with water). NMR $^1$H (CD$_3$OD, 500 MHz) δ: 8.52 (m, 1H); 8.22-8.17 (m, 2H); 8.02 (d, 1H, J=8.4 Hz); 7.89-7.84 (m, 1H); 7.74-7.70 (m, 1H); 6.60 (d, 1H, J=9.0 Hz); 5.48-5.44 (m, 1H); 4.91 (s, 1H); 4.43-4.4 (m, 1H); 4.33 (q, 2H, J=7.0 Hz); 4.04-4.0 (m, 1H); 3.85-3.80 (m, 1H); 2.96-2.7 (m, 2H); 2.25-1.9 (m, 4H); 1.38 (t, 3H, J=7.2 Hz); 1.19 (s, 9H).

Example 20: Caspase-1 to Caspase-10 Inhibitor Screening Assay

Methods:

The efficacy of an array of compounds as an inhibitor of the activity of Caspases 1 through 10 were assessed by using the respective Caspase Inhibitor Drug Screening Kits (Caspase-1 Catalog #: K151-100, Caspase-2 Catalog #: K152-100, Caspase-3 Catalog #: K153-100, Caspase-4 Catalog #: K154-100, Caspase-5 Catalog #: K155-100, Caspase-6 Catalog #: K156-100, Caspase-7 Catalog #: K157-100, Caspase-8 Catalog #: K158-100, Caspase-9 Catalog #: K159-100, Caspase-10 Catalog #: K160-100, BioVision) following the instructions of the manufacturer. The preferred synthetic peptide substrates for the different caspases were utilized for each assay (Caspase-1 substrate: YVAD-AFC, Caspase-2 substrate: VDVAD-AFC, Caspase-3 substrate: DEVD-AFC, Caspase-4 substrate: LEVD-AFC, Caspase-5 substrate: WEHD-AFC, Caspase-6 substrate: VEID-AFC, Caspase-7 substrate: DEVD-AFC, Caspase-8 substrate: IETD-AFC, Caspase-9 substrate: LEHD-AFC, Caspase-10 substrate: AEVD-AFC). Active caspases cleaved their respective synthetic substrates to release free AFC, which was then quantified by fluorometry.

Briefly, the compounds were first tested at 2 concentrations (10 uM and 100 uM final) to determine if there is a hit. This was done by mixing the compounds with the respective active caspases, after which the corresponding synthetic substrate was added for a final reaction volume of 20 ul. Each condition was tested in duplicates. After a 30-minute incubation period at 37° C., the liberation of AFC was measured as an endpoint assay using the Flexstation3™ (Molecular Devices) with an excitation wavelength of 400 nm and an emission wavelength of 505 nm. The level of inhibition of the activity of the various caspases was determined by comparing the relative fluorescence intensity in samples with or without the compounds using the equation below (*). Subsequently based on the results, an 11-point titration was performed for a group of compounds for a selection of the caspases with final concentrations of 1, 3.3, 10, 33, 100, 333, 1000, 3333, 10000, 33333, 100000 nM. For some samples, a smaller range of concentrations was tested depending on the % Inhibition results at 10 uM and 100 uM. Results were summarized in Tables 2, 2 and 3 herein after. Table 2 represents the IC$_{50}$ values (uM) of the test compounds as inhibitors of the activity of the various caspases. Table 3 shows the % Inhibition of the respective caspase activity for the test compounds at 100 uM, which allows us to distinguish the differences in between samples where no IC$_{50}$ value was determined. Similarly, Table 4 shows the % Inhibition of the respective caspase activity for the test compounds at 10 uM.

(*) RFU (no inhibitor control)-RFU (compound at a specific concentration)

RFU (no inhibitor control)

Results:

The results of a selected list of compounds tested are shown in Tables 2-4.

TABLE 2

IC50 values (μM) of Caspase 1 through 10 Inhibition by the list of compounds

| | IC50 (uM) | | | | | | | | | |
| --- | --- | --- | --- | --- | --- | --- | --- | --- | --- | --- |
| ID | Casp1 | Casp2 | Casp3 | Casp4 | Casp5 | Casp6 | Casp7 | Casp8 | Casp9 | Casp10 |
| 3 | >100 | >100 | >100 | >100 | >100 | >100 | >100 | >100 | >100 | >100 |
| 42 | 33.8 | >100 | >100 | 17.11 | 12.39 | >100 | >100 | >100 | >100 | 34.05 |
| 6 | 0.04 | >100 | >100 | 1.55 | 2.32 | >100 | >100 | >100 | ~100 | 55.95 |
| 38 | 2.7 | >100 | 6.96 | 0.375 | 19.55 | 0.6 | >100 | 0.66 | 0.79 | 0.13 |
| 40 | 0.026 | >100 | 6.55 | 0.18 | 0.75 | ~100 | 23.69 | 5.93 | 1.74 | 3.29 |
| 36 | 3.8 | >100 | 0.09 | 9.02 | 25.43 | >100 | 0.85 | >100 | 16.93 | 18.64 |
| 14 | 0.02 | >100 | >100 | 0.09 | 0.56 | >100 | 24.5 | 12.9 | 2.3 | 2.67 |
| 10 | 0.12 | >100 | >100 | 1.92 | 3.0 | >100 | 53.6 | 14.7 | 3.23 | 4.67 |
| 26 | 4.29 | 4.36 | 0.12 | 3.27 | 9.88 | >100 | 0.38 | 2.23 | 0.66 | 0.16 |
| 30 | 8.0 | 53.7 | 3.4 | 9.94 | ~100 | >100 | 6.12 | 32.5 | 10.8 | 12.9 |
| 20 | 1.4 | >100 | >100 | 1.56 | 8.39 | >100 | >100 | >100 | >100 | 12.5 |
| 32 | 13.3 | 13.14 | 0.28 | 5.63 | 35.16 | >100 | 0.55 | 4.08 | 1.12 | 0.42 |
| 8 | 0.88 | >100 | >100 | 0.63 | 5.9 | >100 | >100 | >100 | 47.3 | 18.0 |
| 28 | 10.6 | 30.4 | 0.78 | 5.22 | 46.2 | >100 | 2.5 | 27.6 | 9.07 | 2.45 |
| 21 | >100 | >100 | >100 | >100 | >100 | >100 | >100 | >100 | >100 | >100 |

TABLE 2-continued

IC50 values (uM) of Caspase 1 through 10 Inhibition by the list of compounds

| ID | Casp1 | Casp2 | Casp3 | Casp4 | Casp5 | Casp6 | Casp7 | Casp8 | Casp9 | Casp10 |
|---|---|---|---|---|---|---|---|---|---|---|
| 22 | >100 | >100 | >100 | >100 | >100 | >100 | >100 | >100 | >100 | >100 |
| 24 | >100 | >100 | >100 | >100 | >100 | >100 | >100 | >100 | >100 | >100 |
| 2 | >100 | >100 | >100 | >100 | >100 | >100 | 64.4 | >100 | 50.9 | >100 |
| 16 | >100 | >100 | >100 | >100 | >100 | >100 | >100 | >100 | >100 | >100 |
| 4 | >100 | >100 | >100 | >100 | >100 | >100 | >100 | >100 | >100 | >100 |
| 18 | >100 | >100 | >100 | >100 | >100 | >100 | >100 | >100 | >100 | >100 |
| 84 | >100 | >100 | 15.25 | >100 | >100 | >100 | 49.88 | >100 | >100 | >100 |
| 44 | >100 | >100 | >100 | >100 | >100 | >100 | >100 | >100 | >100 | >100 |
| 105 | 1.05 | >100 | 0.03 | 0.51 | >100 | >100 | 0.15 | 2.62 | 1.0 | 0.59 |
| 116 | 0.01 | >100 | 33.4 | 0.03 | 0.13 | >100 | 3.6 | 0.60 | 0.83 | 0.55 |
| 57 | 7.9 | | 1.27 | >100 | 16 | >100 | 0.15 | | | 0.05 |
| 117 | 0.11 | | >100 | 0.07 | 0.90 | >100 | >100 | 1.40 | | >100 |
| 118 | 0.03 | >100 | >100 | 0.6 | 1.95 | >100 | >100 | 21.14 | 8.90 | 8.05 |
| 123 | 3.88 | >100 | 1.34 | 1.8 | 4.2 | 0.23 | >100 | 0.53 | 6.4 | 0.19 |
| 124 | 0.78 | 10 | 0.58 | 1.27 | 3.77 | 0.29 | >100 | 0.19 | 7.5 | 0.03 |
| 126 | 1.0 | >100 | 2.78 | 0.77 | 8.58 | 0.48 | >100 | 0.08 | >100 | 0.002 |

TABLE 3

% Inhibition of Caspase 1 through 10 activity by the list of compounds at 100 uM.

| ID | Casp1 | Casp2 | Casp3 | Casp4 | Casp5 | Casp6 | Casp7 | Casp8 | Casp9 | Casp10 |
|---|---|---|---|---|---|---|---|---|---|---|
| 3 | 26% | 0% | 5% | 2% | 0% | 0% | 9% | 23% | 17% | 50% |
| 42 | 72% | 0% | 0% | 100% | 93% | 4% | 0% | 30% | 26% | 79% |
| 6 | 100% | 10% | 1% | 100% | 99% | 3% | 2% | 22% | 51% | 74% |
| 38 | 97% | 4% | 89% | 100% | 81% | 96% | 31% | 100% | 97% | 100% |
| 40 | 100% | 10% | 94% | 100% | 100% | 51% | 90% | 96% | 99% | 99% |
| 36 | 94% | 19% | 100% | 99% | 50% | 19% | 99% | 33% | 87% | 98% |
| 14 | 100% | 10% | 18% | 100% | 100% | 30% | 91% | 95% | 99% | 100% |
| 10 | 100% | 6% | 16% | 100% | 98% | 0% | 73% | 94% | 98% | 98% |
| 26 | 99% | 96% | 100% | 100% | 91% | 7% | 100% | 99% | 100% | 100% |
| 30 | 92% | 66% | 95% | 100% | 50% | 2% | 97% | 79% | 92% | 92% |
| 20 | 99% | 6% | 5% | 100% | 96% | 0% | 0% | 23% | 44% | 93% |
| 32 | 86% | 86% | 100% | 100% | 77% | 1% | 100% | 98% | 100% | 100% |
| 8 | 100% | 5% | 5% | 100% | 97% | 1% | 0% | 23% | 73% | 90% |
| 28 | 90% | 79% | 99% | 100% | 69% | 4% | 99% | 80% | 93% | 99% |
| 21 | 2% | 18% | 4% | 4% | 7% | 10% | 0% | 4% | 10% | 0% |
| 22 | 0% | 13% | 0% | 0% | 0% | 0% | 0% | 7% | 0% | 14% |
| 24 | 10% | 0% | 0% | 0% | 0% | 0% | 0% | 0% | 0% | 15% |
| 2 | 5% | 0% | 39% | 6% | 12% | 19% | 72% | 33% | 70% | 31% |
| 16 | 0% | 3% | 30% | 0% | 10% | 0% | 19% | 14% | 0% | 35% |
| 4 | 0% | 0% | 7% | 0% | 1% | 0% | 0% | 13% | 0% | 43% |
| 18 | 1% | 0% | 2% | 0% | 1% | 8% | 7% | 0% | 9% | 0% |
| 84 | 0% | 3% | 88% | 0% | 0% | 5% | 76% | 10% | 6% | 0% |
| 44 | 0% | 3% | 0% | 0% | 0% | 0% | 0% | 7% | 0% | 15% |
| 105 | 96% | 17% | 100% | 98% | 41% | 10% | 99% | 79% | 92% | 99% |
| 118 | 100% | 10% | 15% | 100% | 99% | 6% | 8% | 89% | 92% | 97% |

TABLE 4

% Inhibition of Caspase 1 through 10 activity by the list of compounds at 10 uM.

| ID | Casp1 | Casp2 | Casp3 | Casp4 | Casp5 | Casp6 | Casp7 | Casp8 | Casp9 | Casp10 |
|---|---|---|---|---|---|---|---|---|---|---|
| 3 | 18% | 0% | 0% | 0% | 0% | 0% | 0% | 0% | 0% | 15% |
| 42 | 26% | 0% | 0% | 28% | 43% | 6% | 0% | 12% | 0% | 13% |
| 6 | 98% | 2% | 1% | 99% | 86% | 0% | 0% | 0% | 1% | 3% |
| 38 | 81% | 2% | 63% | 100% | 32% | 88% | 0% | 97% | 82% | 100% |
| 40 | 99% | 1% | 63% | 100% | 95% | 7% | 19% | 61% | 87% | 80% |
| 36 | 75% | 0% | 98% | 57% | 14% | 0% | 95% | 0% | 39% | 31% |
| 14 | 99% | 1% | 7% | 100% | 96% | 3% | 13% | 46% | 77% | 81% |
| 10 | 90% | 3% | 12% | 91% | 78% | 0% | 3% | 34% | 76% | 65% |
| 26 | 69% | 70% | 98% | 88% | 50% | 0% | 99% | 82% | 95% | 99% |
| 30 | 55% | 11% | 68% | 50% | 8% | 0% | 68% | 22% | 48% | 43% |

TABLE 4-continued

% Inhibition of Caspase 1 through 10 activity by the list of compounds at 10 uM.

| | % Inhibition at 10 uM | | | | | | | | | |
|---|---|---|---|---|---|---|---|---|---|---|
| ID | Casp1 | Casp2 | Casp3 | Casp4 | Casp5 | Casp6 | Casp7 | Casp8 | Casp9 | Casp10 |
| 20 | 81% | 7% | 1% | 85% | 55% | 0% | 0% | 8% | 8% | 42% |
| 32 | 44% | 43% | 96% | 76% | 23% | 0% | 97% | 69% | 91% | 97% |
| 8 | 91% | 3% | 3% | 88% | 65% | 2% | 0% | 8% | 24% | 27% |
| 28 | 49% | 22% | 91% | 73% | 14% | 2% | 87% | 20% | 54% | 82% |
| 21 | 2% | 14% | 0% | 0% | 3% | 1% | 0% | 3% | 1% | 0% |
| 22 | 0% | 12% | 0% | 0% | 11% | 1% | 0% | 3% | 2% | 15% |
| 24 | 3% | 0% | 0% | 1% | 0% | 0% | 1% | 0% | 0% | 21% |
| 2 | 0% | 0% | 1% | 0% | 10% | 1% | 3% | 2% | 16% | 0% |
| 16 | 0% | 1% | 5% | 0% | 0% | 0% | 3% | 5% | 0% | 26% |
| 4 | 0% | 0% | 4% | 0% | 0% | 0% | 0% | 6% | 0% | 36% |
| 18 | 1% | 0% | 4% | 0% | 0% | 0% | 0% | 0% | 0% | 14% |
| 84 | 0% | 0% | 39% | 0% | 0% | 0% | 9% | 9% | 0% | 2% |
| 44 | 0% | 0% | 0% | 0% | 0% | 0% | 0% | 0% | 0% | 4% |
| 105 | 84% | 0% | 99% | 100% | 41% | 13% | 99% | 77% | 92% | 96% |
| 118 | 100% | 4% | 0% | 100% | 88% | 3% | 3% | 36% | 53% | 59% |

We claim:

1. A compound of Formula I:

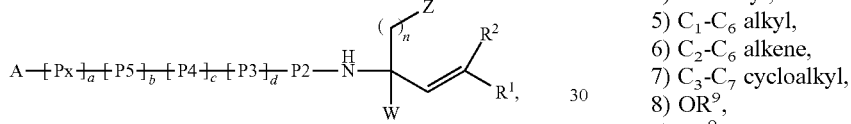

wherein
a is 0;
b is 0;
c is 0;
d is 0 or 1;
the line "-" when located between P2 and P3 is a peptide bond or a peptidomimetic bond, wherein when the line "-" is a peptidomimetic bond, the peptidomimetic bond is a bond selected from the group consisting of a $CH_2NH$ bond, a $CO-CH_2$ bond, an azapeptide bond, and a retroinverso bond;
P3 is a natural or non-natural amino acid residue;
P2 is alanine, arginine, aspartic acid, asparagine, cysteine, glutamine, isoleucine, histidine, leucine, lysine, methionine, phenylalanine, proline, serine, tryptophan, tyrosine, or a non-natural amino acid residue;
$R^1$ and $R^2$ are either in the cis configuration or the trans configuration;
n is 0, 1, or 3;
wherein Z is Tetrazol, Cyano, $COR^4$, or $COR^5$;
W is H, alkyl, OH, $OR^9$, $NH_2$, $NHR^9$, $NHSOR^9$, halogen, $COR^4$, $COR^9$, CN, $OCOR^9$, $OCO_2R^9$, NO, $NO_2$, $NR^7R^8$, $NHSO_2R^9$, $NHCOR^9$, $SO_2R^9$, $SOR^9$, or $SR^9$;
A is
 1) H,
 2) $R^3$—$CH_2OC(O)$—,
 3) (4-amino-3-chloro-benzene)-C(O)—, or
 4) quinoline-C(O)—;
$R^1$ is
 1) $SO_2R^5$,
 2) $SO_3R^5$,
 3) $SOR^5$,
 4) $CO_2R^5$, or
 5) $COR^5$;

$R^2$ is
 1) $R^1$,
 2) H,
 3) halogen,
 4) haloalkyl,
 5) $C_1$-$C_6$ alkyl,
 6) $C_2$-$C_6$ alkene,
 7) $C_3$-$C_7$ cycloalkyl,
 8) $OR^9$,
 9) $SR^9$,
 10) $N^+(R^4)_3$,
 11) $OCOR^6$,
 12) $OCO_2R^6$,
 13) $NR^7R^8$,
 14) $NHSO_2R^6$,
 15) $NHCOR^6$,
 16) aryl,
 17) heteroaryl, or
 18) heterocyclyl;
$R^3$ is
 1) $C_1$-$C_6$ alkyl,
 2) aryl-$C_1$-$C_6$ alkyl,
 3) heteroaryl, or
 4) heterocyclyl;
$R^4$ is
 1) OH, or
 2) $OC_1$-$C_6$ alkyl;
$R^5$ is
 1) H,
 2) $C_1$-$C_6$ alkyl,
 3) $C_2$-$C_6$ alkene,
 4) $C_3$-$C_7$ cycloalkyl,
 5) haloalkyl,
 6) aryl,
 7) heteroaryl,
 8) heterocyclyl,
 9) $NHCH_2C(O)OH$, or
 10) (D) or (L) natural or non-natural amino acids optionally protected with an amino acid protecting group;
$R^6$ is
 1) any (D) or (L) amino acid residue,
 2) $C_1$-$C_6$ alkyl,
 3) $C_3$-$C_7$ cycloalkyl, 4) aryl,
5) heteroaryl, or
6) heterocyclyl,
in which the alkyl or the cycloalkyl are optionally substituted with one or more $R^{10}$ substituents; and in which the aryl, heteroaryl or heterocyclyl are optionally substituted with one or more $R^{20}$ substituents;

$R^7$ and $R^8$ are independently selected from:
1) H,
2) $C_1$-$C_6$ alkyl,
3) $C_3$-$C_7$ cycloalkyl,
4) haloalkyl,
5) aryl,
6) heteroaryl, or
7) heterocyclyl,
wherein the alkyl and the cycloalkyl are optionally substituted with one or more $R^{10}$ substituents, and the aryl, the heteroaryl and the heterocyclyl are optionally substituted with one or more $R^{20}$ substituents;

$R^9$ is
1) H,
2) $C_1$-$C_6$ alkyl,
3) $C_3$-$C_7$ cycloalkyl,
4) aryl,
5) heteroaryl, or
6) heterocyclyl,
in which the alkyl or the cycloalkyl are optionally substituted with one or more $R^{10}$ substituents; and in which the aryl, heteroaryl or heterocyclyl are optionally substituted with one or more $R^{20}$ substituents;

$R^{10}$ is independently selected from:
1) halogen,
2) $C_1$-$C_6$ alkyl,
3) $C_3$-$C_7$ cycloalkyl,
4) haloalkyl,
5) aryl,
6) heteroaryl,
7) heterocyclyl,
8) $OR^9$,
9) $S(O)_m R^9$,
10) $NR^7 R^8$,
11) $COR^9$,
12) $C(O)OR^9$,
13) $OC(O)R^9$,
14) $SC(O)R^9$,
15) $CONR^7 R^8$, or
16) $S(O)_2 NR^7 R^8$;
wherein m is an integer of 0, 1, or 2;

$R^{20}$ is independently selected from:
1) halogen,
2) $NO_2$,
3) CN,
4) $C_1$-$C_6$ alkyl,
5) haloalkyl,
6) $C_3$-$C_7$ cycloalkyl,
7) $OR^7$,
8) $NR^7 R^8$,
9) $SR^7$,
10) aryl,
11) heteroaryl,
12) heterocyclyl,
13) $SO_2 R^5$,
14) $SO_3 R^5$,
15) $SOR^5$,
16) $SONHR^5$,
17) $SO_2 NHR^5$,
18) $PO_3 R^5$,
19) $PO(OR^5)_2$,
20) $PO(OR^5)$,
21) $COR^5$,
22) $COR^7$,
23) $CO_2 R^7$,
24) $S(O)_m R^7$,
25) $CONR^7 R^8$, or
26) $S(O)_2 NR^7 R^8$,
wherein the alkyl and the cycloalkyl are optionally substituted with one or more $R^6$ substituents; and wherein the aryl, the heteroaryl, or the heterocyclyl are optionally substituted with one or more $R^{30}$; wherein m is an integer of 0, 1, or 2; and $R^{30}$ is
1) $NO_2$,
2) $C_2$-$C_6$ alkene-$R^{20}$,
3) $SO_2 R^5$,
4) $SOR^5$,
5) $SONHR^5$,
6) $SO_2 NHR^5$,
7) CN,
8) $CO_2 R^5$,
9) $COR^5$,
10) $PO_3 R^5$,
11) $PO(OR^5)_2$, or
12) $PO(OR^5)$;

or a pharmaceutically acceptable salt or ester thereof, or the compound is labeled with a detectable label or an affinity tag thereof;
wherein the compound is a caspase inhibitor.

2. The compound according to claim 1, in which A is H.

3. The compound according to claim 1, in which A is selected from the group consisting of quinoline-C(O)—, and (4-amino-3-chlorobenzene)-C(O)—.

4. The compound according to claim 1, in which Z is $COR^4$ and $R^4$ is selected from the group consisting of OH, $OCH_3$, and $OCH_2 CH_3$.

5. The compound according to claim 1, in which Z is $COR^4$ and $R^4$ is OH.

6. The compound according to claim 1, in which d is 0.

7. The compound according to claim 1, in which $R^1$ is in the trans configuration.

8. The compound according to claim 1, wherein $R^1$ is
1) $SO_2 R^5$,
2) $SO_3 R^5$,
3) $SOR^5$,
4) $CO_2 R^5$, or
5) $COR^5$; and
wherein $R^5$ is H, $C_1$-$C_6$ alkyl, aryl, or heterocyclyl.

9. The compound according to claim 1, in which $R^2$ is
1) H,
2) halogen,
3) haloalkyl,
4) $C_1$-$C_6$ alkyl, or
5) $C_3$-$C_7$ cycloalkyl.

10. The compound according to claim 9, in which $R^2$ is H or Cl.

11. The compound according to claim 10, in which $R^2$ is Cl.

12. The compound according to claim 9, wherein the compound is selected from the group consisting of: 4-amino-3-chlorobenzene carbonyl-t-Leu-Pro-Asp methyl vinyl sulfone (compound 14), 2-Quinoline carbonyl-t-Leu-Pro-Asp methyl vinyl sulfone (compound 6), Quinoline-6-carbonyl-t-Leu-Pro-Asp methyl vinyl sulfone (compound 10), 2-Quinoline carbonyl-t-Leu-(Azetidine-2-carbonyl)-Asp methyl vinyl sulfone (compound 20), (4-amino-3-chlorobenzene carbonyl)-t-Leu-Pro-β-Cyano-Ala methyl vinyl sulfone (compound 90), 4-amino-3-chlorobenzene carbonyl-t-Leu-Pro-β-Cyano-Ala α-chlorovinyl methyl vinyl sulfone (compound 91), (4-amino-3-chlorobenzene carbonyl-t-Leu-Pro-(β-1H tetrazole-Ala) methyl vinyl sulfone (compound 92), 4-amino-3-chlorobenzene carbonyl)-t-Leu-Pro-(β-1H tetrazole-Ala) α-chlorovinyl methyl vinyl sulfone (compound 93), 2-Quinoline carbonyl-t-Leu-Pro-β-Cyano-Ala methyl vinyl sulfone (compound 94), 2-Quinoline carbonyl-t-Leu-Pro-(β-Cyano-Ala) α-chlorovinyl methyl vinyl sulfone (compound 95), 2-Quinoline carbonyl-t-Leu-Pro-(β-1H tetrazole-Ala) methyl vinyl sulfone (compound 96), 2-Quinoline carbonyl-t-Leu-Pro-(β-1H tetrazole-Ala) α-chlorovinyl methyl vinyl sulfone (compound 97), (4-amino-3-chlorobenzene carbonyl)-t-Leu-Pro-(β-1H tetrazole-Ala) α-chlorovinyl Ethyl Vinyl Ester (compound 113), (4-amino-3-chlorobenzene carbonyl)-t-Leu-Pro-(β-1H tetrazole-Ala) Ethyl Vinyl Ester (compound 112), 4-amino-3-chlorobenzene carbonyl-t-Leu-Pro-Asp α-chlorovinyl Ethyl Vinyl Ester (compound 117), 2-Quinoline carbonyl-t-Leu-Pro-(β-1H tetrazole-Ala) Ethyl Vinyl Ester (compound 114), 2-Quinoline carbonyl-t-Leu-Pro-(β-1H tetrazole-Ala) α-chlorovinyl Ethyl Vinyl Ester (compound 115), 4-amino-3-chlorobenzene carbonyl-t-Leu-Pro-Asp Ethyl Vinyl Ester (compound 116), 2-Quinoline carbonyl-t-Leu-Pro-Asp Ethyl Vinyl Ester (compound 118), and 2-Quinoline carbonyl-t-Leu-Pro-Asp α-chlorovinyl Ethyl Vinyl Ester (compound 119).

13. The compound according to claim 1, in which n is 1.

14. A compound of Formula IA:

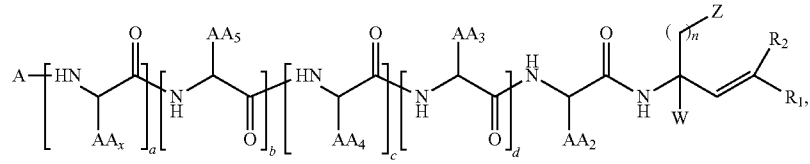

IA wherein
a is 0;
b is 0;
c is 0;
d is 0 or 1;
$AA_3$ is the side chain of a natural or non-natural amino acid;
$AA_2$ is the side chain of alanine, arginine, aspartic acid, asparagine, cysteine, glutamine, isoleucine, histidine, leucine, lysine, methionine, phenylalanine, proline, serine, tryptophan, tyrosine, or a non-natural amino acid;
$R^1$ and $R^2$ can be either in the cis configuration or the trans configuration;
n is 0, 1, or 3;
Z is Tetrazol, Cyano, $COR^4$, or $COR^5$;
W is H, alkyl, OH, $OR^9$, $NH_2$, $NHR^9$, $NHSOR^9$, halogen, $COR^4$, $COR^9$, CN, $OCOR^9$, $OCO_2R^9$, NO, $NO_2$, $NR^7R^8$, $NHSO_2R^9$, $NHCOR^9$, $SO_2R^9$, $SOR^9$, or $SR^9$;
A is
 1) H,
 2) $R^3$—$CH_2OC(O)$—,
 3) (4-amino-3-chloro-benzene)-C(O)—, or
 4) quinoline-C(O)—;
$R^1$ is
 1) $SO_2R^5$,
 2) $SO_3R^5$,
 3) $SOR^5$,
 4) $CO_2R^5$, or
 5) $COR^5$;
$R^2$ is
 1) $R^1$,
 2) H,
 3) halogen,
 4) haloalkyl,
 5) $C_1$-$C_6$ alkyl,
 6) $C_2$-$C_6$ alkene,
 7) $C_3$-$C_7$ cycloalkyl,
 8) $OR^9$,
 9) $SR^9$,
 10) $N^+(R^4)_3$,
 11) $OCOR^6$,
 12) $OCO_2R^6$,
 13) $NR^7R^8$,
 14) $NHSO_2R^6$,
 15) $NHCOR^6$,
 16) aryl,
 17) heteroaryl, or
 18) heterocyclyl;
$R^3$ is
 1) $C_1$-$C_6$ alkyl,
 2) aryl-$C_1$-$C_6$ alkyl,
 3) heteroaryl, or
 4) heterocyclyl;
$R^4$ is
 1) OH, or
 2) $OC_1$-$C_6$ alkyl;
$R^5$ is
 1) H,
 2) $C_1$-$C_6$ alkyl,
 3) $C_2$-$C_6$ alkene,
 4) $C_3$-$C_7$ cycloalkyl,
 5) haloalkyl,
 6) aryl,
 7) heteroaryl,
 8) heterocyclyl,
 9) $NHCH_2C(O)OH$, or
 10) (D) or (L) natural or non-natural amino acids optionally protected with an amino acid protecting group;
$R^6$ is
 1) any (D) or (L) amino acid residue,
 2) $C_1$-$C_6$ alkyl,
 3) $C_3$-$C_7$ cycloalkyl,
 4) aryl,
 5) heteroaryl, or
 6) heterocyclyl,
in which the alkyl or the cycloalkyl are optionally substituted with one or more $R^{10}$ substituents; and in which the aryl, heteroaryl or heterocyclyl are optionally substituted with one or more $R^{20}$ substituents;

$R^7$ and $R^8$ are independently selected from:
1) H,
2) $C_1$-$C_6$ alkyl,
3) $C_3$-$C_7$ cycloalkyl,
4) haloalkyl,
5) aryl,
6) heteroaryl, or
7) heterocyclyl,
wherein the alkyl and the cycloalkyl are optionally substituted with one or more $R^{10}$ substituents, and the aryl, the heteroaryl and the heterocyclyl are optionally substituted with one or more $R^{20}$ substituents;

$R^9$ is
1) H,
2) $C_1$-$C_6$ alkyl,
3) $C_3$-$C_7$ cycloalkyl,
4) aryl,
5) heteroaryl, or
6) heterocyclyl,
in which the alkyl or the cycloalkyl are optionally substituted with one or more $R^{10}$ substituents; and in which the aryl, heteroaryl or heterocyclyl are optionally substituted with one or more $R^{20}$ substituents;

$R^{10}$ is independently selected from:
1) halogen,
2) $C_1$-$C_6$ alkyl,
3) $C_3$-$C_7$ cycloalkyl,
4) haloalkyl,
5) aryl,
6) heteroaryl,
7) heterocyclyl,
8) $OR^9$,
9) $S(O)_m R^9$,
10) $NR^7 R^8$,
11) $COR^9$,
12) $C(O)OR^9$,
13) $OC(O)R^9$,
14) $SC(O)R^9$,
15) $CONR^7 R^8$, or
16) $S(O)_2 NR^7 R^8$,
wherein m is an integer of 0, 1, or 2;

$R^{20}$ is independently selected from:
1) halogen,
2) $NO_2$,
3) CN,
4) $C_1$-$C_6$ alkyl,
5) haloalkyl,
6) $C_3$-$C_7$ cycloalkyl,
7) $OR^7$,
8) $NR^7 R^8$,
9) $SR^7$,
10) aryl,
11) heteroaryl,
12) heterocyclyl,
13) $SO_2 R^5$,
14) $SO_3 R^5$,
15) $SOR^5$,
16) $SONHR^5$,
17) $SO_2 NHR^5$,
18) $PO_3 R^5$,
19) $PO(OR^5)_2$,
20) $PO(OR^5)$,
21) $COR^5$,
22) $COR^7$,
23) $CO_2 R^7$,
24) $S(O)_m R^7$,
25) $CONR^7 R^8$, or
26) $S(O)_2 NR^7 R^8$,
wherein the alkyl and the cycloalkyl are optionally substituted with one or more $R^6$ substituents; and wherein the aryl, the heteroaryl, or the heterocyclyl are optionally substituted with one or more $R^{30}$; wherein m is an integer of 0, 1, or 2; and $R^{30}$ is
1) $NO_2$,
2) $C_2$-$C_6$ alkene-$R^{20}$,
3) $SO_2 R^5$,
4) $SOR^5$,
5) $SONHR^5$,
6) $SO_2 NHR^5$,
7) CN,
8) $CO_2 R^5$,
9) $COR^5$,
10) $PO_3 R^5$,
11) $PO(OR^5)_2$, or
12) $PO(OR^5)$;

or a pharmaceutically acceptable salt or ester thereof, or the compound is labeled with a detectable label or an affinity tag thereof;
wherein the compound is a caspase inhibitor.

15. The compound according to claim 14, in which A is H.

16. The compound according to claim 14, in which A is quinolone-C(O)—, or (4-amino-3-Chlorobenzene)-CO—.

17. The compound according to claim 14, in which Z is $COR^4$ and $R^4$ is OH, $OCH_3$, or $OCH_2 CH_3$.

18. The compound according to claim 14, in which Z is $COR^4$ and $R^4$ is OH.

19. The compound according to claim 14, in which d is 0.

20. The compound according to claim 14, in which $R^1$ is in the trans configuration.

21. The compound according to claim 14, wherein $R^1$ is
1) $SO_2 R^5$,
2) $SO_3 R^5$,
3) $SOR^5$,
4) $CO_2 R^5$, or
5) $COR^5$;
wherein $R^5$ is H, $C_1$-$C_6$ alkyl, aryl, or heterocyclyl.

22. The compound according to claim 14, in which $R^2$ is
1) H,
2) halogen,
3) haloalkyl,
4) $C_1$-$C_6$ alkyl, or
5) $C_3$-$C_7$ cycloalkyl.

23. The compound according to claim 22, in which $R^2$ is H or Cl.

24. The compound according to claim 23, in which $R^2$ is Cl.

25. The compound according to claim 14, wherein
A is
1) H, or
2) $R^3$—$CH_2 OC(O)$; and
$AA_2$ is the (R) or (S) amino acid side chain of 2-azetidine, Leu, Pro, Met, Ala, His, Ser (O-phosphate), Tyr, Trp, Ile, or Lys.

26. A compound of Formula IIIA 2a:

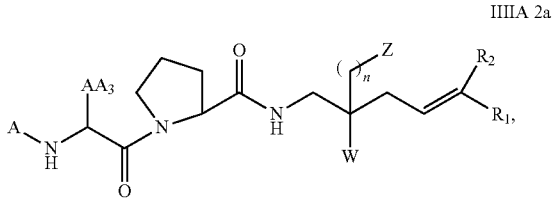

IIIA 2a wherein AA₃ is the side chain of a natural or non-natural amino acids;
R¹ and R² can be either in the cis configuration or the trans configuration;
n is 0, 1, or 3;
Z is Tetrazol, Cyano, COR⁴, or COR⁵;
W is H, alkyl, OH, OR⁹, NH₂, NHR⁹, NHSOR⁹, halogen, COR⁴, COR⁹, CN, OCOR⁹, OCO₂R⁹, NO, NO₂, NR⁷R⁸, NHSO₂R⁹, NHCOR⁹, SO₂R⁹, SOR⁹, or SR⁹;
A is
  1) H,
  2) $C_1$-$C_6$ alkyl,
  3) aryl,
  4) heteroaryl,
  5) heterocyclyl,
  6) $R^3$—C(O)—,
  7) $R^3$—OC(O)—,
  8) $R^3$—$CH_2$OC(O)—,
  9) $R^3$—C(O)O—,
  10) $R^3$—S(O)₂—,
  11) (4-amino-3-chloro-benzene)-C(O)—,
  12) $PhCH_2$OC(O)—, or
  13) quinoline-C(O)—;
R¹ is
  1) aryl,
  2) heteroaryl,
  3) heterocyclyl,
  4) $C_2$-$C_6$ alkene-$R^{20}$,
  5) $SO_2R^5$,
  6) $SO_3R^5$,
  7) $SOR^5$,
  8) $SONHR^5$,
  9) $SO_2NHR^5$,
  10) CN,
  11) $CO_2R^5$,
  12) $COR^5$,
  13) $PO_3R^5$,
  14) $PO(OR^5)_2$, or
  15) $PO(OR^5)$,
wherein the aryl, the heteroaryl, or the heterocyclyl are optionally substituted with one or more $R^{30}$;
R² is
  1) $R^1$,
  2) H,
  3) halogen,
  4) haloalkyl,
  5) $C_1$-$C_6$ alkyl,
  6) $C_2$-$C_6$ alkene,
  7) $C_3$-$C_7$ cycloalkyl,
  8) $OR^9$,
  9) $SR^9$,
  10) $N^+(R^4)_3$,
  11) $OCOR^6$,
  12) $OCO_2R^6$,
  13) $NR^7R^8$,
  14) $NHSO_2R^6$,
  15) $NHCOR^6$,
  16) aryl,
  17) heteroaryl, or
  18) heterocyclyl;
R³ is
  1) $C_1$-$C_6$ alkyl,
  2) aryl-$C_1$-$C_6$ alkyl,
  3) heteroaryl, or
  4) heterocyclyl;
R⁴ is
  1) OH,
  2) $OC_1$-$C_6$ alkyl,
  3) $NR^7R^8$,
  4) $NHSO_2R^9$,
  5) alkyl, or
  6) heteroalkyl;
R⁵ is
  1) H,
  2) $C_1$-$C_6$ alkyl,
  3) $C_2$-$C_6$ alkene,
  4) $C_3$-$C_7$ cycloalkyl,
  5) haloalkyl,
  6) aryl,
  7) heteroaryl,
  8) heterocyclyl,
  9) $NHCH_2C(O)OH$, or
  10) (D) or (L) natural or non-natural amino acids optionally protected with an amino acid protecting group;
R⁶ is
  1) any (D) or (L) amino acid residue,
  2) $C_1$-$C_6$ alkyl,
  3) $C_3$-$C_7$ cycloalkyl,
  4) aryl,
  5) heteroaryl, or
  6) heterocyclyl,
in which the alkyl or the cycloalkyl are optionally substituted with one or more $R^{10}$ substituents; and in which the aryl, heteroaryl or heterocyclyl are optionally substituted with one or more $R^{20}$ substituents;
R⁷ and R⁸ are independently selected from:
  1) H,
  2) $C_1$-$C_6$ alkyl,
  3) $C_3$-$C_7$ cycloalkyl,
  4) haloalkyl,
  5) aryl,
  6) heteroaryl, or
  7) heterocyclyl;
wherein the alkyl and the cycloalkyl are optionally substituted with one or more $R^{10}$ substituents, and the aryl, the heteroaryl and the heterocyclyl are optionally substituted with one or more $R^{20}$ substituents;
R⁹ is
  1) H,
  2) $C_1$-$C_6$ alkyl,
  3) $C_3$-$C_7$ cycloalkyl,
  4) aryl,
  5) heteroaryl, or
  6) heterocyclyl,
in which the alkyl or the cycloalkyl are optionally substituted with one or more $R^{10}$ substituents; and in which the aryl, heteroaryl or heterocyclyl are optionally substituted with one or more $R^{20}$ substituents;
R¹⁰ is independently selected from:
  1) halogen,
  2) $C_1$-$C_6$ alkyl,
  3) $C_3$-$C_7$ cycloalkyl,
  4) haloalkyl, 5) aryl,
6) heteroaryl,
7) heterocyclyl,
8) $OR^9$,
9) $S(O)_m R^9$,
10) $NR^7 R^8$,
11) $COR^9$,
12) $C(O)OR^9$,
13) $OC(O)R^9$,
14) $SC(O)R^9$,
15) $CONR^7 R^8$, or
16) $S(O)_2 NR^7 R^8$, wherein m is an integer of 0, 1, or 2;

$R^{20}$ is independently selected from:
1) halogen,
2) $NO_2$,
3) CN,
4) $C_1$-$C_6$ alkyl,
5) haloalkyl,
6) $C_3$-$C_7$ cycloalkyl,
7) $OR^7$,
8) $NR^7 R^8$,
9) $SR^7$,
10) aryl,
11) heteroaryl,
12) heterocyclyl,
13) $SO_2 R^5$,
14) $SO_3 R^5$,
15) $SOR^5$,
16) $SONHR^5$,
17) $SO_2 NHR^5$,
18) $PO_3 R^5$,
19) $PO(OR^5)_2$,
20) $PO(OR^5)$,
21) $COR^5$,
22) $COR^7$,
23) $CO_2 R^7$,
24) $S(O)_m R^7$,
25) $CONR^7 R^8$, or
26) $S(O)_2 NR^7 R^8$, wherein the alkyl and the cycloalkyl are optionally substituted with one or more $R^6$ substituents; and wherein the aryl, the heteroaryl, or the heterocyclyl are optionally substituted with one or more $R^{30}$; wherein m is an integer of 0, 1, or 2; and $R^{30}$ is
1) $NO_2$,
2) $C_2$-$C_6$ alkene-$R^{20}$,
3) $SO_2 R^5$,
4) $SOR^5$,
5) $SONHR^5$,
6) $SO_2 NHR^5$,
7) CN,
8) $CO_2 R^5$,
9) $COR^5$,
10) $PO_3 R^5$,
11) $PO(OR^5)_2$, or
12) $PO(OR^5)$;

or a pharmaceutically acceptable salt or ester thereof, or the compound is labeled with a detectable label or an affinity tag thereof;

wherein the compound is a caspase inhibitor.

* * * * *